(12) United States Patent
Sanghera et al.

(10) Patent No.: US 10,328,268 B2
(45) Date of Patent: Jun. 25, 2019

(54) CARDIAC PACING

(71) Applicant: AtaCor Medical, Inc., San Clemente, CA (US)

(72) Inventors: Rick Sanghera, San Clemente, CA (US); Alan Marcovecchio, San Clemente, CA (US); Sean P. McGeehan, Encinitas, CA (US)

(73) Assignee: ATACOR MEDICAL, INC., San Clemente, CA (US)

(*) Notice: Subject to any disclaimer, the term of this patent is extended or adjusted under 35 U.S.C. 154(b) by 30 days.

(21) Appl. No.: 15/644,397

(22) Filed: Jul. 7, 2017

(65) Prior Publication Data

US 2017/0304634 A1    Oct. 26, 2017

Related U.S. Application Data

(63) Continuation-in-part of application No. 15/494,126, filed on Apr. 21, 2017, which is a continuation of application No. 14/951,277, filed on Nov. 24, 2015, now Pat. No. 9,636,505, which is a continuation-in-part of application No. 14/846,686, filed on Sep. 4, 2015, now Pat. No. 9,707,389, and a (Continued)

(51) Int. Cl.
| | |
|---|---|
| *A61N 1/00* | (2006.01) |
| *A61N 1/365* | (2006.01) |
| *A61N 1/362* | (2006.01) |
| *A61N 1/05* | (2006.01) |
| *A61N 1/375* | (2006.01) |

(52) U.S. Cl.
CPC ....... *A61N 1/36585* (2013.01); *A61N 1/0504* (2013.01); *A61N 1/0587* (2013.01); *A61N 1/362* (2013.01); *A61N 1/059* (2013.01); *A61N 1/36535* (2013.01); *A61N 1/3752* (2013.01)

(58) Field of Classification Search
CPC .... A61N 1/0504; A61N 1/0587; A61N 1/059; A61N 1/362; A61N 1/36535; A61N 1/36585; A61N 1/3752
See application file for complete search history.

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |

(Continued)

FOREIGN PATENT DOCUMENTS

| | | |
|---|---|---|
| EP | 1530983 A2 | 5/2005 |
| WO | WO-2013/163267 A1 | 10/2013 |

OTHER PUBLICATIONS

PCT/US2017/041265; International Search Report and Written Opinion dated Sep. 25, 2017.

(Continued)

*Primary Examiner* — George Manuel
(74) *Attorney, Agent, or Firm* — Pillsbury Winthrop Shaw Pittman LLP

(57) ABSTRACT

A cardiac pacing system that includes a pulse generator to generate therapeutic electrical pulses and at least one lead inserted through an intercostal space in the region of a cardiac notch of the left lung of a patient, the lead having a distal end configured to transmit the therapeutic electrical pulses generated by the pulse generator to pace the heart of the patient.

6 Claims, 29 Drawing Sheets

Related U.S. Application Data continuation-in-part of application No. 14/846,648, filed on Sep. 4, 2015, now Pat. No. 10,195,422, application No. 15/644,397, which is a continuation-in-part of application No. 14/846,710, filed on Sep. 4, 2015, now Pat. No. 10,022,539.

(60) Provisional application No. 62/359,622, filed on Jul. 7, 2016, provisional application No. 62/146,569, filed on Apr. 13, 2015, provisional application No. 62/083,516, filed on Nov. 24, 2014, provisional application No. 62/045,683, filed on Sep. 4, 2014.

(56) References Cited

U.S. PATENT DOCUMENTS

| | | |
|---|---|---|
| 4,270,549 A | 6/1981 | Heilman |
| 4,280,510 A | 7/1981 | O'Neill |
| 4,291,707 A | 9/1981 | Heilman et al. |
| 4,306,560 A | 12/1981 | Harris |
| 4,437,475 A | 3/1984 | White |
| 4,512,351 A | 4/1985 | Pohndorf |
| 4,532,931 A | 8/1985 | Mills |
| 4,538,624 A | 9/1985 | Tarjan |
| 4,636,199 A | 1/1987 | Victor |
| 4,765,341 A | 8/1988 | Mower et al. |
| 4,787,389 A | 11/1988 | Tarjan |
| 4,832,687 A | 5/1989 | Smith, III |
| 4,846,191 A | 7/1989 | Brockway et al. |
| 4,865,037 A | 9/1989 | Chin et al. |
| 5,036,854 A | 8/1991 | Schollmeyer et al. |
| 5,125,904 A | 6/1992 | Lee |
| 5,176,135 A | 1/1993 | Fain et al. |
| 5,203,348 A | 4/1993 | Dahl et al. |
| 5,255,691 A | 10/1993 | Otten |
| 5,255,692 A | 10/1993 | Neubauer et al. |
| 5,273,053 A | 12/1993 | Pohndorf |
| 5,300,106 A | 4/1994 | Dahl et al. |
| 5,312,355 A | 5/1994 | Lee |
| 5,336,252 A | 8/1994 | Cohen |
| 5,364,361 A | 11/1994 | Battenfield |
| 5,391,156 A | 2/1995 | Hildwein et al. |
| 5,441,504 A | 8/1995 | Pohndorf et al. |
| 5,456,699 A | 10/1995 | Armstrong |
| 5,476,493 A | 12/1995 | Muff |
| 5,509,924 A | 4/1996 | Paspa et al. |
| 5,534,018 A | 7/1996 | Wahlstrand et al. |
| 5,545,205 A | 8/1996 | Schulte et al. |
| 5,562,677 A | 10/1996 | Hildwein et al. |
| 5,571,215 A | 11/1996 | Sterman et al. |
| 5,613,953 A | 3/1997 | Pohndorf |
| 5,690,648 A | 11/1997 | Fogarty et al. |
| 5,716,392 A | 2/1998 | Bourgeois et al. |
| 5,728,151 A | 3/1998 | Garrison et al. |
| 5,752,526 A | 5/1998 | Cosgrove |
| 5,776,110 A | 7/1998 | Guy et al. |
| 5,814,076 A | 9/1998 | Brownlee |
| 5,823,946 A | 10/1998 | Chin |
| 5,871,532 A | 2/1999 | Schroeppel |
| 5,895,414 A | 4/1999 | Sanchez-Zambrano |
| 5,904,711 A | 5/1999 | Flom et al. |
| 5,941,819 A | 8/1999 | Chin |
| 5,944,732 A | 8/1999 | Raulerson et al. |
| 5,951,518 A | 9/1999 | Licata et al. |
| 6,024,704 A | 2/2000 | Meador |
| 6,032,079 A | 2/2000 | KenKnight et al. |
| 6,099,547 A | 8/2000 | Gellman |
| 6,104,957 A | 8/2000 | Alo et al. |
| 6,122,552 A | 9/2000 | Tockman et al. |
| 6,159,198 A | 12/2000 | Gardeski et al. |
| 6,228,052 B1 | 5/2001 | Pohndorf |
| 6,283,127 B1 | 9/2001 | Sterman et al. |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,478,028 B1 | 11/2002 | Paolitto et al. |
| 6,544,247 B1 | 4/2003 | Gardeski et al. |
| 6,651,672 B2 | 11/2003 | Roth |
| 6,706,052 B1 | 3/2004 | Chin |
| 6,718,203 B2 | 4/2004 | Weiner |
| 6,721,597 B1 | 4/2004 | Bardy et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,868,291 B1 | 3/2005 | Bonner et al. |
| 6,887,229 B1 | 5/2005 | Kurth |
| 6,890,295 B2 | 5/2005 | Michels et al. |
| 6,918,908 B2 | 7/2005 | Bonner et al. |
| 6,999,819 B2 | 2/2006 | Swoyer et al. |
| 7,033,326 B1 | 4/2006 | Pianca et al. |
| 7,050,851 B2 | 5/2006 | Plombon et al. |
| 7,069,083 B2 | 6/2006 | Finch et al. |
| 7,096,064 B2 | 8/2006 | Deno et al. |
| 7,117,039 B2 | 10/2006 | Manning et al. |
| 7,191,015 B2 | 3/2007 | Lamson et al. |
| 7,195,637 B2 | 3/2007 | Mika |
| 7,218,970 B2 | 5/2007 | Ley et al. |
| 7,229,450 B1 | 6/2007 | Chitre et al. |
| 7,272,448 B1 | 9/2007 | Morgan et al. |
| 7,288,096 B2 | 10/2007 | Chin |
| 7,316,667 B2 | 1/2008 | Lindstrom et al. |
| 7,319,905 B1 | 1/2008 | Morgan et al. |
| 7,322,960 B2 | 1/2008 | Yamamoto et al. |
| 7,369,899 B2 | 5/2008 | Malinowski et al. |
| 7,373,207 B2 | 5/2008 | Lattouf |
| 7,389,134 B1 | 6/2008 | Karicherla et al. |
| 7,398,781 B1 | 7/2008 | Chin |
| 7,450,997 B1 | 11/2008 | Pianca et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,736,330 B2 | 6/2010 | Bardy |
| 7,761,150 B2 | 7/2010 | Ghanem et al. |
| 7,765,014 B2 | 7/2010 | Eversull et al. |
| 7,801,622 B2 | 9/2010 | Camps et al. |
| 7,837,671 B2 | 11/2010 | Eversull et al. |
| 7,846,088 B2 | 12/2010 | Ness |
| 7,850,610 B2 | 12/2010 | Ferek-Petric |
| 7,890,191 B2 | 2/2011 | Rutten et al. |
| 7,908,015 B2 | 3/2011 | Lazeroms et al. |
| 7,930,028 B2 | 4/2011 | Lang et al. |
| 7,930,040 B1 | 4/2011 | Kelsch et al. |
| 7,967,833 B2 | 6/2011 | Sterman et al. |
| 7,983,765 B1 | 7/2011 | Doan et al. |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,260,436 B2 | 9/2012 | Gerber et al. |
| 8,280,527 B2 | 10/2012 | Eckerdal et al. |
| 8,332,036 B2 | 12/2012 | Hastings et al. |
| 8,340,779 B2 | 12/2012 | Harris et al. |
| 8,355,786 B2 | 1/2013 | Malinowski |
| 8,386,052 B2 | 2/2013 | Harris et al. |
| 8,394,079 B2 | 3/2013 | Drake et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,457,742 B2 | 6/2013 | Jacobson |
| 8,478,424 B2 | 7/2013 | Tronnes |
| 8,478,426 B2 | 7/2013 | Barker |
| 8,478,431 B2 | 7/2013 | Griswold et al. |
| 8,532,789 B2 | 9/2013 | Smits |
| 8,594,809 B2 | 11/2013 | Yang et al. |
| 8,886,311 B2 | 11/2014 | Anderson et al. |
| 9,636,505 B2 | 5/2017 | Sanghera |
| 9,707,389 B2 | 7/2017 | McGeehan |
| 2002/0042629 A1 | 4/2002 | Bardy |

(56) References Cited

U.S. PATENT DOCUMENTS

| | | |
|---|---|---|
| 2002/0120294 A1 | 8/2002 | Kroll |
| 2003/0074041 A1* | 4/2003 | Parry .................. A61N 1/0587 607/130 |
| 2003/0088278 A1 | 5/2003 | Bardy et al. |
| 2003/0114905 A1 | 6/2003 | Kuzma |
| 2003/0114906 A1 | 6/2003 | Booker et al. |
| 2003/0114908 A1 | 6/2003 | Flach |
| 2003/0120264 A1 | 6/2003 | Lattouf |
| 2003/0130581 A1 | 7/2003 | Salo |
| 2003/0187458 A1 | 10/2003 | Carlson |
| 2004/0059348 A1 | 3/2004 | Geske et al. |
| 2004/0088035 A1 | 5/2004 | Guenst et al. |
| 2004/0102829 A1 | 5/2004 | Bonner et al. |
| 2004/0158185 A1 | 8/2004 | Moran |
| 2004/0210293 A1 | 10/2004 | Bardy et al. |
| 2004/0215240 A1 | 10/2004 | Lovett et al. |
| 2004/0230282 A1 | 11/2004 | Cates et al. |
| 2004/0236396 A1 | 11/2004 | Coe et al. |
| 2005/0027328 A1 | 2/2005 | Greenstein |
| 2005/0049663 A1 | 3/2005 | Harris et al. |
| 2005/0131505 A1 | 6/2005 | Yokoyama |
| 2005/0165324 A1 | 7/2005 | Receveur et al. |
| 2005/0192639 A1* | 9/2005 | Bardy .................. A61N 1/375 607/5 |
| 2005/0288731 A1 | 12/2005 | Shames et al. |
| 2005/0288758 A1 | 12/2005 | Jones et al. |
| 2006/0041295 A1 | 2/2006 | Osypka |
| 2006/0089699 A1 | 4/2006 | Imran |
| 2006/0116746 A1 | 6/2006 | Chin |
| 2006/0122676 A1 | 6/2006 | Ko et al. |
| 2006/0129202 A1 | 6/2006 | Armstrong |
| 2006/0136004 A1 | 6/2006 | Cowan et al. |
| 2006/0161205 A1 | 7/2006 | Mitrani et al. |
| 2006/0241711 A1 | 10/2006 | Sathaye |
| 2006/0247753 A1 | 11/2006 | Wenger et al. |
| 2006/0253181 A1 | 11/2006 | Schulman et al. |
| 2006/0266368 A1 | 11/2006 | Heintz |
| 2007/0023947 A1 | 2/2007 | Ludwig et al. |
| 2007/0088394 A1 | 4/2007 | Jacobson |
| 2007/0100409 A1 | 5/2007 | Worley et al. |
| 2007/0150015 A1 | 6/2007 | Zhang |
| 2007/0150023 A1 | 6/2007 | Ignagni et al. |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0103575 A1 | 5/2008 | Gerber |
| 2008/0183230 A1 | 7/2008 | Kemmetmueller |
| 2008/0243219 A1 | 10/2008 | Malinowski et al. |
| 2008/0269716 A1 | 10/2008 | Bonde et al. |
| 2008/0294217 A1 | 11/2008 | Lian et al. |
| 2008/0300644 A1 | 12/2008 | Sathaye |
| 2009/0069803 A1 | 3/2009 | Starkebaum |
| 2009/0157091 A1 | 6/2009 | Buysman |
| 2009/0209970 A1 | 8/2009 | Tanaka |
| 2009/0222021 A1 | 9/2009 | Chang |
| 2009/0259283 A1 | 10/2009 | Brandt et al. |
| 2009/0264780 A1 | 10/2009 | Schilling |
| 2009/0270962 A1 | 10/2009 | Yang et al. |
| 2009/0326346 A1 | 12/2009 | Kracker et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0082087 A1 | 4/2010 | Silipo et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0152798 A1 | 6/2010 | Sanghera et al. |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241189 A1 | 9/2010 | Dobak et al. |
| 2010/0305428 A1 | 12/2010 | Bonner et al. |
| 2010/0318098 A1 | 12/2010 | Lund et al. |
| 2010/0324579 A1 | 12/2010 | Bardy |
| 2011/0009933 A1 | 1/2011 | Barker |
| 2011/0024491 A1 | 2/2011 | Jamali |
| 2011/0066185 A1 | 3/2011 | Wotton, III |
| 2011/0077708 A1 | 3/2011 | Ostroff |
| 2011/0125163 A1 | 5/2011 | Rutten et al. |
| 2011/0152706 A1 | 6/2011 | Christopherson et al. |
| 2011/0178566 A1 | 7/2011 | Stahmann et al. |
| 2011/0224680 A1 | 9/2011 | Barker |
| 2011/0224681 A1 | 9/2011 | McDonald |
| 2011/0230906 A1 | 9/2011 | Modesitt |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0037291 A1 | 2/2012 | Goolishian |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0109250 A1 | 5/2012 | Cates et al. |
| 2012/0123496 A1 | 5/2012 | Schotzko et al. |
| 2012/0191106 A1 | 7/2012 | Ko et al. |
| 2012/0209283 A1 | 8/2012 | Zhu |
| 2012/0209298 A1 | 8/2012 | McClurg et al. |
| 2013/0006326 A1 | 1/2013 | Ackermann |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0178711 A1 | 7/2013 | Avneri |
| 2013/0226266 A1 | 8/2013 | Murtonen |
| 2013/0237781 A1 | 9/2013 | Gyrn |
| 2013/0238067 A1 | 9/2013 | Baudino |
| 2013/0296880 A1 | 11/2013 | Kelley |
| 2013/0338707 A1 | 12/2013 | Killion |
| 2014/0005755 A1 | 1/2014 | Wolf, II |
| 2014/0018872 A1 | 1/2014 | Siejko et al. |
| 2014/0180273 A1 | 6/2014 | Nair |
| 2014/0257421 A1 | 9/2014 | Sanghera et al. |
| 2014/0330208 A1 | 11/2014 | Christie et al. |
| 2014/0330248 A1 | 11/2014 | Thompson-Nauman et al. |
| 2014/0330287 A1 | 11/2014 | Thompson-Nauman et al. |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330328 A1 | 11/2014 | Christie et al. |
| 2014/0330329 A1 | 11/2014 | Thompson-Nauman et al. |
| 2014/0330331 A1 | 11/2014 | Thompson-Nauman et al. |
| 2015/0013689 A1 | 1/2015 | Shackelford |
| 2015/0051612 A1 | 2/2015 | Schmidt et al. |
| 2015/0051615 A1 | 2/2015 | Schmidt et al. |
| 2015/0088155 A1 | 3/2015 | Stahmann et al. |
| 2015/0142069 A1 | 5/2015 | Sambelashvili |
| 2015/0157497 A1 | 6/2015 | Hufford |
| 2015/0223906 A1 | 8/2015 | O'Neill |
| 2015/0328473 A1 | 11/2015 | Bodner et al. |
| 2016/0051159 A1 | 2/2016 | Mazaeva |
| 2016/0067479 A1 | 3/2016 | Marcovecchio et al. |
| 2016/0067480 A1 | 3/2016 | Sanghera et al. |
| 2016/0067488 A1 | 3/2016 | Sanghera et al. |
| 2016/0144192 A1 | 5/2016 | Sanghera et al. |
| 2016/0184047 A1 | 6/2016 | Weir |
| 2017/0224995 A1 | 8/2017 | Sanghera |
| 2017/0304019 A1 | 10/2017 | Sanghera |
| 2018/0021572 A1 | 1/2018 | McGeehan |
| 2018/0050199 A1 | 2/2018 | Sanghera |

OTHER PUBLICATIONS

Brown, Charles G., et. al. "Injuries Associated with Percutaneous Placement of Transthoracic Pacemakers." *Annals of Emergency Medicine* 14.3 (1985): 223-228.

Brown, Charles G., et. al. "Placement Accuracy of Percutaneous Transthoracic Pacemakers." *The American Journal of Emergency Medicine* 3.3 (1985): 193-198.

Nagdev, Arun, and Daniel Mantuani. "A Novel In-plane Technique for Ultrasound-guided Pericardiocentesis." *The American Journal of Emergency Medicine* 31.9 (2013): 1424.e5-1424.e9.

(56) References Cited

OTHER PUBLICATIONS

Pai, N. V., et. al. "Relation of Internal Thoracic Artery to Lateral Sternal Border and Its Significance in Clinical Procedures." *International Journal of Biological & Medical Research* 4.4 (2013): 3633-3636.

Office Action dated Aug. 27, 2018 for U.S. Appl. No. 15/788,760 (pp. 1-14).

Office Action dated Oct. 2, 2018 for U.S. Appl. No. 15/494,126 (pp. 1-8).

Notice of Allowance dated Oct. 9, 2018 for U.S. Appl. No. 14/846,648 (pp. 1-8).

Corrected Notice of Allowability dated Oct. 25, 2018 for U.S. Appl. No. 14/846,648 (pp. 1-4).

Office Action dated Oct. 31, 2018 for U.S. Appl. No. 14/846,578 (pp. 1-11).

* cited by examiner

P-wave Expectation Window

CARDIAC PACING

CROSS-REFERENCE TO RELATED APPLICATIONS

This application claims the benefit of U.S. Provisional Patent Application 62/359,622, filed Jul. 7, 2016, the disclosure of which is incorporated herein by reference in its entirety. This application is also a continuation in part of U.S. patent application Ser. No. 15/494,126, filed Apr. 21, 2017, which is a continuation of U.S. patent application Ser. No. 14/951,277, filed Nov. 24, 2015, now U.S. Pat. No. 9,636,505, which claims priority to and the benefit of U.S. Provisional Patent Application 62/083,516, filed Nov. 24, 2014, U.S. Provisional Patent Application 62/146,569, filed Apr. 13, 2015, and is a continuation in part of U.S. patent application Ser. No. 14/846,710, filed Sep. 4, 2015, and a continuation in part of U.S. patent application Ser. No. 14/846,686, filed Sep. 4, 2015, and a continuation in part of U.S. patent application Ser. No. 14/846,648, filed Sep. 4, 2015, the disclosures of which are incorporated herein by reference in their entirety. This application is also a continuation in part of U.S. patent application Ser. No. 14/846,710, filed Sep. 4, 2015, which claims priority to and the benefit of U.S. Provisional Application 62/045,683, filed Sep. 4, 2014, the disclosures of which are incorporated herein by reference in their entirety.

BACKGROUND

An artificial pacemaker is a medical device that helps control abnormal heart rhythms. A pacemaker uses electrical pulses to prompt the heart to beat at a normal rate. The pacemaker may speed up a slow heart rhythm, control a fast heart rhythm, and coordinate the chambers of the heart. The implantable portions of a pacemaker system generally comprise three main components: a pulse generator, one or more wires called leads, and electrodes found on each lead. The pulse generator produces the electrical signals that make the heart beat. Most pulse generators also have the capability to receive and respond to signals that are sent by the heart. Leads are insulated flexible wires that conduct electrical signals to the heart from the pulse generator. The leads may also relay signals from the heart to the pulse generator. One end of the lead is attached to the pulse generator and the electrode end of the lead is positioned on or in the heart.

SUMMARY

Cardiac pacing systems and methods are disclosed, in which some implementations may include a pulse generator configured to generate therapeutic electrical pulses for the pacing of a heart of a patient and also a lead disposed in the region of a cardiac notch of the left lung of the patient, where the lead may have a distal end configured to transmit the therapeutic electrical pulses generated by the pulse generator.

In some variations, the pulse generator is implanted within the patient or disposed outside of a patient's rib cage and a portion of the lead may be positioned through an intercostal space of the patient.

In other variations, the distal end of the lead may be positioned within an intercostal space of the patient, on the inner surface of the innermost intercostal muscle, or within the mediastinum, proximate to the heart, but not physically in contact with the heart.

In some variations, the cardiac pacing system may include a sensor disposed at a distal end of the lead. The sensor may be configured to monitor a physiological characteristic of the patient. The pulse generator may then be configured to adjust the generated therapeutic electrical pulses based on signals received from the lead sensor.

In an interrelated aspect, a cardiac pacing method is disclosed. The method may include inserting a lead into an intercostal space in the region of a cardiac notch of a patient. The lead may have a distal end configured to transmit therapeutic electrical pulses to a patient's heart and the method may include connecting the lead to a pulse generator configured to generate the therapeutic electrical pulses for pacing the patient's heart.

In some variations, the method may include implanting the pulse generator within the patient, or may include positioning the pulse generator outside of a patient's rib cage.

In other variations, inserting the lead may further include positioning the distal end within the intercostal space, positioning the distal end on the inner surface of the innermost intercostal muscle, or positioning the distal end within the mediastinum, proximate the heart, but not physically in contact with the heart.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Implantable medical devices (IMDs), such as cardiac pacemakers or implantable cardioverter defibrillators (ICDs), provide therapeutic electrical stimulation to the heart of a patient. This electrical stimulation may be delivered via electrodes on one or more implantable endocardial or epicardial leads that are positioned in or on the heart. This electrical stimulation may also be delivered using a leadless cardiac pacemaker disposed within a chamber of the heart. Therapeutic electrical stimulation may be delivered to the heart in the form of electrical pulses or shocks for pacing, cardioversion or defibrillation.

An implantable cardiac pacemaker may be configured to facilitate the treatment of cardiac arrhythmias. The devices, systems and methods of the present disclosure may be used to treat cardiac arrhythmias including, but not limited to, bradycardia, tachycardia, atrial flutter and atrial fibrillation. Resynchronization pacing therapy may also be provided.

A cardiac pacemaker consistent with the present disclosure may include a pulse generator implanted adjacent the rib cage of the patient, for example, on the ribcage under the pectoral muscles, laterally on the ribcage, within the mediastinum, subcutaneously on the sternum of the ribcage, and the like. One or more leads may be connected to the pulse generator. A lead may be inserted, for example, between two ribs of a patient so that the distal end of the lead is positioned within the mediastinum of the patient adjacent, but not touching, the heart. The distal end of the lead may include an electrode for providing electrical pulse therapy to the patient's heart and may also include at least one sensor for detecting a state of the patient's organs and/or systems. The cardiac pacemaker may include a unitary design where the components of the pulse generator and lead are incorporated within a single form factor. For example, where a first portion of the unitary device resides within the subcutaneous tissue and a second portion of the unitary device is placed through an intercostal space into a location within the mediastinum.

Figure 1:
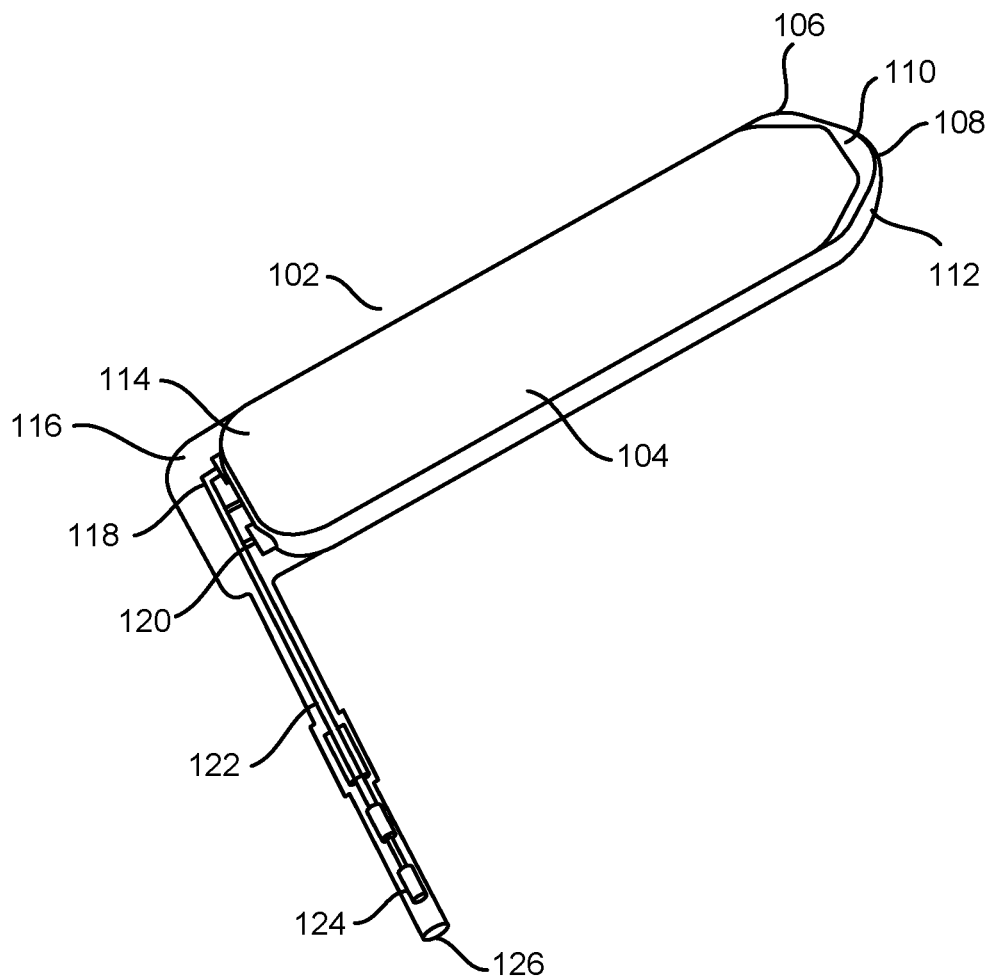
FIG. 1 is a front-view of an exemplary pulse generator having features consistent with implementations of the current subject matter.

FIG. 1 is a front-view 100 of a pulse generator 102 having features consistent with implementations of the current subject matter. The pulse generator 102 may be referred to as a cardiac pacemaker. The pulse generator 102 can include a housing 104, which may be hermetically sealed. In the present disclosure, and commonly in the art, housing 104 and everything within it may be referred to as a pulse generator, despite there being elements inside the housing other than those that generate pulses (for example, processors, storage, battery, etc.).

Housing 104 can be substantially rectangular in shape and the first end of the housing 104 may include a tapered portion 108. The tapered portion can include a first tapered edge 110, tapered inwardly toward the transverse plane. The tapered portion 108 can include a second tapered edge 112 tapered inwardly toward the longitudinal plane. Each of the first tapered edge 110 and the second tapered edge 112 may have a similar tapered edge generally symmetrically disposed on the opposite side of tapered portion 108, to form two pairs of tapered edges. The pairs of tapered edges may thereby form a chisel-shape at the first end 106 of pulse generator 102. When used in the present disclosure, the term "chisel-shape" refers to any configuration of a portion of housing 104 that facilitates the separation of tissue planes during placement of pulse generator 102 into a patient. The "chisel-shape" can facilitate creation of a tightly fitting and properly sized pocket in the patient's tissue in which the pulse generator may be secured. For example, a chisel-shape portion of housing 104 may have a single tapered edge, a pair of tapered edges, 2 pairs of tapered edges, and the like. Generally, the tapering of the edges forms the shape of a chisel or the shape of the head of a flat head screwdriver. In some variations, the second end 114 of the pulse generator can be tapered. In other variations, one or more additional sides of the pulse generator 102 can be tapered.

Housing 104 of pulse generator 102 can include a second end 114. The second end 114 can include a port assembly 116. Port assembly 116 can be integrated with housing 104 to form a hermetically sealed structure. Port assembly 116 may be configured to facilitate the egress of conductors from housing 104 of pulse generator 102 while maintaining a seal. For example, port assembly 116 may be configured to facilitate the egress of a first conductor 118 and a second conductor 120 from housing 104. The first conductor 118 and the second conductor 120 may combine within port assembly 116 to form a twin-lead cable 122. In some variations, the twin-lead cable 122 can be a coaxial cable. The twin-lead cable 122 may include a connection port 124 remote from housing 104. Connection port 124 can be configured to receive at least one lead, for example, a pacing lead. Connection port 124 of the cable 122 can include a sealed housing 126. Sealed housing 126 can be configured to envelope a portion of the received lead(s) and form a sealed connection with the received lead(s).

Port assembly 116 may be made from a different material than housing 104. For example, housing 104 may be made from a metal alloy and port assembly 116 may be made from a more flexible polymer. While port assembly 116 may be manufactured separately from housing 104 and then integrated with it, port assembly 116 may also be designed to be part of housing 104 itself. The port assembly 116 may be externalized from the housing 104 as depicted in FIG. 1. The port assembly 116 may be incorporated within the shape of housing 104 of pulse generator 102.

Figure 2:
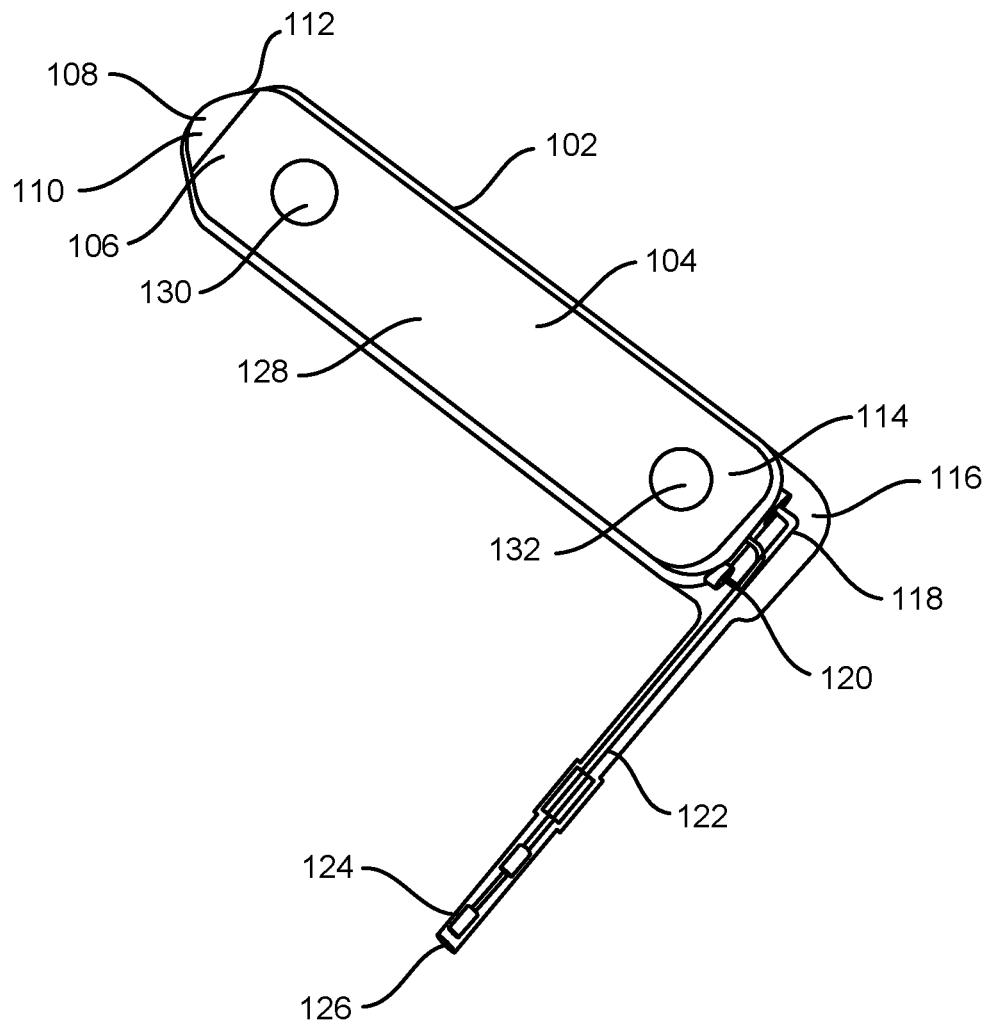
FIG. 2 is a rear-view of an exemplary pulse generator having features consistent with implementations of the current subject matter.

FIG. 2 is a rear-view 200 of pulse generator 102 showing the back-side 128 of housing 104. As shown, pulse generator 102 can include one or more electrodes or sensors disposed within housing 104. As depicted in the example of FIG. 2, housing 104 includes a first in-housing electrode 130 and a second in-housing electrode 132. The various electrodes illustrated and discussed herein may be used for delivering therapy to the patient, sensing a condition of the patient, and/or a combination thereof. A pulse generator consistent with the present disclosure installed at or near the sternum of a patient can monitor the heart, lungs, major blood vessels, and the like through sensor(s) integrated into housing 104.

Figure 3:
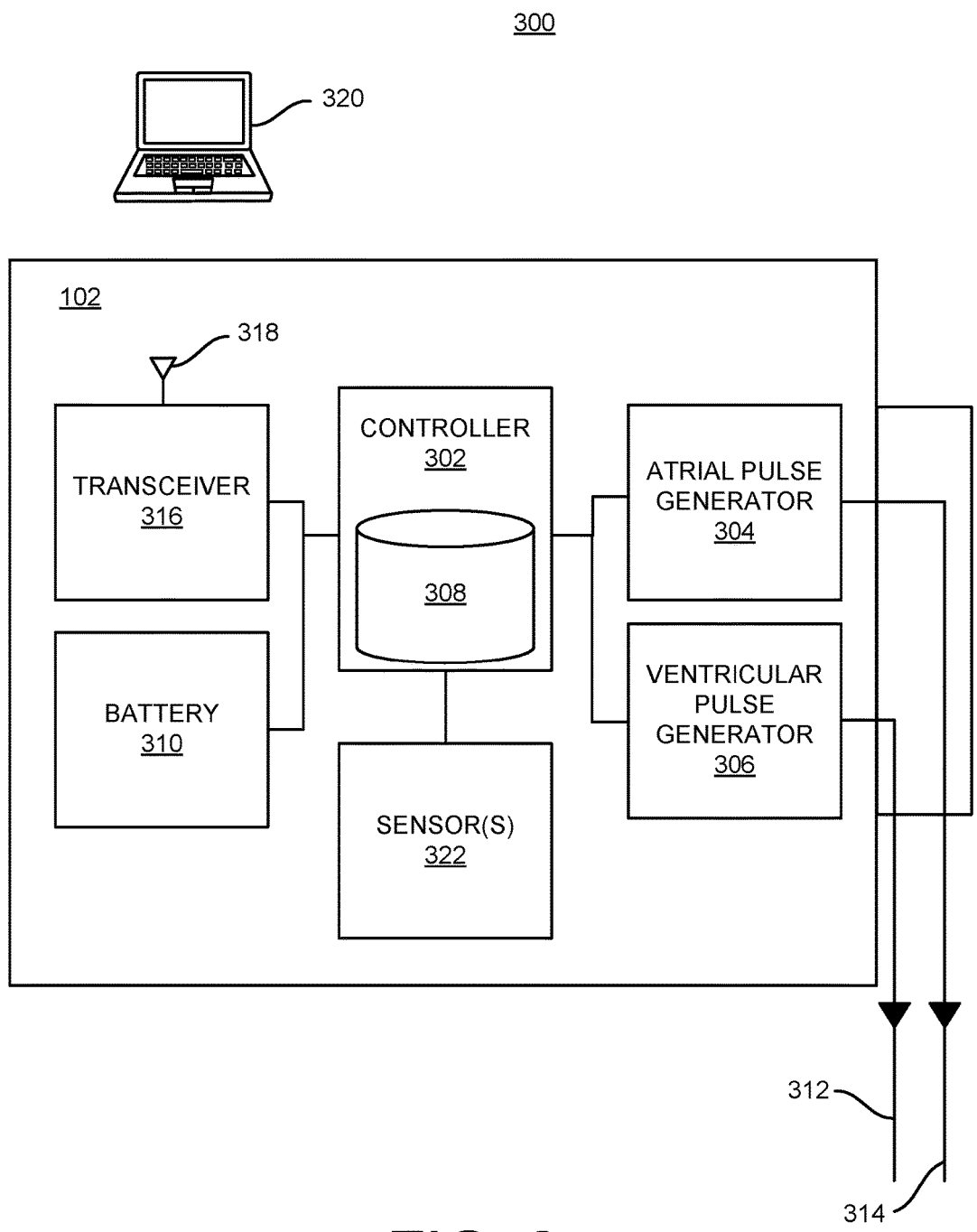
FIG. 3 is an illustration of a simplified schematic diagram of an exemplary pulse generator having features consistent with implementations of the current subject matter.

FIG. 3 is an illustration 300 of a simplified schematic diagram of an exemplary pulse generator 102 having features consistent with the current subject matter. Pulse generator 102 can include signal processing and therapy circuitry to detect various cardiac conditions. Cardiac conditions can include ventricular dyssynchrony, arrhythmias such as bradycardia and tachycardia conditions, and the like. Pulse generator 102 can be configured to sense and discriminate atrial and ventricular activity and then deliver appropriate electrical stimuli to the heart based on a sensed state of the heart.

Pulse generator 102 can include one or more components. The one or more components may be hermetically sealed within the housing 104 of pulse generator 102. Pulse generator 102 can include a controller 302, configured to control the operation of the pulse generator 102. The pulse generator 102 can include an atrial pulse generator 304 and may also include a ventricular pulse generator 306. Controller 302 can be configured to cause the atrial pulse generator 304 and the ventricular pulse generator 306 to generate electrical pulses in accordance with one or more protocols that may be loaded onto controller 302. Controller 302 can be configured to control pulse generators 304, 306, to deliver electrical pulses with the amplitudes, pulse widths, frequency, or electrode polarities specified by the therapy protocols, to one or more atria or ventricles.

Controller electronic storage 308 can store instructions configured to be implemented by the controller to control the functions of pulse generator 102.

Controller 302 can include a processor(s). The processor(s) can include any one or more of a microprocessor, a controller, a digital signal processor (DSP), an application specific integrated circuit (ASIC), a field-programmable gate array (FPGA), or equivalent discrete or analog logic circuitry. The functions attributed to controller 302 herein may be embodied as software, firmware, hardware or any combination thereof.

The pulse generator 102 can include a battery 310 to power the components of the pulse generator 102. In some variations, battery 310 can be configured to charge a capacitor. Atrial pulse generator 304 and ventricular pulse generator 306 can include a capacitor charged by the battery 310. The electrical energy stored in the capacitor(s) can be discharged as controlled by controller 302. The electrical energy can be transmitted to its destination through one or more electrode leads 312, 314. The leads can include a ventricular pulsing lead 312, an atrial pulsing lead 314, and/or other leads.

Pulse generator 102 can include one or more sensors 322. Sensor(s) 322 can be configured to monitor various aspects of a patient's physiology. Sensor(s) 322 may be embedded in the housing of pulse generator 102, incorporated into leads 312, 314 or be incorporated into separate leads. Sensors 322 of pulse generator 102 can be configured to detect, for example, signals from a patient's heart. The signals can be decoded by controller 302 of the pulse generator to determine a state of the patient. In response to detecting a cardiac arrhythmia, controller 302 can be configured to cause appropriate electrical stimulation to be transmitted through electrodes 312 and 314 by atrial pulse generator 304 and/or ventricular pulse generator 306.

Sensor(s) 322 can be further configured to detect other physiological states of the patient, for example, a respiration rate, blood oximetry, and/or other physiological states. In variations where the pulse generator 102 utilizes a plurality of electrodes, controller 302 may be configured to alter the sensing and delivery vectors between available electrodes to enhance the sensitivity and specificity of arrhythmia detection and improve efficacy of the therapy delivered by the electrical impulses from the pulse generator 102.

Pulse generator 102 can include a transceiver 316. The transceiver can include an antenna 318. The transceiver 316 can be configured to transmit and/or receive radio frequency signals. The transceiver 316 can be configured to transmit and/or receive wireless signals having any wireless communication protocol. Wireless communication protocols can include Bluetooth, Bluetooth low energy, Near-Field Communication, WiFi, and/or other radio frequency protocols. The transceiver 316 can be configured to transmit and/or receive radio frequency signals to and/or from a programmer 320. The programmer 320 can be a computing device external to the patient. Programmer 320 may comprise a transceiver configured to transmit and/or receive radio frequency signals to and/or from the transceiver 316 of the pulse generator 102. Transceiver 316 can be configured to wirelessly communicate with programmer 320 through induction, radio-frequency communication or other short-range communication methodologies.

In some variations, programmer 320 can be configured to communicate with the pulse generator 102 through longer-range remote connectivity systems. Such longer-range remote connectivity systems can facilitate remote access, by an operator, to pulse generator 102 without the operator being in close proximity with the patient. Longer-range remote connectivity systems can include, for example, remote connectivity through the Internet, and the like. When an operator connects with pulse generator 102 through longer-range remote connectivity systems, a local device can be positioned within a threshold distance of the patient. The local device can communicate using one or more radio-frequency wireless connections with the pulse generator 102. The local device can, in turn, include hardware and/or software features configured to facilitate communication between it and an operator device at which the operator is stationed. The local device can be, for example, a mobile computing device such as a smartphone, tablet, laptop, and the like. The local device can be a purpose-built local device configured to communicate with the pulse generator 102. The local device can be paired with the pulse generator 102 such that the communications between the pulse generator 102 and the local device are encrypted. Communications between the local device and the operator device can be encrypted.

Programmer 320 can be configured to program one or more parameters of the pulse generator 102. The parameter(s) can include timing of the stimulation pulses of the atrial pulse generator, timing of the stimulation pulses of the ventricular pulse generator, timing of pulses relative to certain sensed activity of the anatomy of the patient, the energy levels of the stimulation pulses, the duration of the stimulation pulses, the pattern of the stimulation pulses and other parameters. The programmer 320 can facilitate the performance of diagnostics on the patient or the pulse generator 102.

Programmer 320 can be configured to facilitate an operator of the programmer 320 to define how the pulse generator 102 senses electrical signals, for example ECGs, and the like. The programmer 320 can facilitate an operator of the programmer 320 to define how the pulse generator 102 detects cardiac conditions, for example ventricular dyssynchrony, arrhythmias, and the like. The programmer 320 can facilitate defining how the pulse generator 102 delivers therapy, and communicates with other devices.

An operator can fine-tune parameters through the programmer 320. For example, the sensitivity of sensors embodied in the housing of the pulse generator 302, or within leads, can be modified. Programmer 320 can facilitate setting up communication protocols between the pulse generator 102 and another device such as a mobile computing device. Programmer 320 can be configured to facilitate modification of the communication protocols of the pulse generator 102, such as adding security layers, or preventing two-way communication. Programmer 320 can be configured to facilitate determination of which combination of implanted electrodes are best suited for sensing and therapy delivery.

Programmer 320 can be used during the implant procedure. For example, programmer 320 can be used to determine if an implanted lead is positioned such that acceptable performance will be possible. If the performance of the system is deemed unacceptable by programmer 320, the lead may be repositioned by the physician, or an automated delivery system, until the lead resides in a suitable position. Programmer 320 can also be used to communicate feedback from sensors disposed on the leads and housing 104 during the implant procedure.

In some cases, concomitant devices such as another pacemaker, an ICD, or a cutaneous or implantable cardiac monitor, can be present in a patient, along with pulse generator 102. Pulse generator 102 can be configured to communicate with such concomitant devices through transceiver 316 wirelessly, or the concomitant device may be physically connected to pulse generator 102. Physical connection between devices may be accomplished using a lead emanating from pulse generator 102 that is compatible with the concomitant device. For example, the distal end of a lead emanating from pulse generator 102 may be physically and electrically connected to a port contained on the concomitant device. Physical connection between devices may also be accomplished using an implantable adaptor that facilitates electrical connection between the lead emanating from pulse generator 102 and the concomitant device. For example, an adapter may be used that will physically and electrically couple the devices despite not having native components to facilitate such connection. Concomitant devices may be connected using a "smart adapter" that provides electrical connection between concomitant devices and contains signal processing capabilities to convert signal attributes from each respective device such that the concomitant devices are functionally compatible with each other.

Pulse generator 102 can be configured to have a two-way conversation or a one-way conversation with a concomitant device. Controller 302 can be configured to cause the concomitant device to act in concert with pulse generator 102 when providing therapy to the patient, or controller 302 can gather information about the patient from the concomitant device. In some variations, pulse generator 102 can be configured to be triggered via one-way communication from a concomitant device to pulse generator 102.

Figure 4A:
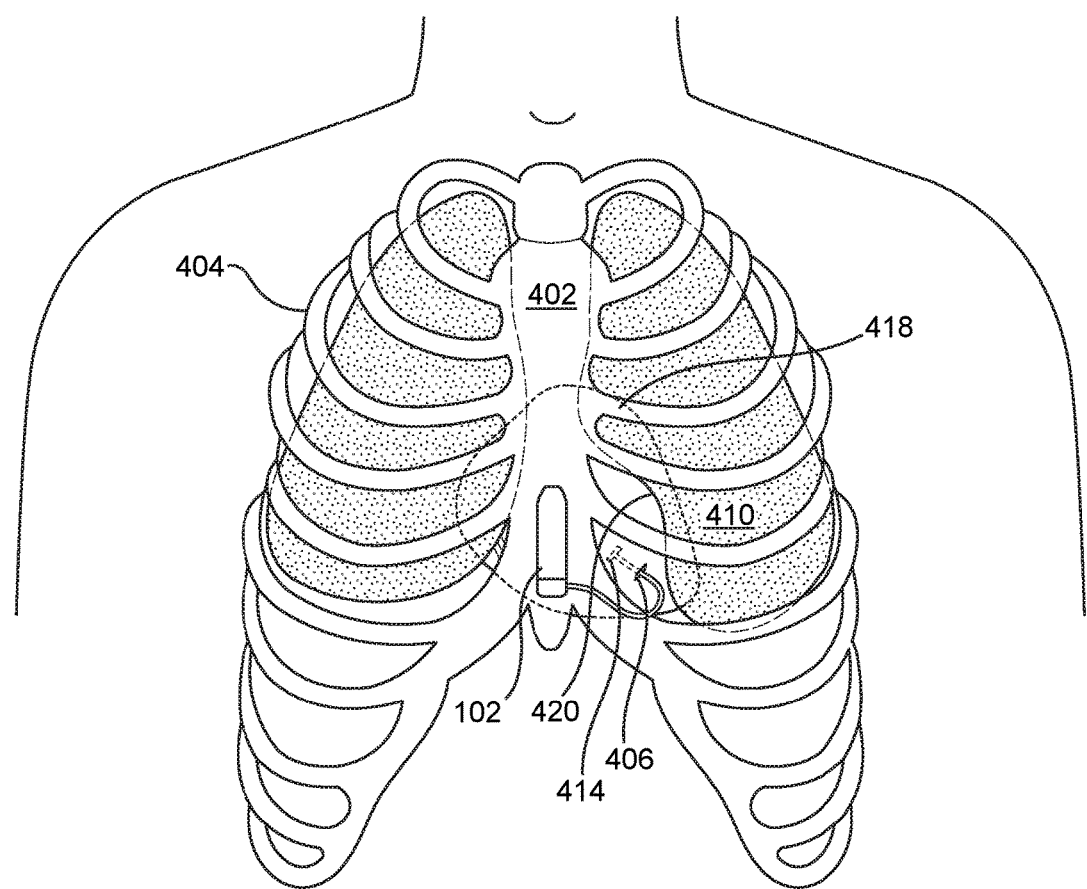
FIG. 4A is an illustration showing exemplary placements of elements of a cardiac pacing system having features consistent with the current subject matter.
Figure 4B:
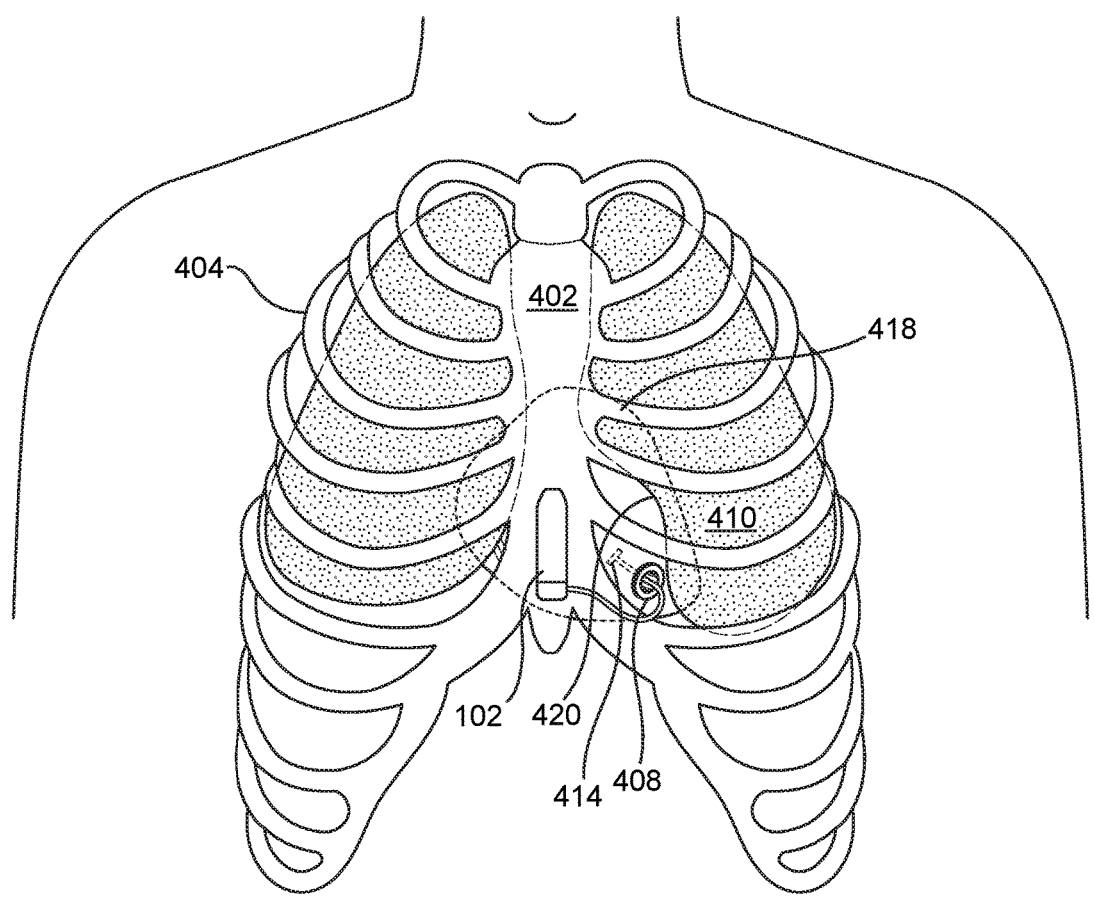
FIG. 4B is an illustration showing exemplary placements of elements of a cardiac pacing system having features consistent with the current subject matter.

FIGS. 4A and 4B are illustrations showing exemplary placements of elements of a cardiac pacing system having features consistent with the present disclosure. Pulse generator 102 can be disposed in a patient, adjacent an outer surface of ribcage 404. For example, pulse generator 102 can be disposed on the sternum 402 of the patient's ribcage 404. A lead 414, attached to pulse generator 102, may also be disposed in the patient by traversing through intercostal muscle 410 of the patient. Lead 414 may optionally pass through a receptacle 408 in intercostal muscle 410 to guide the lead, fix the lead, and/or electrically insulate the lead from the tissue of the intercostal muscle 410 (examples of such receptacles are described herein with respect to FIGS. 13-16).

In other variations, pulse generator 102 can be disposed outside of a patient's ribcage in a pectoral position, outside of the patient's ribcage in a lateral position, below (inferior to) the patient's ribcage in a subxiphoid or abdominal position, within the patient's mediastinum, or the like.

Lead 414 may be passed through the ribcage so the distal end of the lead and its electrodes are disposed on, or pass through, the inner surface of the rib or inner surface of the innermost intercostal muscle, or may alternatively traverse further within the thoracic cavity, but without physically contacting the tissue comprising the heart. This placement may be referred to herein as intracostal or intracostally.

Leads may be inserted between any two ribs within the thoracic cavity, for example, as shown in FIG. 4A. In some variations, it is desirable to insert the lead through one of the intercostal spaces associated with cardiac notch of the left lung 420. For example, between the fourth and fifth ribs or between the fifth and sixth ribs. Due to variations in anatomy, the rib spacing associated with the cardiac notch of the left lung 420 may differ. In some patients the cardiac notch of the left lung 420 may not be present or other cardiac anomalies such as dextrocardia may require the insertion through alternative rib spaces. Lead 414 may be inserted into such a location through an incision 406, as shown in FIG. 4A. Lead 414 may optionally be inserted into such a location through a receptacle 408, as shown in FIG. 4B.

Figure 4C:
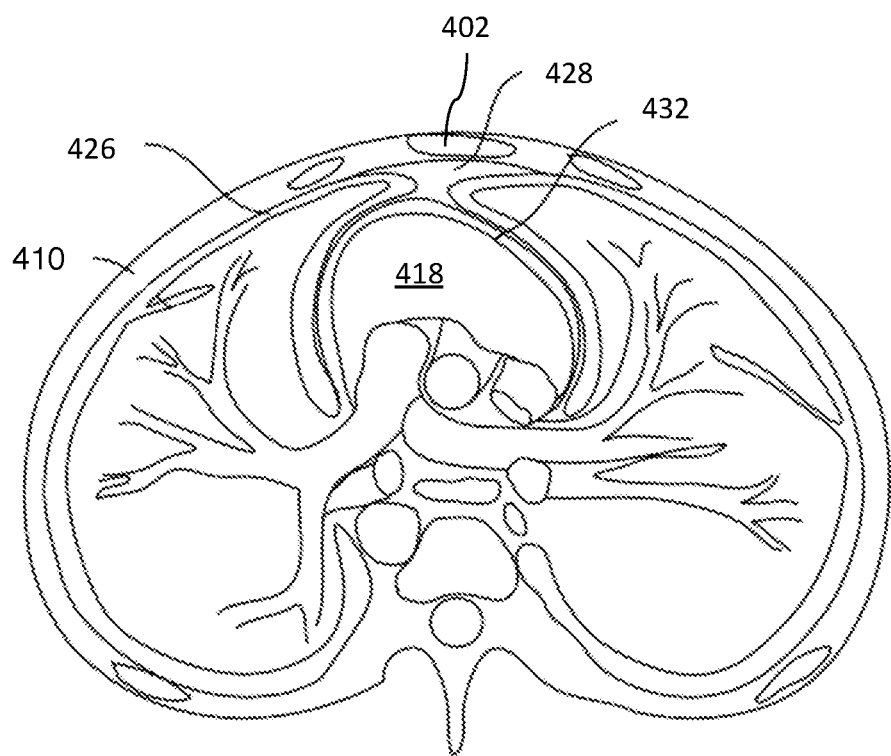
FIG. 4C is a cross-sectional illustration of a thoracic region of a patient.

Precise placement of a distal end of lead 414, which may include electrode(s) for pacing or sensing, is now described further with reference to the anatomical illustrations of FIGS. 4A, 4B and 4C. In some variations, the distal end of lead 414 can be located within the intercostal space or intercostal muscle 410. In such variations, the distal end of lead 414 is preferably surrounded by a receptacle 408 that electrically insulates the distal end of the lead 414 from the intercostal muscle 410. In another variation, the distal end of lead 414 may be placed just on the inner surface of a rib or on the inner surface of the innermost intercostal muscle.

The distal end of lead 414 can also be positioned so as to abut the parietal pleura of the lung 426. In other variations, the distal end of lead 414 can be positioned so as to terminate within the mediastinum 428 of the thoracic cavity of the patient, proximate the heart 418, but not physically in contact with the heart 418 or the pericardium 432 of heart 418. Alternatively, the distal end of lead 414 can be placed to abut the pericardium 432, but not physically attach to the epicardial tissue comprising the heart.

The distal end of lead 414 may be physically affixed to cartilage or bone found within the thoracic cavity, for example, to a rib, to cartilage of a rib, or to other bone or cartilage structure in the thoracic cavity. In one variation, the lead can be disposed such that it is wrapped around the patient's sternum 402.

For certain placements, lead 414 can be adequately fixed by direct physical contact with surrounding tissue. In other variations, an additional fixation mechanism may be used. For example, the distal end of lead 414 can incorporate a fixation mechanism such as a tine, hook, spring, screw, or other fixation device. The fixation mechanism can be configured to secure the lead in the surrounding tissue, cartilage, bone, or other tissue, to prevent the lead from migrating from its original implantation location.

Figure 5:
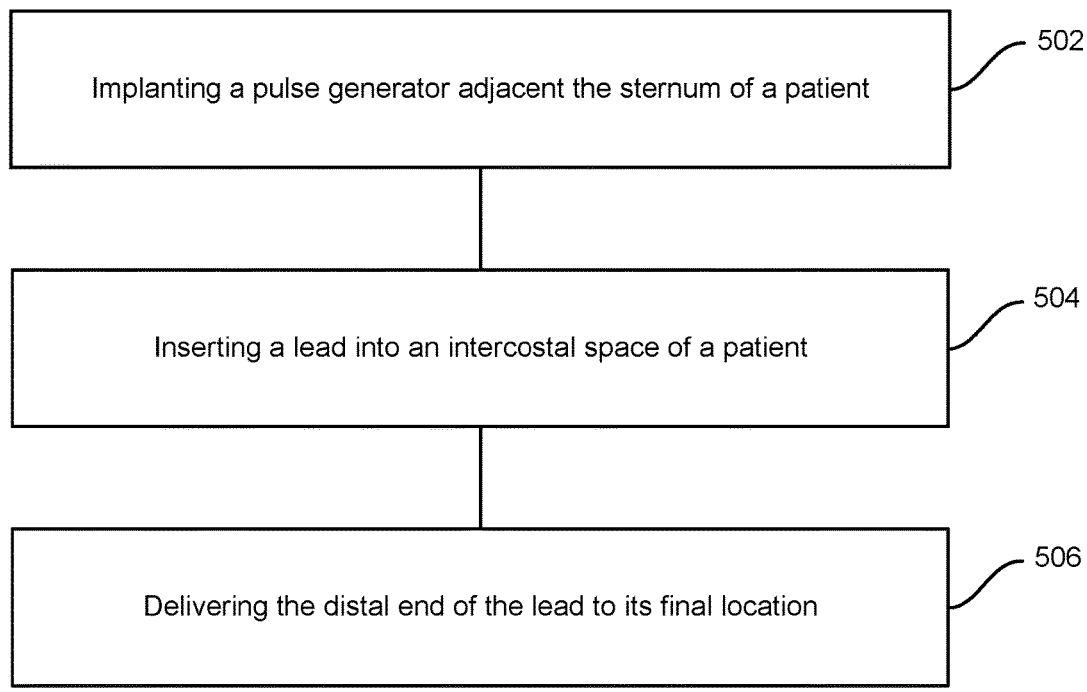
FIG. 5 is an illustration of an exemplary method of implanting a cardiac pacing system into a patient having features consistent with the current subject matter.

FIG. 5 is an illustration 500 of an exemplary method of implanting a cardiac pacing system into a patient consistent with the present disclosure. At 502, a pulse generator 102 may be implanted, in a manner described above, adjacent the sternum 402 of a patient. Optionally, pulse generator 102 may be at least partially chisel-shaped to facilitate implantation and the separation of tissue planes. At 504, a lead 414 may be inserted into an intercostal space 410 of a patient. As described above, lead 414 may optionally be inserted into a receptacle 408 disposed within intercostal space 410. At 506, the distal end of lead 414 is delivered to one of a number of suitable final locations for pacing, as described above.

Figure 6A:
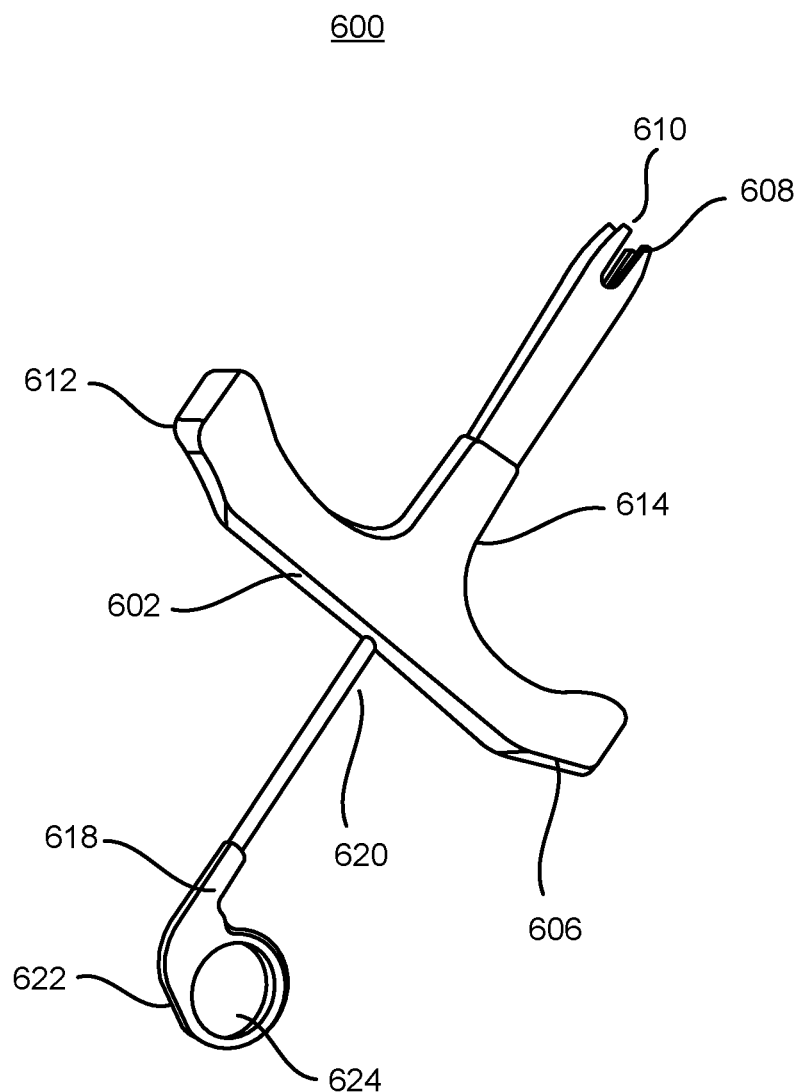
FIG. 6A is an illustration of an exemplary delivery system for a pulse generator having features consistent with implementations of the current subject matter.
Figure 6B:
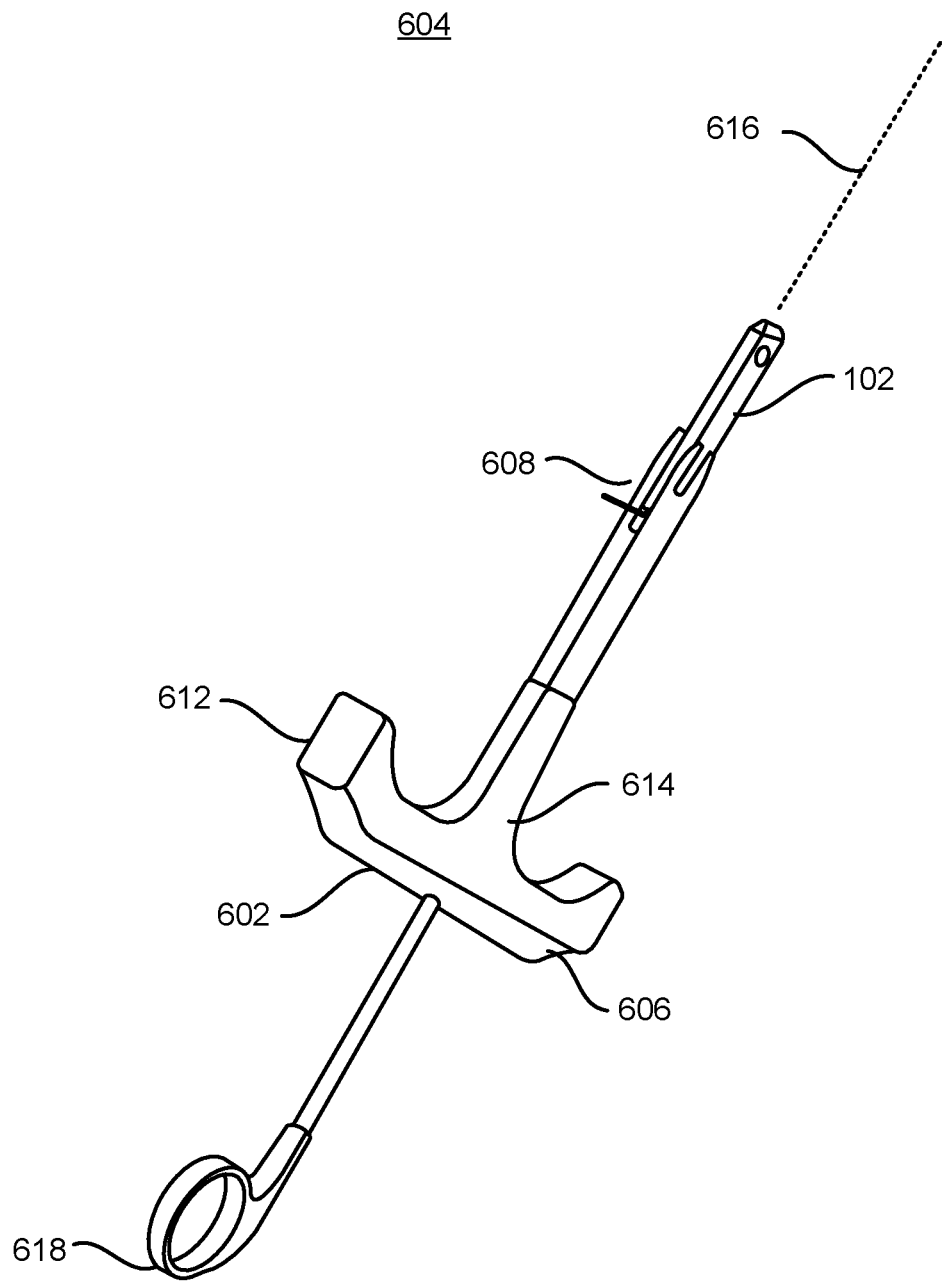
FIG. 6B is an illustration of an exemplary delivery system with a pulse generator disposed therein consistent with implementations of the current subject matter.

FIG. 6A is an illustration 600 of a pulse generator delivery system 602 for facilitating positioning of pulse generator 102 into a patient, the delivery system 602 having features consistent with the current subject matter. FIG. 6B is an illustration 604 of the delivery system 602 as illustrated in FIG. 6A with the pulse generator 102 mounted in it. Delivery system 602 can be configured to facilitate implantation of the pulse generator 102 into the thoracic region of a patient.

Delivery system 602 includes a proximal end 606 and a distal end 608. The distal end 608 of delivery system 602 contains a receptacle 610 in which the housing of the pulse generator 102 is loaded. Where the pulse generator 102 contains a connection lead, the delivery system 602 can be configured to accommodate the connection lead so that the connection lead will not be damaged during the implantation of the pulse generator 102.

When pulse generator 102 is fully loaded into delivery system 602, pulse generator 102 is substantially embedded into the receptacle 610. In some variations, a portion of the pulse generator 102's distal end can be exposed, protruding from the end of receptacle 610. The tapered shape of the distal end 106 of pulse generator 102 can be used in conjunction with the delivery system 602 to assist with separating tissue planes as delivery system 602 is used to advance pulse generator 102 to its desired location within the patient.

In some variations, the entirety of pulse generator 102 can be contained within receptacle 610 of the delivery system 602. The pulse generator 102 in such a configuration will not be exposed during the initial advancement of delivery system 602 into the patient. The distal end 608 of delivery system 602 may be designed to itself separate tissue planes within the patient as delivery system 602 is advanced to the desired location within the patient.

The pulse generator delivery system 602 may be made from a polymer, a metal, a composite material or other suitable material. Pulse generator delivery system 602 can include multiple components. Each component of the pulse generator delivery system 602 can be formed from a material suitable to the function of the component. The pulse generator delivery system 602 can be made from a material capable of being sterilized for repeated use with different patients.

Pulse generator delivery system 602 may include a handle 612. Handle 612 can facilitate advancement of delivery system 602 and pulse generator 102 into a patient's body. Handle 612 can be disposed on either side of the main body 614 of the delivery system 602, as illustrated in FIGS. 6A and 6B. In some variations, handle 612 can be disposed on just one side of the main body 614 of the delivery system 602. The handle 612 can be configured to be disposed parallel to plane of insertion and advancement 616 of pulse generator delivery system 602 within the body. In some variations, handle 612 can be located orthogonally to the plane of insertion and advancement 616 of the delivery system 602. Handle 612 can be configured to facilitate the exertion of pressure, by a physician, onto the pulse generator delivery system 602, to facilitate the advancement and positioning of the delivery system 602 at the desired location within the patient.

Pulse generator delivery system 602 can include a pulse generator release device 618. The release device 618 can be configured to facilitate disengagement of the pulse generator 102 from the delivery system 602. In some variations, release device 618 can include a plunger 620. Plunger 620 can include a distal end configured to engage with the proximal end 606 of the pulse generator delivery system 602. The plunger 620 can engage with the proximal end 606 of the pulse generator delivery system 602 when the pulse generator 102 is loaded into the receptacle 610 of the delivery system 602. The proximal end 622 of the plunger 620 can extend from the proximal end 606 of the delivery system 602.

Plunger 620 can include a force applicator 624. Force applicator 624 can be positioned at the proximal end 622 of plunger 620. Force applicator 624 can be configured to facilitate application of a force to the plunger 620 to advance the plunger 620. Advancing plunger 620 can force pulse generator 102 from the delivery system 602. In some variations, the force applicator 624 can be a ring member. The ring member can facilitate insertion, by the physician, of a finger. Pressure can be applied to the plunger 620 through the ring member, forcing the pulse generator 102 out of the receptacle 610 of the delivery system 602 into the patient at its desired location. In some variations, the proximal end 622 of the plunger 620 can include a flat area, for example, similar to the flat area of a syringe, that allows the physician to apply pressure to the plunger 620. In some variations, the plunger 620 can be activated by a mechanical means such as a ratcheting mechanism.

The distal end 608 of the pulse generator delivery device 602 can include one or more sensors. The sensor(s) can be configured to facilitate detection of a state of patient tissues adjacent distal end 608 of the pulse generator delivery device 602. Various patient tissues can emit, conduct and/or reflect signals. The emitted, conducted and/or reflected signals can provide an indication of the type of tissue encountered by the distal end 608 of the pulse generator delivery device 602. Such sensor(s) can be configured, for example, to detect the electrical impedance of the tissue adjacent the distal end 608 of the pulse generator delivery device 602. Different tissues can have different levels of electrical impedance. Monitoring the electrical impedance can facilitate a determination of the location, or tissue plane, of the distal end 608 of the delivery device 602.

In addition to delivery of the pulse generator, delivery of at least one lead for sensing and/or transmitting therapeutic electrical pulses from the pulse generator is typically required. Proper positioning of the distal end of such lead(s) relative to the heart is very important. Delivery systems are provided that can facilitate the insertion of one or more leads to the correct location(s) in the patient. The delivery systems can facilitate finding the location of the initial insertion point for the lead. The initial insertion point optionally being an intercostal space associated with a patient's cardiac notch of the left lung. The intercostal spaces associated with the cardiac notch commonly include the left-hand-side fourth, fifth and sixth intercostal spaces. Other intercostal spaces on either side of the sternum may be used, especially when the patient is experiencing conditions that prevent use of the fourth, fifth and sixth intercostal spaces, or due to anatomical variations.

When making the initial insertion through the epidermis and the intercostal muscles of the patient, it is important to avoid damaging important blood-filled structures of the patient. Various techniques can be employed to avoid damaging important blood-filled structures. For example, sensors can be used to determine the location of the blood-filled structures. Such sensors may include accelerometers configured to monitor pressure waves caused by blood flowing through the blood-filed structures. Sensors configured to emit and detect light-waves may be used to facilitate locating tissues that absorb certain wavelengths of light and thereby locate different types of tissue. Temperature sensors may be configured to detect differences in temperature between blood-filled structures and surrounding tissue. Lasers and detectors may be employed to scan laser light across the surface of a patient to determine the location of subcutaneous blood-filled structures.

Conventional medical devices may be employed to locate the desired initial insertion point into the patient. For example, x-ray machines, MM machines, CT scanning machines, fluoroscopes, ultrasound machines and the like, may be used to facilitate determination of the initial insertion point for the leads as well as facilitate in advancing the lead into the patient.

Advancing a lead into a patient can also present the risk of damaging physiological structures of the patient. Sensors may be employed to monitor the characteristics of tissues within the vicinity of the distal end of an advancing lead. Readings from sensors associated with the characteristics of tissues can be compared against known characteristics to determine the type of tissue in the vicinity of the distal end of the advancing lead.

Sensors, such as pH sensors, thermocouples, accelerometers, electrical impedance monitors, and the like, may be used to detect the depth of the distal end of the electrode in the patient. Physiological characteristics of the body change the further a lead ventures into it. Measurements performed by sensors at, or near, the distal end of the advancing lead may facilitate the determination of the type of tissue in the vicinity of the distal end of the lead, as well as its depth into the patient.

Various medical imaging procedures, may be used on a patient to determine the location of the desired positions in the heart for the distal end of the lead(s). This information can be used, in conjunction with sensor readings, of the kind described herein, to determine when the distal end of the lead has advanced to a desired location within the patient.

Components may be used to first create a channel to the desired location for the distal end of the lead. Components can include sheaths, needles, cannulas, balloon catheters and the like. A component may be advanced into the patient with the assistance of sensor measurements to determine the location of the distal end of the component. Once the component has reached the desired location, the component may be replaced with the lead or the lead may be inserted within the component. An example of a component can include an expandable sheath. Once the sheath has been advanced to the desired location, a cannula extending the length of the sheath may be expanded, allowing a lead to be pass through the cannula. The sheath may then be removed from around the lead, leaving the lead in situ with the distal end of the lead at the desired location.

Determination of the final placement of the distal end of a lead is important for the delivery of effective therapeutic electrical pulses for pacing the heart. The present disclosure describes multiple technologies to assist in placement of a lead in the desired location. For example, the use of sensors on the pulse generator, on the distal end of leads, or on delivery components. In addition, when a lead or component is advanced into a patient, balloons may be employed to avoid damaging physiological structures of the patient. Inflatable balloons may be disposed on the distal end of the lead or component, on the sides of a lead body of the lead, or may be circumferentially disposed about the lead body. The balloons may be inflated to facilitate the displacement of tissue from the lead to avoid causing damage to the tissue by the advancing lead. A lead delivery assembly may also be used to facilitate delivery of the lead to the desired location. In some variations, the lead delivery assembly may be configured to automatically deliver the distal end of the lead to the desired location in the patient.

Figure 7:
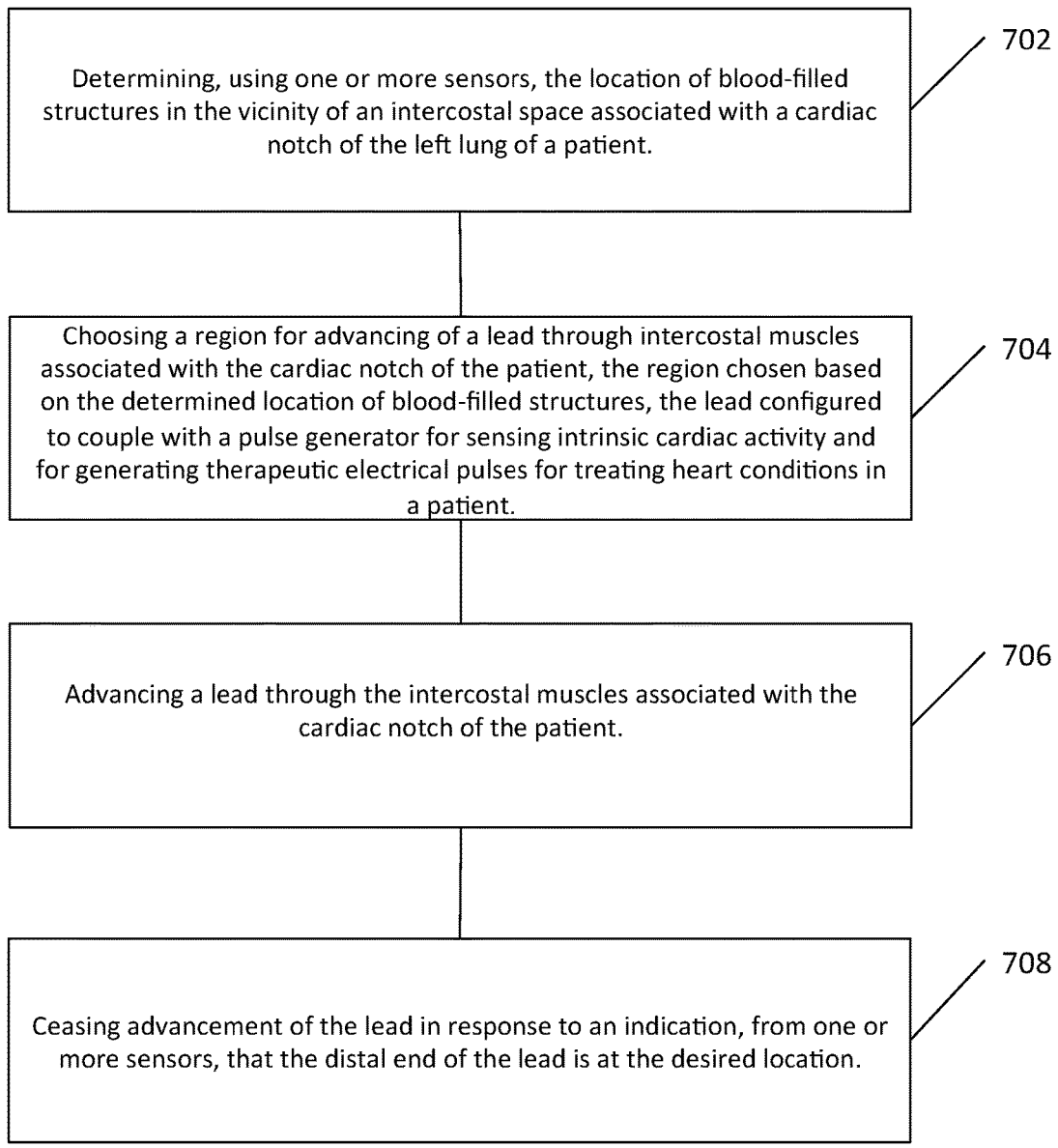
FIG. 7 is an illustration of an exemplary process flow illustrating a method of placing a pacing lead having features consistent with the current subject matter.

FIG. 7 is an illustration 700 of an exemplary process flow illustrating a method of delivering a lead having features consistent with the present disclosure. At 702, the location of blood-filled structures, in the vicinity of an intercostal space, can be determined. The intercostal space can be an intercostal space associated with the cardiac notch of the patient. Determining the location of the blood-filed structures may be facilitated by one or more sensors configured to detect the location of blood-filled structures.

At 704, a region can be chosen for advancing of a lead through intercostal muscles associated with the cardiac notch. The region chosen may be based on the determined location of blood-filled structures of the patient in that region. It is important that damage to blood-filled structures, such as arteries, veins, and the like, is avoided when advancing a lead into a patient.

At 706, a lead can be advanced through the intercostal muscles associated with the cardiac notch of the patient. Care should be taken to avoid damaging important physiological structures. Sensors, of the kind described herein, may be used to help avoid damage to important physiological structures.

At 708, advancement of the lead through the intercostal muscles can be ceased. Advancement may be ceased in response to an indication that the distal end of the lead has advanced to the desired location. Indication that the distal end of the lead is at the desired location may be provided through measurements obtained by one or more sensors of the kind described herein.

Figure 8A:
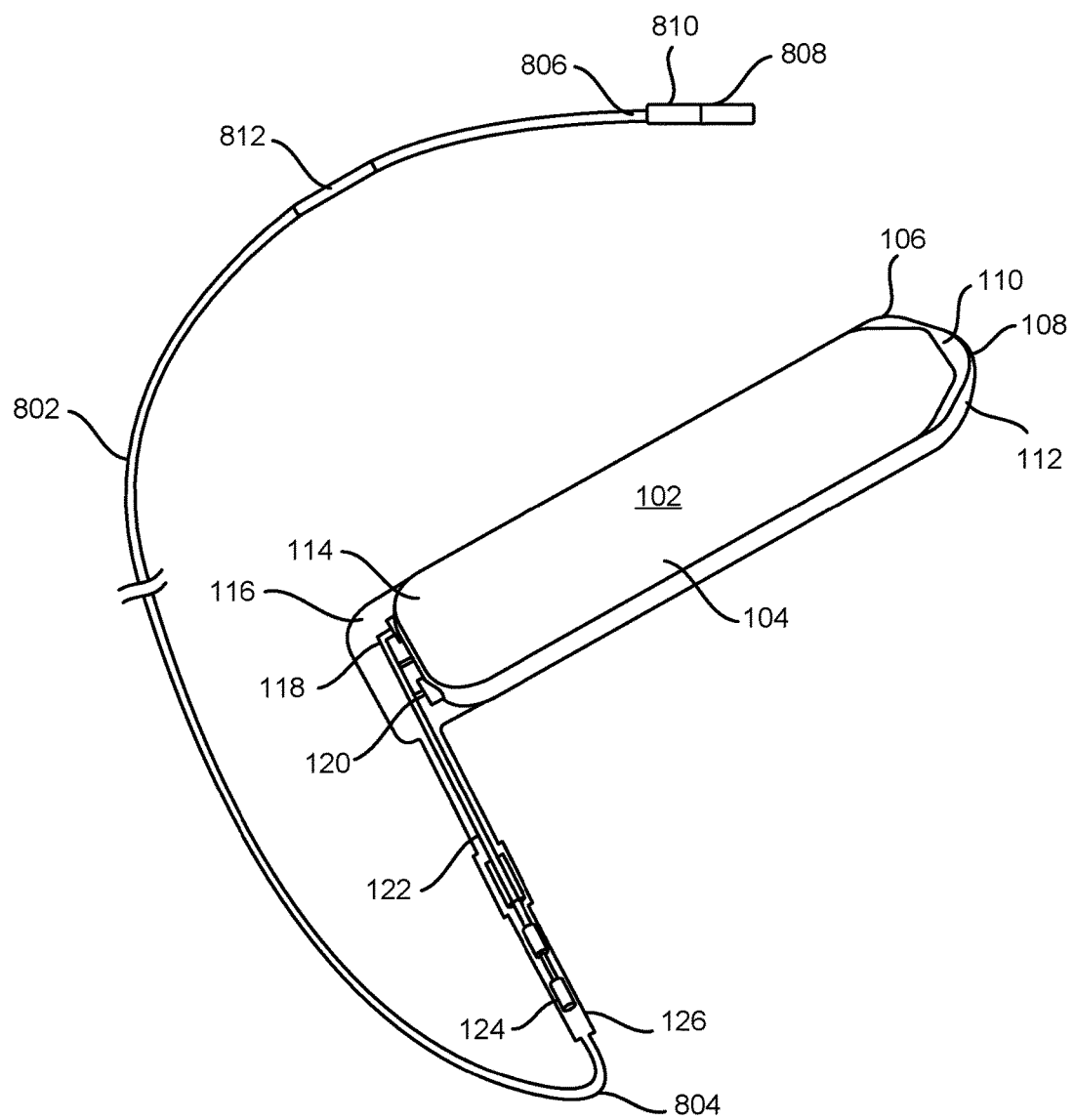
FIG. 8A is an illustration of an exemplary lead having features consistent with the current subject matter.

The lead advanced through the intercostal muscles associated with the cardiac notch of the patient can be configured to transmit therapeutic electrical pulses to pace the patient's heart. FIG. 8A is an illustration 800a of an exemplary lead 802 having features consistent with the present disclosure. For the lead to deliver therapeutic electrical pulses to the heart for pacing the heart, a proximal end 804 of lead 802 is configured to couple with the pulse generator 102. The proximal end 804 of lead 802 may be configured to couple with a connection port 124. The connection port can be configured to couple the proximal end 804 of lead 802 to one or more conductors, such as conductors 118 and 120. When the proximal end 804 of lead 802 couples with connection port 124, a sealed housing may be formed between them. In some variations, the materials of connection port 124 and the proximal end 804 of lead 802 may be fused together. In some variations, the proximal end 804 of lead 802 may be configured to be pushed into the sealed housing 126, or vice versa. Optionally, the external diameter of the inserted member may be slightly greater than the internal diameter of the receiving member causing a snug, sealed fit between the two members. Optionally, a mechanism, such as a set-screw or mechanical lock, may be implemented upon the connection port 124 or proximal lead end 804 in order to prevent unintentional disconnection of the lead 802 from pulse generator 102.

Also shown in FIG. 8A is the distal end 806 of lead 802. The distal end 806 of lead 802 may comprise an electrode 808. In some variations, lead 802 may include a plurality of electrodes. In such variations, lead 802 may include a multiple-pole lead. Individual poles of the multiple-pole lead can feed into separate electrodes. Electrode 808 at the distal end 806 of lead 802 may be configured to deliver electrical pulses to pace the heart when located in the desired position for pacing the heart.

The distal end 806 of lead 802 can include one or more sensors 810. Sensor(s) 810 can be configured to monitor physiological characteristics of the patient while the distal end 806 of lead 802 is being advanced into the patient. Sensors can be disposed along the length of lead 802. For example, sensor 812 is disposed some distance from the distal end 806. Such sensors incorporated onto the lead can detect subtle physiological, chemical and electrical differences that distinguish the lead's placement within the desired location, as opposed to other locations in the patient's thoracic cavity.

In some variations, the proximal end 804 of lead 802 may be coupled with pulse generator 102 prior to the distal end 806 of lead 802 being advanced through the intercostal space of the patient. In some variations, the proximal end 804 of the lead 802 may be coupled with pulse generator 102 after the distal end 806 of lead 802 has been advanced to the desired location.

To assist in the placement of the lead, various medical instruments may be used. The medical instruments may be used alone, or in combination with sensors disposed on the lead that is being placed. Medical instruments may be used to help the physician to access the desired location for the placement of a lead and/or confirm that the distal end of the lead has reached the desired location. For example, instruments, such as an endoscope or laparoscopic camera, with its long, thin, flexible (or rigid) tube, light and video camera can assist the physician in confirming that the distal end 806 of lead 802 has reached the desired location within the thoracic cavity. Other tools known to one skilled in the art such as a guidewire, guide catheter, or sheath may be used in conjunction with medical instruments, such as the laparoscopic camera, and may be advanced alongside and to the location identified by the medical instruments. Medical instruments such as a guidewire can be advanced directly to the desired location for the distal end of the lead with the assistance of acoustic sound, ultrasound, real-time spectroscopic analysis of tissue, real-time density analysis of tissue or by delivery of contrast media that may be observed by real-time imaging equipment.

In some variations, the patient may have medical devices previously implanted that may include sensors configured to monitor physiological characteristics of the patient. The physiological characteristics of the patient may change based on the advancement of the lead through the intercostal space of the patient. The previously implanted medical device may have sensors configured to detect movement of the advancing lead. The previously implanted medical device can be configured to communicate this information back to the physician to verify the location of the advancing lead.

Sensors disposed on the lead, such as sensors 810 disposed on distal end 806 of the lead may be used to facilitate the delivery of the lead to the desired location. Sensor(s) 810 can be configured to facilitate determination of a depth of the distal end 806 of lead 802. As described above, the depth of the desired location within the patient can be determined using one or more medical instruments. This can be determined during implantation of the lead 802 or prior to the procedure taking place.

Although sensor(s) 810 is illustrated as a single element in FIG. 8A, sensor(s) 810 can include multiple separate sensors. The sensors 810 can be configured to facilitate placement of the distal end 806 of the lead 802 at a desired location and verification thereof.

Sensor(s) 810 can be configured to transmit sensor information during advancement to the desired location. Sensor(s) 810 may transmit signals associated with the monitored physiological characteristics of the tissue within the vicinity of the distal end 806 of the lead 802. In some variations, the signals from sensor(s) 810 may be transmitted to a computing device(s) configured to facilitate placement of the lead 802 in the desired location. In such variations, the computing device(s) can be configured to assess the sensor information individually, or in the aggregate, to determine the location of the distal end 806 of lead 802. The computing device(s) can be configured to present alerts and/or instructions associated with the position of the distal end 806 of lead 802.

In some variations, lead 802 can be first coupled with connection port 124 of pulse generator 102. Signals generated by sensor(s) 810 can be transmitted to a computing device(s) using transceiver 316 in pulse generator 102, as illustrated in FIG. 3.

An accelerometer may be used to facilitate delivery of the distal end 806 of lead 802 to the desired location. An accelerometer may be disposed at the distal end 806 of lead 802. The accelerometer may be configured to monitor the movement of the distal end 806 of lead 802. The accelerometer may transmit this information to a computing device or the physician. The computing device, or the physician, can determine the location of the distal end 806 of the lead 802 based on the continuous movement information received from the accelerometer as the lead 802 is advanced into the patient. The computing device or the physician may know the initial entry position for lead 802. The movement information can indicate a continuous path taken by the lead 802 as it advanced into the body of the patient, thereby providing an indication of the location of the distal end 806 of lead 802. Pressure waves from the beating heart may differ as absorption changes within deepening tissue planes. These pressure wave differences may be used to assess the depth of the distal end of the electrode.

The accelerometer can also be configured to monitor acoustic pressure waves generated by various anatomical structures of the body. For example, the accelerometer can be configured to detect acoustic pressure waves generated by the heart or by other anatomical structures of the body. The closer the accelerometer gets to the heart, the greater the acoustic pressure waves generated by the heart will become. By comparing the detected acoustical pressure waves with known models, a location of the distal end 806 of lead 802 can be determined.

Pressure waves or vibrations can be artificially generated to cause the pressure waves or vibrations to traverse through the patient. The pressure waves or vibrations can be generated in a controlled manner. The pressure waves or vibrations may be distorted as they traverse through the patient. The level of type of distortion that is likely to be experienced by the pressure waves or vibrations may be known. The pressure waves or vibrations detected by the accelerometer can be compared to the known models to facilitate determination or verification of the location of the distal end 806 of lead 802.

Different tissues within a body exhibit different physiological characteristics. The same tissues situated at different locations within the body can also exhibit different physiological characteristics. Sensors, disposed on the distal end 806, of lead 802 can be used to monitor the change in the physiological characteristics as the distal end 806 is advanced into the body of the patient. For example, the tissues of a patient through which a lead is advanced can demonstrate differing resistances, physiological properties, electrical impedance, temperature, pH levels, pressures, and the like. These different physiological characteristics, and the change in physiological characteristics, experienced as a sensor traverses through a body can be known or identified. For example, even if the actual degree is not known ahead of time, the change in sensor input when the sensor traverses from one tissue media to another may be identifiable in real-time. Consequently, sensors configured to detect physiological characteristics of a patient can be employed to facilitate determining and verifying the location of the distal end 806 of lead 802.

Different tissues can exhibit different insulative properties. The insulative properties of tissues, or the change in insulative properties of tissues, between the desired entry-point for the lead and the desired destination for the lead can be known. Sensor 810 can include an electrical impedance detector. An electrical impedance detector can be configured to monitor the electrical impedance of the tissue in the vicinity of the distal end 806 of lead 802. The electrical impedance of the tissue monitored by the electrical impedance detector can be compared with the known insulative properties of the tissues between the entry point and the destination, to determine the location of the distal end of lead 802 or a transition from one tissue plane to another may be recognized by a measurable change in the measured impedance.

Varying levels of electrical activity can be experienced at different locations with the body. Electrical signals emitted from the heart, or other muscles can send electrical energy through the body. This electrical energy will dissipate the further it gets from its source. Various tissues will distort the electrical energy in different ways. Sensors configured to detect the electrical energy generated by the heart and/or other anatomical structures can monitor the electrical energy as the lead is advanced. By comparing the monitored electrical energy with known models, a determination or verification of the location of the distal end 806 of lead 802 can be made. The sensors may be configured to identify sudden changes in the electrical activity caused by advancement of the sensor into different tissue planes.

Tissues throughout the body have varying pH levels. The pH levels of tissues can change with depth into the body. Sensor(s) 810 can include a pH meter configured to detect the pH levels of the tissue in the vicinity of the sensor(s) 810 as the sensor(s) advance through the patient. The detected pH levels, or detected changes in pH levels, can be compared with known models to facilitate determination or verification of the location of the distal end 806 of lead 802. The pH meter may be configured to identify sudden changes in the pH level caused by advancement of the meter into different tissue planes.

Different tissues can affect vibration-waves or sound-waves in different ways. Sensor(s) 810 can include acoustic sensors. The acoustic sensors can be configured to detect vibration waves or sound waves travelling through tissues surrounding sensor(s) 810. The vibration waves can be emitted by vibration-emitting devices embedded the lead 802. The vibration waves can be emitted by vibration-emitting devices located on a hospital gurney, positioned on the patient, or otherwise remote from lead 802. Sensor(s) 810 can be configured to transmit detected vibration-wave information to a computing device configured to determine the location of the distal end 806 of lead 802 based on the detected vibration-wave information.

Different tissues can have different known effects on the emitted electromagnetic waves. Sensors can be used to detect the effect that the tissue in the vicinity of the sensors have on the electromagnet waves. By comparing the effect that the tissue has on the electromagnetic waves with known electromagnetic effects, the identity of the tissue can be obtained and the location of the lead can be determined or verified. For example, sensor(s) 810 can include electromagnetic wave sensors. Electromagnetic wave sensors can include an electromagnetic wave emitter and an electromagnetic wave detector. The electromagnetic waves will be absorbed, reflected, deflected, and/or otherwise affected by tissue surrounding sensor(s) 810. Sensor(s) 810 can be configured to detect the change in the reflected electromagnetic waves compared to the emitted electromagnetic waves. By comparing the effect the tissue in the vicinity of the sensor(s) 810 has on the electromagnetic waves with known models, a determination verification of the location of lead 802 can be made. The sensors may be configured to identify sudden changes in the electromagnetic activity caused by advancement of the sensor into different tissue planes.

Figure 9A:
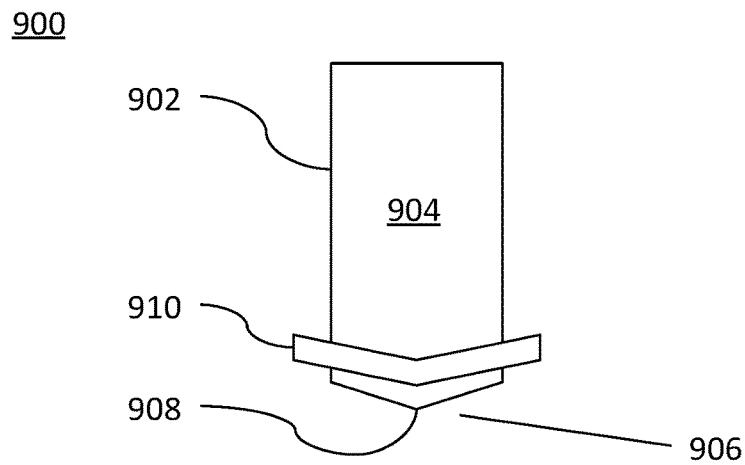
FIG. 9A is an illustration of the distal end of an exemplary delivery system having features consistent with the current subject matter.

FIG. 9A is an illustration 900 of the distal end of an exemplary delivery system 902 having features consistent with the presently described subject matter. While FIG. 9A is described with reference to a delivery system, one of ordinary skill in the art can appreciate and understand that the technology described herein could be applied directly to the end of a lead, such as lead 802. The present disclosure is intended to apply to a delivery system, such as delivery system 902, as well as a lead, such as lead 802.

Delivery system 902 can facilitate placement of the distal end of a lead, such as lead 802 illustrated in FIG. 8, to a desired location by use of electromagnetic waves, such as light waves. Delivery system 902 may comprise a delivery catheter body 904. Delivery catheter body 904 may be configured to facilitate advancement of delivery catheter body 904 into the patient to a desired location. The distal tip 906 of delivery catheter body 904 may comprise a light source 908. Light source 908 can be configured to emit photons having a visible wavelength, infrared wavelength, ultraviolet wavelength, and the like. Delivery catheter body 904 may comprise a light detector 910. Light detector 910 may be configured to detect light waves, emitted by the light source 908, reflected by tissues surrounding distal tip 906 of delivery catheter body 904.

Figure 9B:
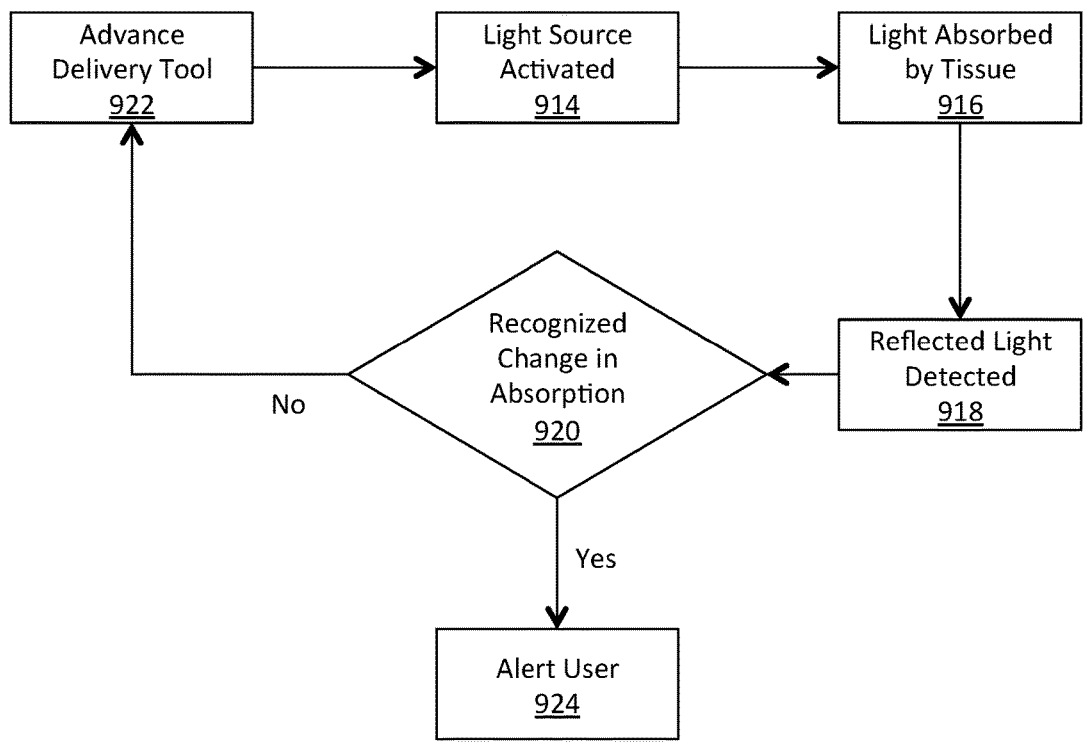
FIG. 9B is an illustration of an exemplary process for using the delivery system illustrated in FIG. 9A.

FIG. 9B is an illustration 912 of an exemplary process for using the delivery system illustrated in FIG. 9A. Light detector 910 can be configured to detect light waves reflected by the tissue adjacent the distal end 906 of delivery system 902. Information associated with the detected light waves may be transmitted to a computing device. The computing device can be configured to interpret the information transmitted from light detector 910 and determine a difference between the light emitted and the light detected.

At 914, light source 908 can be activated. Light source 908 may emit light-waves into the tissue in the general direction of the intended advancement of delivery system 902. At 916, the tissue can absorb a portion of the emitted light waves. At 918, light detector 910 can detect the reflected light waves, reflected by tissues surrounding light source 908. At 920, a determination of a change in the absorption of the light waves by tissues surrounding the distal tip 906 of delivery system 902 can be made.

At 922, in response to an indication that the absorption of light waves has not changed, delivery system 902 can be configured to advance a delivery system, such as delivery system 902, into the patient. In some variations, a physician can advance delivery system 902 into the patient. In other variations, the delivery system 902 can be advanced into the patient automatically.

At 924, in response to an indication that the absorption of light waves has changed, an alert can be provided to the physician. In some variations, the alert can be provided to the physician through a computing device configured to facilitate positioning of delivery system 902 into the patient.

In some variations, a computing device may be configured to facilitate positioning of delivery system 902 into the patient. The computing device can be configured to alert the physician to the type of tissue in the vicinity of distal tip 906 of delivery system 902. In some variations, the computing device can be configured to alert the physician when the distal tip 906 reaches a tissue having characteristics consistent with the desired location of the distal tip 906 of delivery system 902. For example, when the characteristics of the tissue in the vicinity of the distal tip 906 match those within the intercostal tissues, or a particular location within the medistiunum, an alert may be provided.

Blood vessels, both venous and arterial, absorb red, near infrared and infrared (IR) light waves to a greater degree than surrounding tissues. When illuminating the surface of the body with red, near infrared and infrared (IR) light waves, blood rich tissues, for example veins, will absorb more of this light than other tissues, and other tissues will reflect more of this light than the blood rich tissues. Analysis of the pattern of reflections can enable the blood rich tissues to be located. A positive or negative image can be projected on the skin of the patient at the location of the vein. In some variations, the vein can be represented by a bright area and the absence of a vein can be represented as a dark area, or vice versa.

Delivery system 902 can include a subcutaneous visualization enhancer. The subcutaneous visualization enhancer may be configured to enhance visualization of veins, arteries, and other subcutaneous structures of the body. The subcutaneous visualization enhancer can include moving laser light sources to detect the presence of blood-filled structures, such as venous or arterial structures below the surface of the skin. The subcutaneous visualization enhancer can include systems configured to project an image onto the surface of the skin that can show an operator the pattern of the detected subcutaneous blood-filled structures. Laser light from laser light sources can be scanned over the surface of the body using mirrors. A light detector can be configured to measure the reflections of the laser light and use the pattern of reflections to identify the targeted blood rich structures.

Such subcutaneous visualization enhancers can be used to facilitate determination of the location for the initial approach for inserting a lead, such as lead 802, through the intercostal space associated with the cardiac notch of the patient. In some variations, the visualization enhancers can be disposed remote from the delivery system and/or can be configured to enhance visualization enhancers disposed on the delivery system.

With the provision of a visualization of the detected subcutaneous structures, the physician can assess the position of subcutaneous structures such as the internal thoracic artery, or other structures, of the body while concurrently inserting components of the delivery system into the body, while avoiding those subcutaneous structures.

In some variations, during advancement of lead 802 through the intercostal space associated with the cardiac notch, sensor(s) 810 can be configured to transmit obtained readings to a computing device for interpretation. In some variations, the computing device is pulse generator 102. In some variations, pulse generator 102 is used to transmit the readings to an external computing device for interpretation. In any event, the sensor information from the various sensors can be used individually, or accumulatively, to determine the location of the distal end of lead 802.

Figure 10:
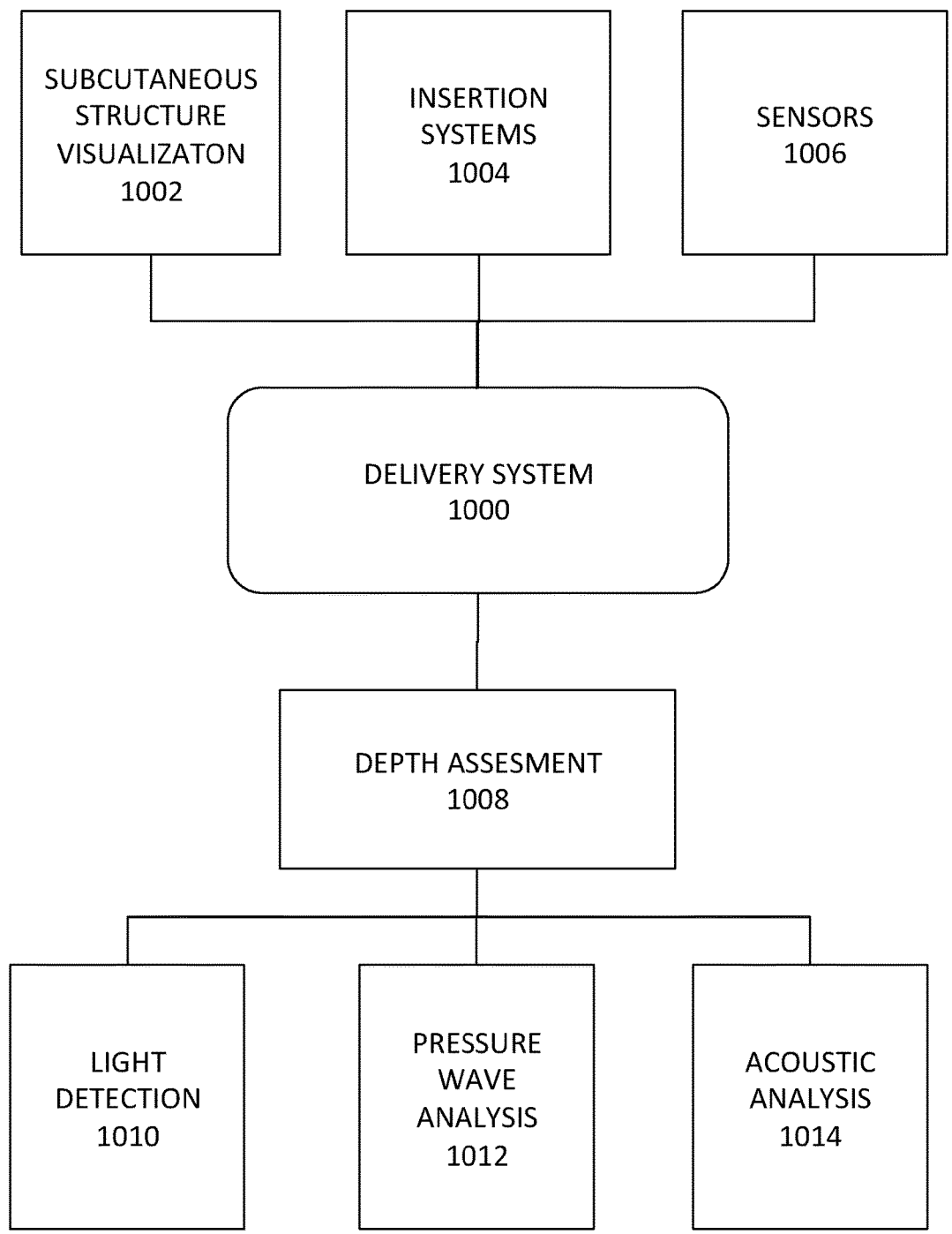
FIG. 10 is a schematic illustration of an exemplary delivery control system having features consistent with the current subject matter.

FIG. 10 is a schematic illustration of a delivery control system 1000 having features consistent with the current subject matter. The delivery control system 1000 can be configured to automatically deliver a lead to the desired position within the patient. For example, the delivery control system 1000 can be configured to automatically deliver a distal tip of a lead through the intercostal space associated with the cardiac notch.

Delivery control system 1000 can be configured to receive a plurality of inputs. The inputs can come from one or more sensors disposed in, or on, the patient. For example, delivery control system 1000 can be configured to receive subcutaneous structure visualization information 1002, information associated with delivery insertion systems 1004, information associated with sensors 1006, and the like.

Delivery control system 1000 can be configured to use remote sensors 1006 to facilitate determination of the insertion site for the lead. Sensors 1006 can be disposed in various instruments configured to be inserted into the patient. Sensors 1006 can also be disposed in various instruments configured to remain external to the patient.

Delivery control system 1000 can be configured to perform depth assessments 1008. The depth assessments 1008 can be configured to determine the depth of the distal end of an inserted instrument, such as a lead 802 illustrated in FIG. 8A. Depth assessments 1008 can be configured to determine the depth of the distal end of the inserted instrument through light detection systems 1010, pressure wave analysis 1012, acoustic analysis, and the like.

Depth assessments 1008 can be configured to determine the depth of the delivery system, or lead, though pressure wave analysis systems 1012. Pressure waves can be detected by accelerometers as herein described.

Depth assessments 1008 can be configured to determine the depth of the delivery system though acoustic analysis systems 1014. Acoustic analysis system 1014 can be configured to operate in a similar manner to a stethoscope. The acoustic analysis system 1014 can be configured to detect the first heart sound (S1), the second heart sound (S2), or other heart sounds. Based on the measurements obtained by the acoustic analysis system 1014, a depth and/or location of the distal end of a delivery system and/or inserted medical component can be determined. The acoustic analysis system 1014 can be configured to measure the duration, pitch, shape, and tonal quality of the heart sounds. By comparing the duration, pitch, shape, and tonal quality of the heart sounds with known models, a determination or verification of the location of the lead can be made. Sudden changes in the degree of heart sounds may be used to indicate advancement into a new tissue plane.

In some variations, the lead can include markers or sensors that facilitate the correct placement of the lead. Certain markers such as a visual scale, radiopaque, magnetic, ultrasound markers, and the like, can be position at defined areas along the length of the lead so that the markers can be readily observed by an implanting physician, or automated system, on complementary imaging instruments such as fluoroscopy, x-ray, ultrasound, or other imaging instruments known in the art. Through the use of these markers, the physician, or automated implantation device, can guide the lead to the desired location within the intercostal muscle, pleural space, mediastinum, or other desired position, as applicable.

Figure 11A:
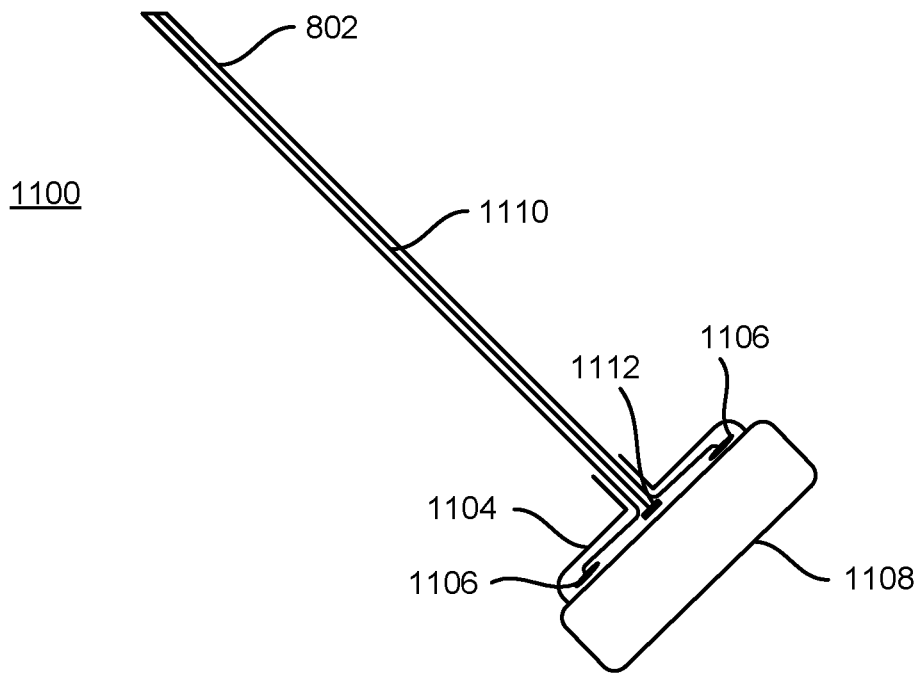
FIGS. 11A and 11B are illustrations of an exemplary lead having features consistent with the current subject matter.
Figure 11B:
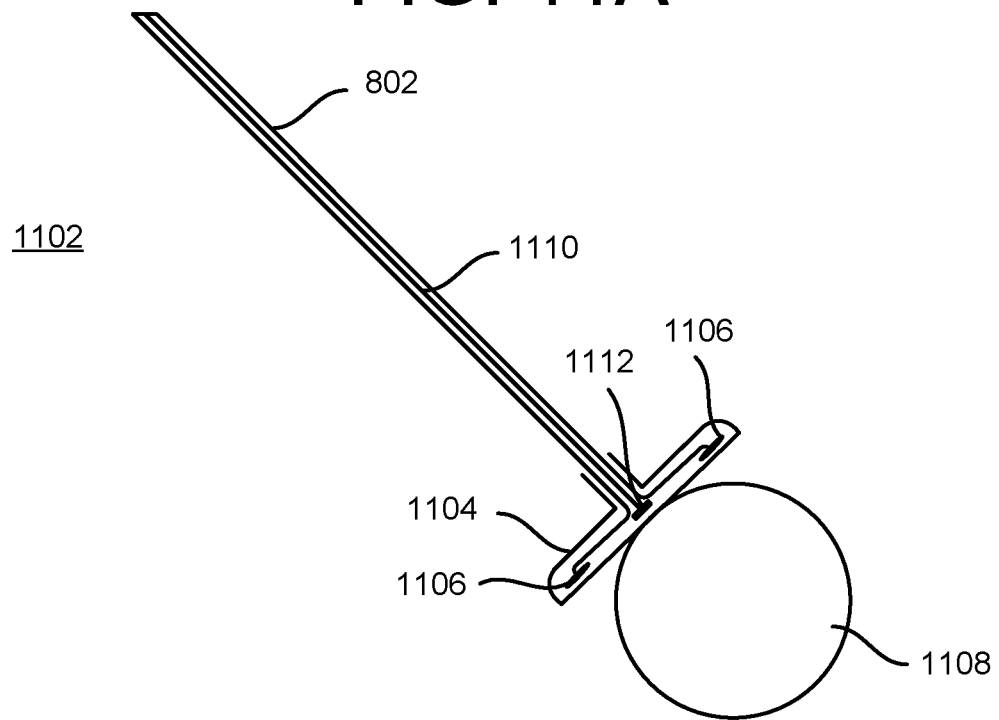

Avoiding damage to tissues in the vicinity of the path-of-travel for the lead is important. Moving various tissues from the path of the lead without damaging them is also important. FIGS. 11A and 11B are illustrations 1100 and 1102 of an exemplary lead 802 having features consistent with the present disclosure for moving and avoiding damage to tissues during lead delivery. Lead 802 can comprise a distal tip 1104. Distal tip 1104 can include at least one electrode and/or sensor 1106.

Having leads directly touch the tissue of a patient can be undesirable and can damage the tissue. Consequently, the distal tip 1104 of lead 802 can include an inflatable balloon 1108. Balloon 1108 can be inflated when the distal tip 1104 of lead 802 encounters an anatomical structure obstructing its path, or prior to moving near sensitive anatomy during lead delivery. The balloon may be configured to divert the obstacle and/or the lead to facilitate circumventing the anatomical structure or may indicate that the lead has reached its intended destination.

To inflate the balloon, lead 802 can include a gas channel 1110. At the end of gas channel 1110 there can be a valve 1112. Valve 1112 can be controlled through physical manipulation of a valve actuator, through electrical stimulation, through pressure changes in gas channel 1110 and/or controlled in other ways. In some variations, the valve 1112 may be configured at the proximal end of the lead 802.

When positioning lead 802 into a patient, lead 802 may cause damage to, or perforations of, the soft tissues of the patient. When lead 802 is being installed into a patient, distal tip 1104 of lead 802 can encounter soft tissue of the patient that should be avoided. In response to encountering the soft tissue of the patient, gas can be introduced into gas channel 1110, valve 1112 can be opened and balloon 1108 can be inflated, as shown in FIG. 11B. Inflating balloon 1108 can cause the balloon to stretch and push into the soft tissue of the patient, moving the soft tissue out of the way and/or guiding distal tip 1104 of lead 802 around the soft tissue. When distal tip 1104 of lead 802 has passed by the soft tissue obstruction, valve 1112 can be closed and the balloon deflated.

Figure 12:
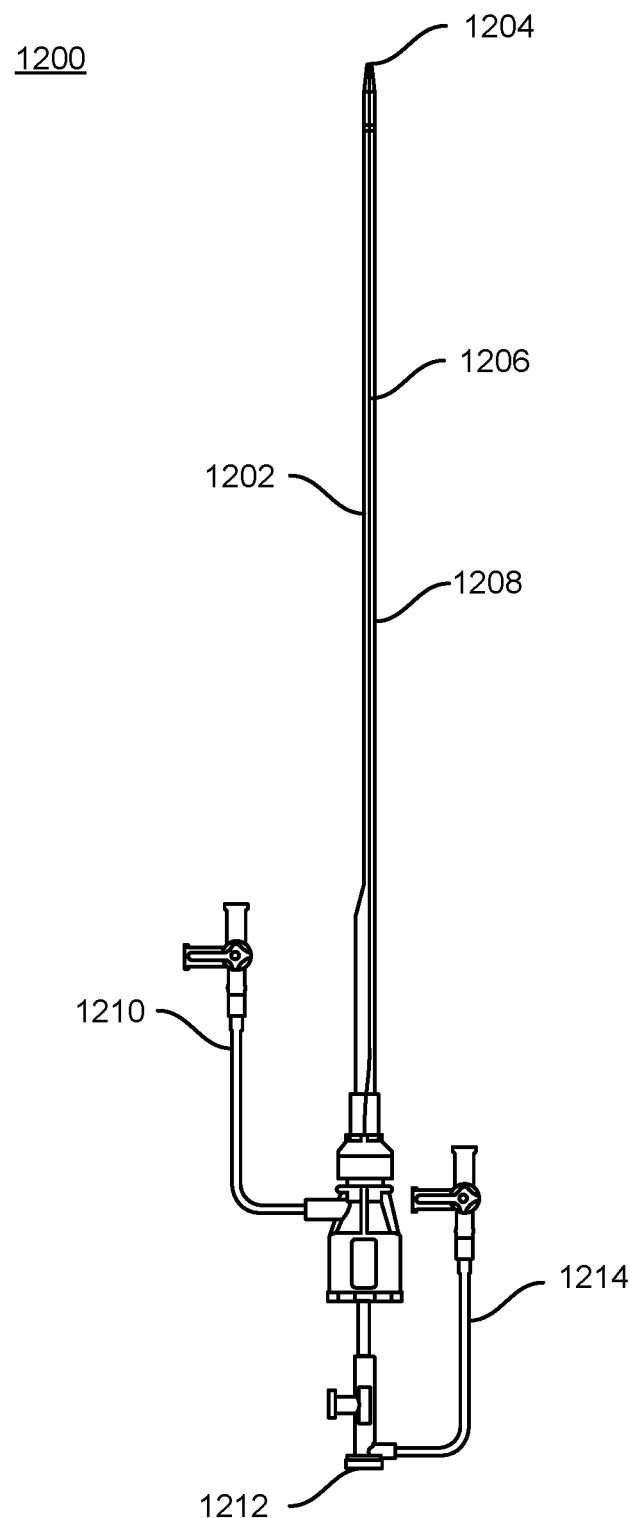
FIG. 12 is an illustration of an exemplary sheath for delivering a lead, the sheath having features consistent with the current subject matter.

In some variations, a delivery component or system is used to facilitate delivery of a lead, such as lead 802, to the desired location. FIG. 12 is an illustration 1200 of an exemplary delivery system for a lead having features consistent with the present disclosure. An example of the delivery system is an expandable sheath 1202. Expandable sheath 1202 can be inserted into the patient at the desired insertion point, identified using one or more of the technologies described herein. Expandable sheath 1202 can include a tip 1204. In some variations, tip 1204 may be radiopaque. A radiopaque tip 1204 may be configured to facilitate feeding of the expandable sheath 1202 to a desired location using one or more radiography techniques known in the art and described herein. Such radiography techniques can include fluoroscopy, CT scan, and the like.

Tip 1204 can include one or more sensors for facilitating the placement of the lead. The sensors included in tip 1204 of the expandable sheath 1202 can be the same or similar to the sensors described herein for monitoring physiological characteristics of the body and other characteristics for facilitating positioning of a lead in a body.

Expandable sheath 1202 can include a channel 1206 running through a hollow cylinder 1208 of expandable sheath 1202. When tip 1204 of expandable sheath 1202 is at the desired location, gas or liquid can be introduced into hollow cylinder 1208. The gas or liquid can be introduced into hollow cylinder 1208 through a first port 1210. Hollow cylinder 1208 can expand, under the pressure of the gas or liquid, causing channel 1206 running through hollow cylinder 1208 to increase in size. A lead, such as lead 802 illustrated in FIG. 8A, can be inserted into channel 1206 through a central port 1212. Hollow cylinder 1208 can be expanded until channel 1206 is larger than the lead. In some variations, channel 1206 can be expanded to accommodate leads of several French sizes. Once the lead is in the desired place, expandable sheath 1202 can be removed, by allowing the lead to pass through channel 1206. In some variations, liquid or gas can be introduced into or removed from channel 1006 through a second port 1214.

Using expandable sheath 1202 can provide an insertion diameter smaller than the useable diameter. This can facilitate a reduction in the risk of damage to tissues and vessels within the patient when placing the lead.

When electricity is brought within the vicinity of muscle tissue, the muscle will contract. Consequently, having a lead for carrying electrical pulses traversing through intercostal muscle tissue may cause the intercostal muscle tissue to contract. Electrical insulation can be provided in the form of a receptacle disposed in the intercostal muscle, where the receptacle is configured to electrically insulate the intercostal muscle from the lead.

Figure 13:
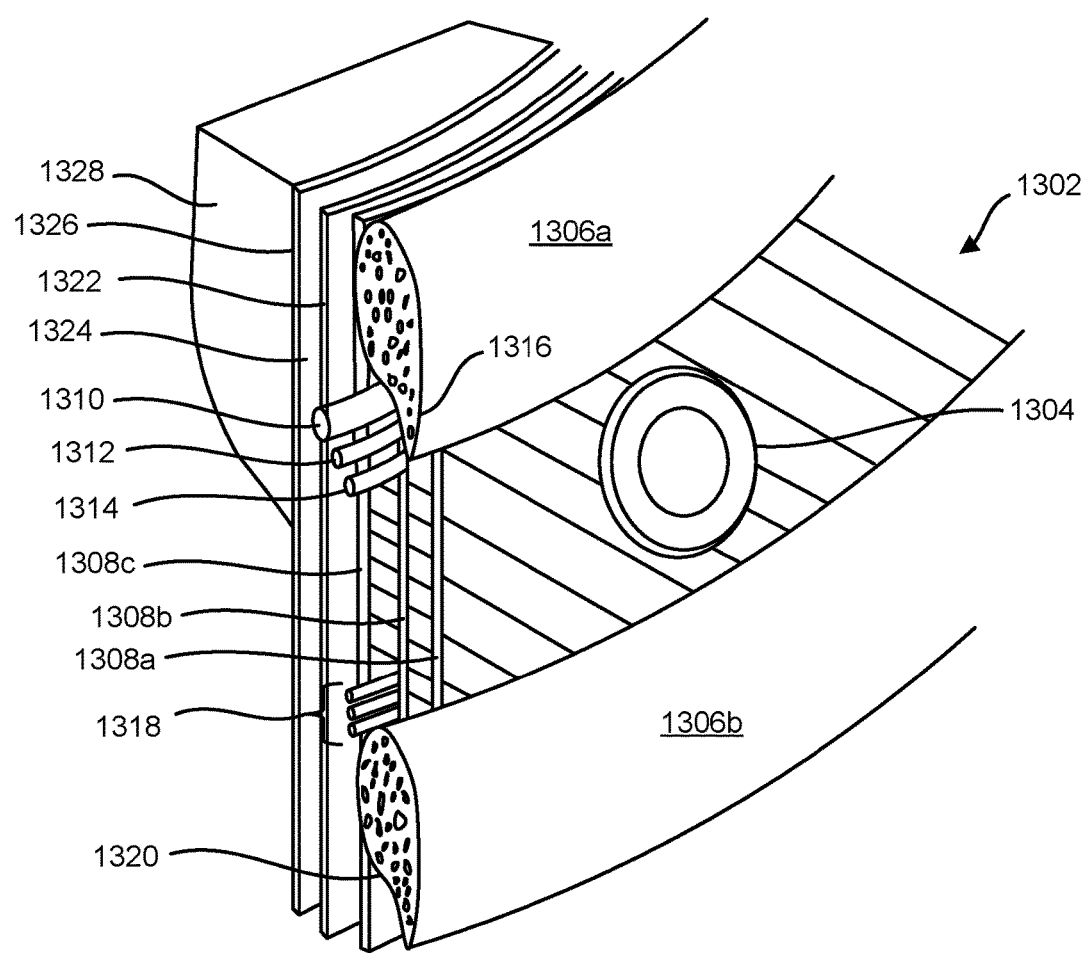
FIG. 13 is an illustration of an intercostal space associated with the cardiac notch of the left lung with an exemplary lead fixation receptacle having features consistent with the current subject matter inserted therein.

FIG. 13 is an illustration 1300 of an intercostal space 1302 associated with the cardiac notch of the left lung with an exemplary lead receptacle 1304 having features consistent with the present disclosure. Lead receptacle 1304 can facilitate the placement of leads, and/or other instruments and avoid the leads and/or instruments physically contacting the intercostal tissue. When the distal end of the lead is positioned to terminate in the intercostal muscle, the lead can be passed through lead receptacle 1304 that has been previously placed within the patient's intercostal muscles. Lead receptacle 1304 can be configured to be electrically insulated so that electrical energy emanating from the lead will not stimulate the surrounding intercostal and skeletal muscle tissue, but will allow the electrical energy to traverse through and stimulate cardiac tissue.

The intercostal space 1302 is the space between two ribs, for example, rib 1306*a* and rib 1306*b*. Intercostal muscles 1308*a*, 1308*b* and 1308*c* can extend between two ribs 1306*a* and 1306*b*, filling intercostal space 1302. Various blood vessels and nerves can run between the different layers of intercostal muscles. For example, intercostal vein 1310, intercostal artery 1312, the intercostal nerve 1314 can be disposed under a flange 1316 of upper rib 1306*a* and between the innermost intercostal muscle 1308*c* and its adjacent intercostal muscle 1308*b*. Similarly, collateral branches 1318 can be disposed between the innermost intercostal muscle 1308*c* and its adjacent intercostal muscle 1308*b*.

The endothoracic facia 1320 can abut the inner-most intercostal muscle 1308*c* and separate the intercostal muscles from the parietal pleura 1322. The pleural cavity 1324 can be disposed between the parital pleura 1322 and the visceral pleura 1326. The visceral pleura 1326 can abut the lung 1328.

Figure 14:
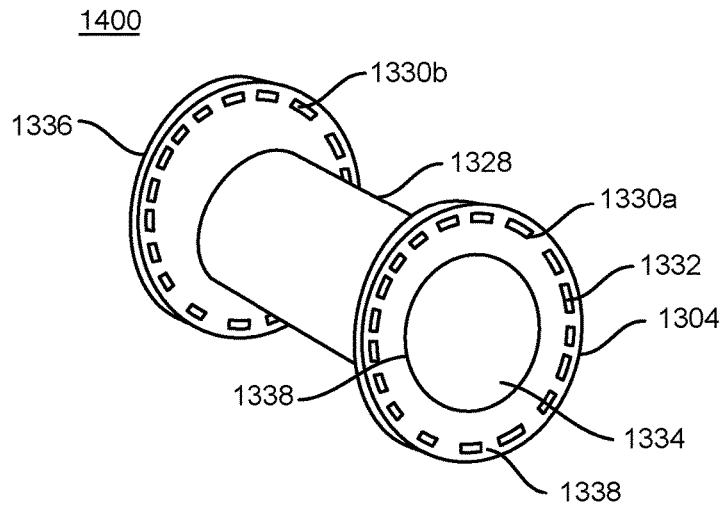
FIG. 14 is an illustration of an exemplary lead fixation receptacle having features consistent with the current subject matter.

FIG. 14 is an illustration 1400 of an exemplary lead fixation receptacle 1304 illustrated in FIG. 13, having features consistent with the present disclosure.

Lead receptacle 1304 may comprise a cylindrical body, or lumen 1328, from an outer side of an outermost intercostal muscle to an inner side of an innermost intercostal muscle of an intercostal space. Lumen 1328 may be configured to support a lead traversing through it. Lumen 1328 may comprise an electrically insulating material configured to inhibit traversal of electrical signals through walls of lumen 1328. In some variations, end 1336 of the receptacle 1304 may pass through the innermost intercostal muscle 1308*c*. In some variations, end 1338 of receptacle 1304 can pass through outermost intercostal muscle 1308*a*.

Lumen 1328 can terminate adjacent the pleural space 1324. In some variations, the lumen 1328 can terminate in the mediastinum. In some variations, receptacle 1304 can be configured to be screwed into the intercostal muscles 1308*a*, 1308*b*, and 1308*c*. Receptacle 1304 can also be configured to be pushed into the intercostal muscles 1308*a*, 1308*b* and 1308*c*.

Lead receptacle 1304 may include a fixation flange 1330*a*. Fixation flange 1330*a* may be disposed on the proximal end of the lumen 1328 and configured to abut the outermost intercostal muscle 1308*a*. Lead receptacle 1304 may include a fixation flange 1330*b*. Fixation flange 1330*b* can be disposed on the distal end of the lumen 1328 and configured to abut the outermost intercostal muscle 1308*c*. Lead receptacle 1304 can be implanted into the intercostal muscles 1308*a*, 1308*b*, and 1308*c* by making an incision in the intercostal muscles 1308*a*, 1308*b*, and 1308*c*, stretching the opening and positioning lead receptacle 1304 into the incision, taking care to ensure that the incision remains smaller than the outer diameter of flanges 1330*a* and 1330*b*. In some variations flanges 1330*a* and 1330*b* can be configured to be retractable allowing for removal and replacement of the lead fixation receptacle 1304.

Lead receptacle 1304 can be fixed in place by using just flanges 1330*a* and 1330*b*. Lead receptacle 1304 may also be fixed in place by using a plurality of surgical thread eyelets 1332. Surgical thread eyelets 1332 can be configured to facilitate stitching lead receptacle 1304 to the intercostal muscles 1308*a* and 1308*c* to fix lead receptacle 1304 in place.

Receptacle 1304 can include an internal passage 1334. Internal passage 1334 can be configured to receive one or more leads and facilitate their traversal through the intercostal space 1302.

Lead receptacle 1304 can be formed from an electrically insulating material. The electrically insulating material can electrically isolate the intercostal muscles 1308*a*, 1308*b* and 1308*c* from the leads traversing through lead receptacle 1304.

Lead receptacle 1304 can be formed from materials that are insulative. The material can include certain pharmacological agents. For example, antibiotic agents, immunosuppressive agents to avoid rejection of lead receptacle 1304 after implantation, and the like. In some variations, lead receptacle 1304 can be comprised of an insulative polymer coated or infused with an analgesic. In some variations, the lead receptacle 1304 can be comprised of an insulative polymer coated or infused with an anti-inflammatory agent. The polymer can be coated or infused with other pharmacological agents known to one skilled in the art to treat acute adverse effects from the implantation procedure or chronic adverse effects from the chronic implantation of the lead or receptacle within the thoracic cavity.

Figure 15:
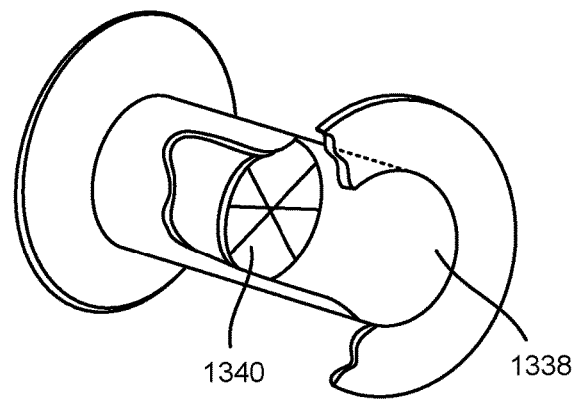
FIG. 15 is an illustration of an exemplary lead fixation receptacle having features consistent with the current subject matter.

FIG. 15 is an illustration of lead receptacle 1304 having features consistent with the present disclosure. Lead fixation receptacle can comprise a septum 1340, or multiple septums disposed traversely within lumen 1338. Septum 1340 can be selectively permeable such that when a lead is inserted through septum 1340, septum 1340 can be configured to form a seal around the lead traversing through lumen 1338 to prevent the ingress or egress of gas, fluid, other materials, and the like, through lumen 1338. Septum 1340 may optionally permit the egress of certain gas and fluid but prevent ingress of such materials through lumen 1338.

In some variations, the lead receptacle can comprise multiple lumens. For example, lead receptacle can comprise a second lumen configured to traverse from an outermost side of an outermost intercostal muscle to an innermost side of an innermost intercostal muscle. Second lumen can be configured to facilitate dispensing of pharmacological agents into the thorax of the patient.

The lumens for such a lead receptacle can be used for differing purposes in addition to the passage of a single lead into the pleural space or mediastinum. The multiple lumens can provide access for multiple leads to be passed into the pleural space or mediastinum.

Figure 16:
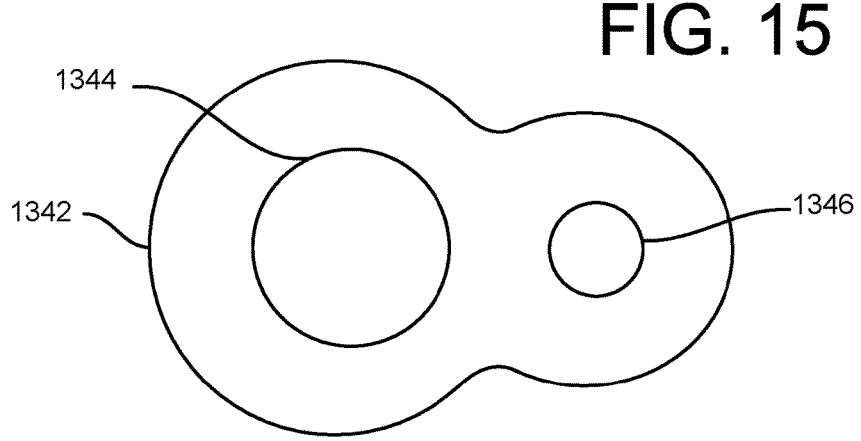
FIG. 16 is an illustration of an exemplary lead fixation receptacle having features consistent with the current subject matter.

FIG. 16 is an illustration of an exemplary lead fixation receptacle 1342 having features consistent with the present disclosure. Lead fixation receptacle 1342 can include a first lumen 1344, similar to lumen 1338 of the lead receptacle 1304 illustrated in FIGS. 14 and 15. Lead fixation receptacle 1342 can include an additional lumen 1346. Additional lumen 1346 can be provided as a port to provide access to the thoracic cavity of the patient. Access can be provided to facilitate dispensing of pharmacological agents, such as pharmacological agents to treat various adverse effects such as infection or pain in the area surrounding lead receptacle 1342, pleural space, mediastinum, and/or other areas surrounding the thoracic cavity of the patient. Additional lumen 1346 can provide access for treatment of other diseases or disorders affecting organs or other anatomical elements within the thoracic cavity. For example, additional lumen 1346 can facilitate the evacuation of gas or fluid from the thorax, and the like.

The lead receptacle as described with reference to FIGS. 13-16 can be fixated to cartilage, or bone within the thoracic cavity. In some variations, the lead receptacle can be configured to be disposed between the intercostal muscles and a rib, thereby potentially reducing damage to the intercostal muscles caused by its insertion. The lead receptacle can be in passive contact with tissue surrounding the cardiac notch. For example, the lead receptacle can abut the superficial facia on the outermost side and the endothoracic facia or the parietal pleura on the innermost side.

In some variations, the lead receptacle can be actively fixed into position using one end of the lead receptacle. For example, only one flange can include surgical thread holes to facilitate sewing of the flange into the intercostal muscles.

Active fixation, whether at flanges, or along the lumen of the lead fixation receptacle, can include, for example, the use of tines, hooks, springs, screws, flared wings, flanges and the like. Screws can be used to screw the lead fixation receptacle into bone or more solid tissues within the thoracic cavity. Hooks, tines, springs, and the like, can be used to fix the lead fixation receptacle into soft tissues within the thoracic cavity.

In some variations the lead receptacle can be configured to facilitate in-growth of tissue into the material of which the lead fixation receptacle is comprised. For example, the lead fixation receptacle can be configured such that bone, cartilage, intercostal muscle tissue, or the like, can readily grow into pockets or fissures within the surface of the lead receptacle. Facilitating the growth of tissue into the material of the lead receptacle can facilitate fixation of the receptacle.

In some variations, the receptacle can be configured to actively fix between layers of the intercostal muscle. With reference to FIG. 13, the layered nature of the intercostal muscle layers 1308a, 1308b and 1308c can be used to facilitate fixation of the lead receptacle into the intercostal space. For example, flanges can be provided that extend between the intercostal muscle layers. Incisions can be made at off-set positions at each layer of intercostal muscle such that when the lead receptacle is inserted through the incisions, the intercostal muscles apply a transverse pressure to the lead receptacle keeping it in place. For example, a first incision can be made in the first intercostal muscle layer 1308a, a second incision can be made in the second intercostal muscle layer 1308b, offset from the first incision, and a third incision can be made to the third intercostal muscle layer 1308c in-line with the first incision. Inserting the lead receptacle through the incisions, such that the lead receptacle is situated through all three incisions, will cause the second intercostal muscle layer 1308b to apply a transverse pressure to the lead receptacle that is countered by the first intercostal muscle layer 1308a and the third intercostal muscle layer 1308c, facilitating keeping the lead receptacle in place.

A pulse generator, such as pulse generator 102 illustrated in FIG. 1, can be configured to monitor physiological characteristics and physical movements of the patient. Monitoring can be accomplished through sensors disposed on, or in, the pulse generator, and/or through sensors disposed on one or more leads disposed within the body of the patient. The pulse generator can be configured to monitor physiological characteristics and physical movements of the patient to properly detect heart arrhythmias, dyssynchrony, and the like.

Sensor(s) can be configured to detect an activity of the patient. Such activity sensors can be contained within or on the housing of the pulse generator, such as pulse generator 102 illustrated in FIG. 1. Activity sensors can comprise one or more accelerometers, gyroscopes, position sensors, and/or other sensors, such as location-based technology, and the like. Sensor information measured by the activity sensors can be cross-checked with activity information measured by any concomitant devices.

In some variations, an activity sensor can include an accelerometer. The accelerometer can be configured to detect accelerations in any direction in space. Acceleration information can be used to identify potential noise in signals detected by other sensor(s), such as sensor(s) configured to monitor the physiological characteristics of the patient, and the like, and/or confirm the detection of signals indicating physiological issues, such as arrhythmias or other patient conditions.

In some variations, a lead, such as lead 802 in FIG. 8, can be configured to include sensors that are purposed solely for monitoring the patient's activity. Such sensors may not be configured to provide additional assistance during the implantation procedure. These sensors can include pulmonary, respiratory, minute ventilation, accelerometer, hemodynamic, and/or other sensors. Those sensors known in the art that are used to real-time, or periodically monitor a patient's cardiac activity can be provided in the leads. These sensors are purposed to allow the implanted device to sense, record and in certain instances, communicate the sensed data from these sensors to the patient's physician. In alternative embodiments, the implanted medical device may alter the programmed therapy regimen of the implanted medical device based upon the activity from the sensors.

In some variations, sensors, such as sensors 810 and 812 of FIG. 8A, may be configured to detect the condition of various organs and/or systems of the patient. Sensor(s) 810, 812 can be configured to detect movement of the patient to discount false readings from the various organs and/or systems. Sensor(s) 810, 812 can be configured to monitor patient activity. Having a distal end 806 of lead 802 positioned in the cardiac notch abutting the parietal pleura, sensor(s) 810, 812 can collect information associated with the organs and/or systems of the patient in that area, for example the lungs, the heart, esophagus, arteries, veins and other organs and/or systems. Sensor(s) 810 can include sensors to detect cardiac ECG, pulmonary function, sensors to detect respiratory function, sensors to determine minute ventilation, hemodynamic sensors and/or other sensors. Sensors can be configured independently to monitor several organs or systems and/or configured to monitor several characteristics of a single organ simultaneously. For example, using a first sensor pair, the implanted cardiac pacing system may be configured to monitor the cardiac ECG signal from the atria, while simultaneously, a second sensor pair is configured to monitor the cardiac ECG signal from the ventricles.

A lead disposed in the body of a patient, such as lead 802 of FIG. 8A, can include sensors at other areas along the lead, for example, sensors 812. The location of sensors 812 along lead 802 can be chosen based on proximity to organs, systems, and/or other physiological elements of the patient. The location of sensors 812 can be chosen based on proximity to other elements of the implanted cardiac pacing system.

Additional leads may be used to facilitate an increase in the sensing capabilities of the implantable medical device. In one embodiment, in addition to at least one lead disposed within the intercostal muscle, pleural space or mediastinum, another lead is positioned subcutaneously and electrically connected to the implantable medical device. The subcutaneously placed lead can be configured to enhance the implantable medical device's ability to sense and analyze far-field signal's emitted by the patient's heart. In particular, the subcutaneous lead enhances the implantable medical device's ability to distinguish signals from particular chambers of the heart, and therefore, appropriately coordinate the timing of the required pacing therapy delivered by the implantable medical device.

Additional leads in communication with the implantable medical device or pulse generator, and/or computing device, can be placed in other areas within the thoracic cavity in order to enhance the sensing activity of the heart, and to better coordinate the timing of the required pacing therapy delivered by the implantable medical device. In certain embodiments, these additional leads are physically attached to the implantable medical device of the present disclosure.

The leads used to deliver therapeutic electrical pulses to pace the heart can comprise multiple poles. Each pole of the lead can be configured to deliver therapeutic electrical pulses and/or obtain sensing information. The different leads can be configured to provide different therapies and/or obtain different sensing information. Having multiple sensors at multiple locations can increase the sensitivity and effectiveness of the provided therapy.

Figure 8B:
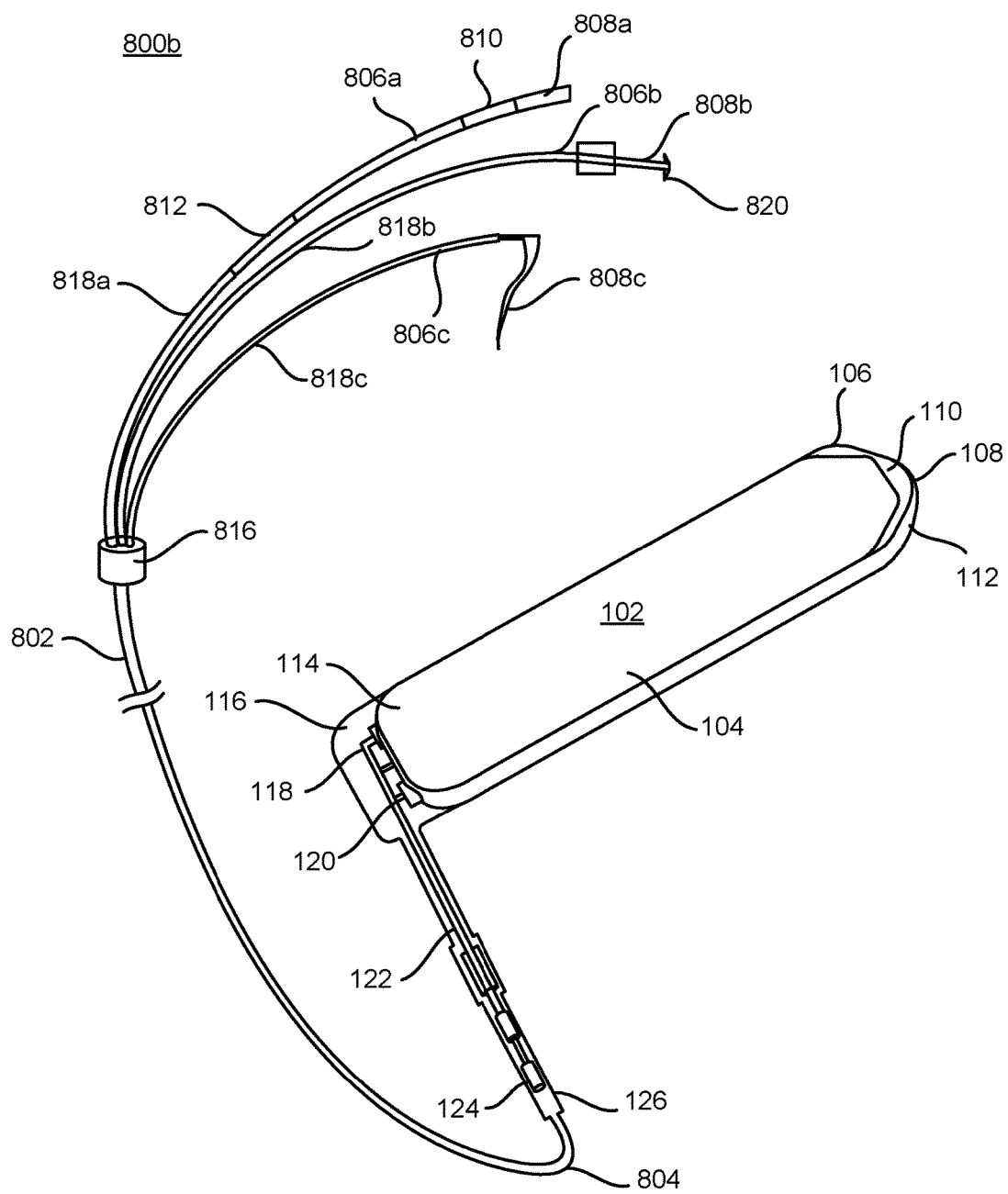
FIG. 8B is an illustration of an exemplary lead having features consistent with the current subject matter.

FIG. 8B is an illustration 800b of an exemplary lead 802 having features consistent with the present disclosure. In some variations, lead 802 can comprise a yoke 816. The yoke can be configured to maintain a hermetically sealed housing for the internal electrical cables of lead 802, while facilitating splitting of the internal electrical cables into separate end-leads 818a, 818b, 818c. Yoke 816 can be disposed toward distal end of lead 802. While three end-leads 818a, 818b, 818c are illustrated in FIG. 8B, the current disclosure contemplates fewer end-leads as well as a greater number of end-leads emanating from yoke 816.

The different end-leads 818a, 818b, 818c, can include different electrodes and/or sensors. For example, end-lead 818b can include an electrode 808b at the distal end 806b of end-lead 818b that differs from electrode 808a at distal end 806a of end-lead 818a. Electrode 808b can have flanges 820. Flanges 820 can be configured to act as an anchor, securing the distal end 806b of end-lead 818b in position within the patient. Electrode 808b with flanges 820 can be suitable for anchoring into high-motion areas of the body where end-lead 818b would otherwise move away from the desired location without the anchoring effect provided by flanges 820. Similarly, electrode 808c at the distal end 806c of end-lead 818c can be configured for a different function compared to the electrodes at the end of other end-leads.

Lead 802 can be a multi-pole lead. Each pole can be electronically isolated from the other poles. The lead 802 can include multiple isolated poles, or electrodes, along its length. The individual poles can be selectively activated. The poles may include sensors for monitoring cardiac or other physiological conditions of the patient, or electrodes for deliver therapy to the patient.

The sensing characteristics of a patient can change over time, or can change based on a patient's posture, a multi-pole lead permits the implantable medical device facilitate monitoring a patient's state through multiple sensing devices, without requiring intervention to reposition a lead. Furthermore, a multi-pole lead can be configured to facilitate supplementary sensing and therapy delivery vectors, such as sensing or stimulating from one pole to a plurality of poles, sensing or stimulating from a plurality of poles to a single pole, or sensing or stimulating between a plurality of poles to a separate plurality of poles. For example, should one particular vector be ineffective at treating a particular arrhythmia, the implantable medical device, or pulse generator, can be configured to switch vectors between the poles on the lead and reattempt therapy delivery using this alternative vector. This vector switching is applicable for sensing. Sensing characteristics can be monitored, and if a sensing vector becomes ineffective at providing adequate sensing signals, the implantable medical device can be configured to switch vectors or use a combination of one or more sensor pairs to create a new sensing signal.

In some variations, at yoke 816, each of the poles of the multi-pole lead can be split into their separate poles. Each of the end-leads emanating from the yoke 816 can be associated with a different pole of the multi-pole lead.

Some of the end-leads emanating from yoke 816 can be configured for providing sensor capabilities of and/or therapeutic capabilities to the patient's heart. Others of the end-leads emanating from yoke 816 can be configured to provide sensor capabilities and/or therapeutic capabilities that are unrelated to the heart. Similarly, the cardiac pacing system herein described can include leads 802, or medical leads, that provide functionality unrelated to the heart.

In some variations, the lead can be bifurcated. A bifurcated lead can comprise two cores within the same lead. In some variations, the different cores of the bifurcated lead can be biased to bend in a predetermined manner and direction upon reaching a cavity. Such a cavity can, for example, be the mediastinum. Bifurcated lead cores can be comprised of shape memory materials, for example, nitinol or other material known in the art to deflect in a predetermined manner upon certain conditions. The conditions under which the bifurcated lead cores will deflect include electrical stimulation, pressure, temperature, or other conditions. In some variations, each core of the bifurcated lead can be configured so that it is steerable by the physician, or an automated system, to facilitate independent advancement of each core of the bifurcated lead, in different directions.

A pacemaker of the kinds contemplated by the present disclosure can comprise one or more sensors configured to monitor the activity of the atrial or ventricular chambers of the patient's heart, methods to filter and prepare these sensor signals for use by downstream algorithms, methods to trigger heartbeat detections or detections of other physiologic activity from these signals, methods to authenticate the accuracy of such cardiac or physiologic detections and methods to prepare for, and control pacing therapy.

Figure 17A:
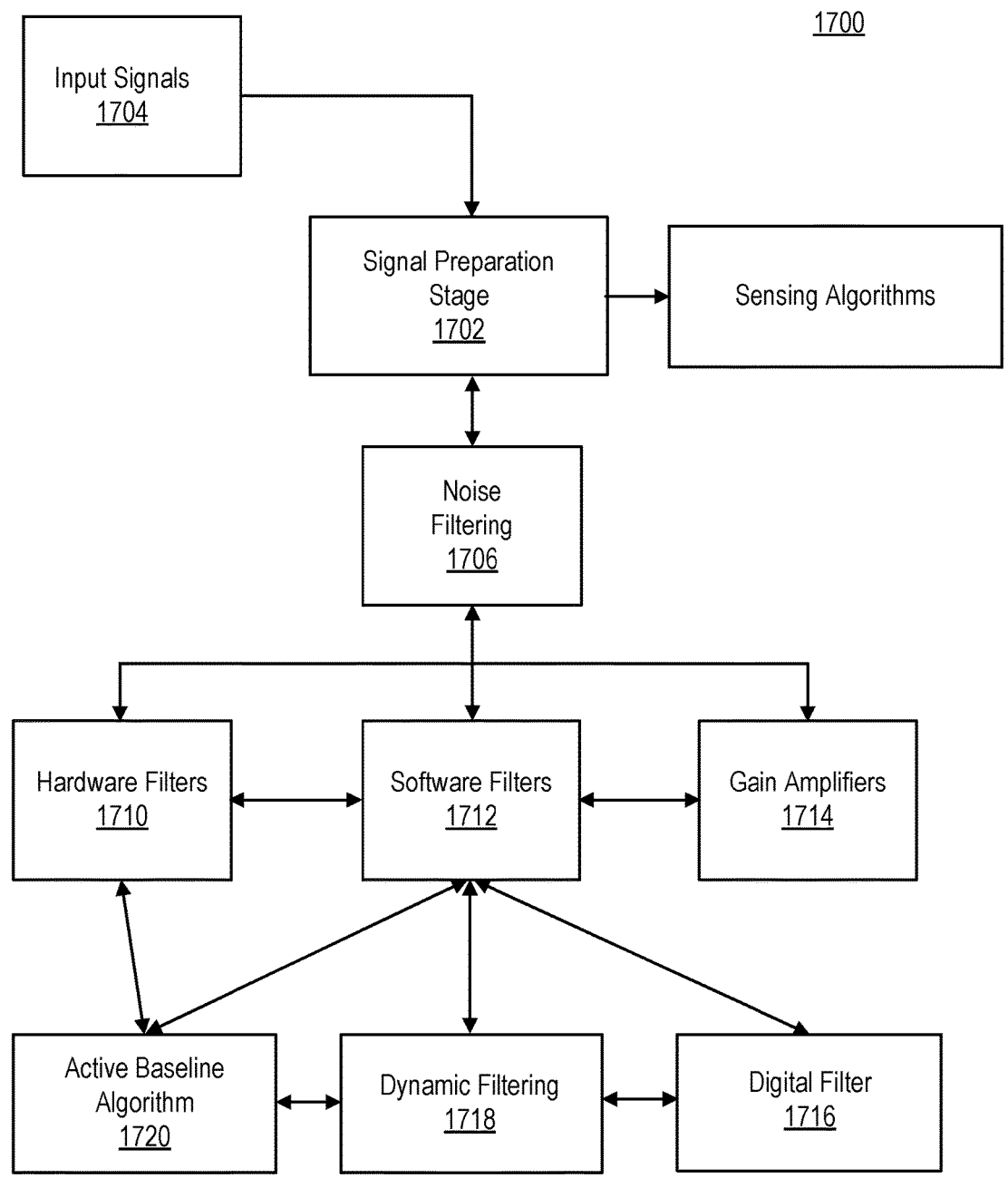
FIGS. 17A and 17B are illustrations of an exemplary data flow for sensing signals and signal preparation for cardiac therapy having features consistent with the present disclosure.
Figure 17B:
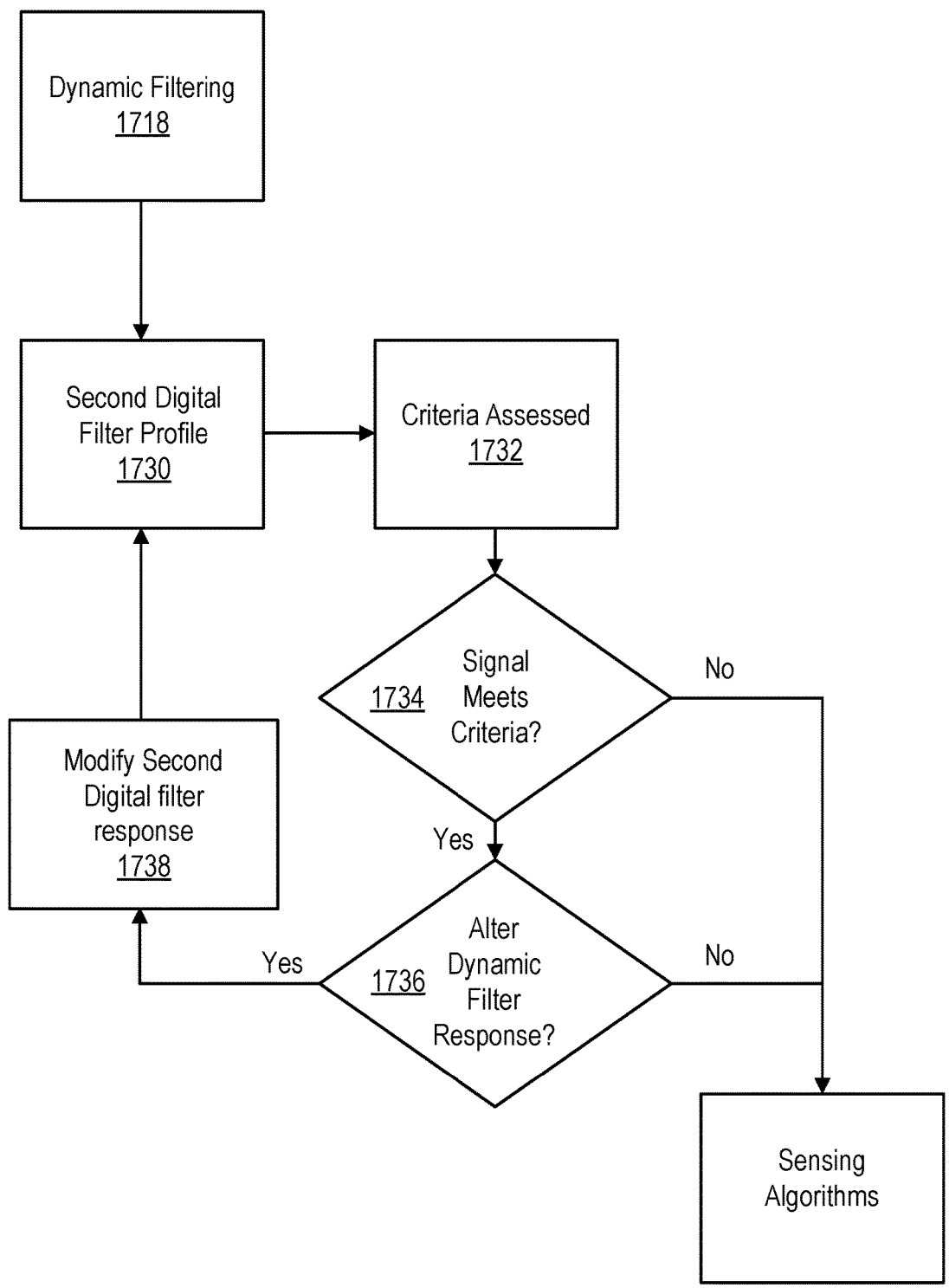

FIGS. 17A and 17B are illustrations showing an exemplary data flow 1700 for sensing signals and signal preparation for cardiac therapy having features consistent with the current subject matter. Data flow 1700 can be employed by a cardiac pacing system, such as the cardiac pacing systems described herein. The cardiac pacing system can include a pacemaker, such as pulse generator 102 illustrated in FIG. 1, pacing leads, such as leads 802 illustrated in FIG. 8, and/or other components. The cardiac pacing system can include sensor leads having one or more sensors configured to monitor physiological characteristics of the patient. Sensing leads disposed in or adjacent to the cardiac notch of the patient can be effective at monitoring the physiological characteristics in the vicinity of the cardiac notch such as the patient's electrocardiogram, respiration, blood oximetry, temperature, and the like. Sensing leads that include an accelerometer can be used to detect the patient's posture, the functioning of the cardiac or skeletal muscles and other physical characteristics monitored by an accelerometer.

A cardiac pacing system can comprise a pulse generator configured to monitor physiological characteristics of a patient. The pulse generator can deliver therapeutic electrical pulses through an electrode to regulate a heartbeat of a patient in response to certain conditions being detected in the monitored physiological characteristics of a patient. To monitor the physiological characteristics of a patient, a sensor(s) can be provided in the patient, from which the pulse generator can receive information associated with the physiological characteristics of the patient. However, the sensors not only obtain measurements associated with physiological characteristics of the patient, the sensors also capture noise from exogenous or endogenous sources and signals unrelated to the monitored physiological characteristics. Consequently, the pulse generator can be configured to filter out, or normalize, the noise and signals.

Signal preparation 1702 prepares the sensing signals for use by the downstream system/algorithms. This stage is primarily focused on the signals used for sensing, not the vector used for pacing. The signal preparation stage 1702 can take all of the available input signals 1704 from the system (e.g., ECG pairs, respiration, blood oximetry, etc.), apply filters to these signals 1706, identify noise contained within these signals, determine which signals are acceptable for use and then select the preferred signals for downstream sensing algorithms. The signal preparation stage can continually monitor all of the signals to determine if changes to the selected signal are required.

There are many sources of noise that can interfere with the quality of the signal being sensed by the cardiac pacing system. For example, noise can be generated from the patient's own muscle tissue. When a patient flexes a muscle, signals caused by, for example, electrical waves, pressure waves, temperature changes, and the like, can be detected by the sensors associated with a cardiac pacing system. Another example of noise that can cause a distortion in the signals being received by the cardiac pacing system is radio frequency interference. Radio frequency interference can come from the components of the cardiac pacing system itself, from other components within the body, from external sources such as cell phones, electrical cables, and the like. The effect of these signals, or noise, can be accounted for by filtering.

The cardiac pacing system, configured to monitor the patient's heart, can include hardware filters 1710, software filters 1712 and gain amplifiers 1714 for filtering out the noise or interference signals 1706 detected by sensors of the cardiac pacing system. The filtering 1706 can be applied in series or become a product of multiple parallel processes to yield a useable signal for downstream operations.

Hardware filters 1710 are fixed filters within the hardware of the cardiac pacing system. Hardware filters 1710 are designed to remove noise and apply a basic set of filtering in preparation for the operations of the software filters 1712. Hardware filters 1710 can be configured to cancel out or account for signals not generated from the patient's heart using hardware filtering solutions. In some variations, the cardiac pacing system can use a fixed hardware low-pass filter, a fixed high-pass filter, a notch filter and the like. In some variations, the cardiac pacing system can use a series of hardware filters 1710 to create a desired band-pass filter response. Some filter types contemplated include Butterworth, Chebyshev, and the like.

Multiple hardware filter band-pass filter ranges can be used to filter different signals for the cardiac pacing system. For example, a hardware filter can be included as a band-pass filter for ECG signals from 5 Hz to 25 Hz and respiration rate signal from 0.001 Hz to 0.1 Hz.

Hardware filters 1710 can be disposed in the signal path of a sensor(s). For example, hardware filters 1710 can be disposed in a lead of the cardiac pacing system, at a port for one or more conductors of a pulse generator, or the like.

A cardiac pacing system can include software filters 1712. Software filters 1712 can be configured to account for exogenous signals using software filtering solutions. Software filters 1712 can be modifiable by firmware/software to be applied to one or more sensed signals 1704. Examples of modifiable software filters include a permanent digital filter 1716 that is controllable via the programmer, a dynamic filter 1718 which is automatically adjusted based upon certain criteria and an active baseline algorithm 1720 to ensure the sensing signal remains centered about the "zero" baseline.

Software filters 1712 can be executed by one or more processors of the cardiac pacing system, such as being embodied in controller 302 of pulse generator 102 illustrated in FIG. 3. Software filters 1712 can be executed by one or more processors of a programmer, such as programmer 320 illustrated in FIG. 3.

A digital filter 1716 is a modifiable, digital software filter 1712 that can be applied to sensing channels used by the cardiac pacing system. Because the cardiac pacing system can sense numerous physiologic signals (e.g., ECG, respiration, pulse oximetry), the signal inputs 1704 for each of the physiologic signals can vary. A digital filter 1716 can be used in combination with hardware filters 1710 to refine desired bandpass settings. For example, the cardiac pacing system's fixed hardware filters 1710 may be applied to an ECG input channel using a 3 Hz to 30 Hz bandpass. Following the hardware filters 1710, a digital filter 1716 may subsequently refine the signal further to 9 Hz to 24 Hz.

A digital filter 1716 can be programmed to modify its filtering upon meeting certain conditions. For example, when additional data is collected by the cardiac pacing system suggesting a bandpass setting may be too broad and should be narrowed, upon reaching such determination, the digital filter 1716 can be reprogrammed to adjust the bandpass setting accordingly. Such reprogramming can be executed by the physician using one or more processors controlled by the programmer 320, or automatically by the cardiac pacing system.

Modifications to a digital filter 1716 can be made based on other unrelated signals sensed by the cardiac pacing system.

For example, upon sensing an increased respiratory rate by one sensing channel, the digital filter 1716 for an independent ECG sensing channel can be automatically adjusted to refine the bandpass settings, and the subsequent data, being collected during the time of increased respiratory rate. Similarly, when the respiratory rate returns to normal, the digital filter 1716 for the ECG sensing channel can return to its original bandpass setting. Similar modifications can be made in response to posture changes, heart rate or the like.

Software filters 1712 can be configured to dynamically filter noise signals. FIG. 17B is an illustration of an exemplary process flow for dynamic filtering 1718 of signals, having features consistent with the present disclosure.

In FIG. 17B at 1718, the incoming signal(s) can be dynamically filtered. Dynamic filtering 1718 can be configured to allow the cardiac pacing system to monitor sensed input signals and automatically apply a secondary digital filter profile 1730, as needed, based upon the assessment of certain criteria from such input signals. The secondary digital filter 1730 can be layered into the sensing architecture so that the secondary digital filter 1730 can be utilized, or deactivated, without affecting the permanent digital filter 1716. Dynamic filtering can provide more timely changes to the cardiac pacing system's sensing architecture for specific known events and based on assessment of certain criteria.

The filtered signal is assessed and processed based on one or more criteria 1732. The set of criteria 1732 being assessed include changes in signal amplitude, heart rate, posture, transthoracic impedance, ventricular pacing, ventricular sensing, atrial pacing, atrial sensing, morphology, frequency analysis on the template of the sensed signal, noise, states of the implanted pulse generator, and the like. Morphology assessments can include assessing monophasic or biphasic characteristics of the cardiac signal, such as narrow vs. wide signal complexes, patterns of peaks and nadirs and timing between particular signal characteristics on one or more input signals. States of the implanted pulse generator include storage mode prior to implant, set up mode at the time of implant, follow-up mode while communicating with the programmer, explant mode while surgically removing the cardiac pacing system, or other protective states that may be utilized in the presence of surgical procedures such as electrocautery, ultrasound, MRI or the like.

At 1734, a determination is made as to whether the signal meets the one or more criteria being assessed 1732. In response to a determination that the signal does not meet the criteria, no additional filter changes are required, and the signal is ready to be passed to downstream algorithms. At 1736, in response to a determination that the signal does meet the criteria, a determination can be made as to whether to alter the dynamic filter response. In response to a determination that the bandpass frequency should be altered, at 1738, the filter frequency response can be changed and the signals are then reprocessed through the modified filter. In response to a determination that the bandpass frequency should not be altered, the signals are then presented to the cardiac pacing system's downstream algorithms for processing.

Dynamically filtering 1718 can be initiated during certain testing regiments performed by the programmer, such as programmer 320 illustrated in FIG. 3. Such testing regiments can be performed following the implant procedure or in connection with certain follow-up testing. For example, a physician can apply certain dynamic filtering assessments when obtaining patient input during the setup procedure. Obtaining such user input can facilitate the normalization process for the cardiac pacing system, especially when conducting, for example, posture analysis, exercising, and the like.

An alternative example where the programmer initiates a dynamic filtering assessment is within a noisy environment. Radio frequency communication can introduce noise in the environment affecting communication between various elements of the cardiac pacing system. Sensors within the programmer and/or the cardiac pacing system can identify a high degree of radio frequency noise in the environment and temporarily activate the second dynamic filter 1730 during the communication session with the programmer. Consequently, the cardiac pacing system can modify the distorted signals through dynamic filtering 1718 to allow the intended testing within the noisy environment.

Dynamic filtering 1718 can be initiated by the cardiac pacing system based on changes in the physiological characteristics of the patient and the patient's environment. For example, if the patient's heart rate increases, the bandpass filter frequency may be narrowed temporarily by activating a second digital filter 1730 to ensure T-waves are filtered more aggressively. Such dynamic filtering adjustments can avoid over-detection of sensed signals. Similarly, if a patient works in an environment producing a high degree of noise (e.g., welder, electrician), dynamic filtering 1718 can temporarily filter the dominant frequency of the environmental noise and avoid the potential for overlying noise or saturation of sensed signals. Preventing saturation enables the cardiac pacing system to avoid missing critical indicators of heart arrhythmias, dyssynchrony, and the like.

A baseline reference value (or "baseline") is a representation of zero input on a sensing channel. With no input on a sensing channel, the signal will come to rest at the baseline value. Deflections from this baseline occur in response to measured input from the patient. For example, as the heart beats, a P-wave, QRS and T-wave are noted on the ECG. These waves are noted as voltage departures from the signal baseline on the ECG sensing channel. For proper sensing operation, it is important that the signal baseline be maintained at the zero input level such that any measurements from a sensor are accurately represented as an electrical delta from zero. Should the baseline of the signal wander away from zero, the sensing algorithms can be misled leading to inadvertent therapeutic response. Exogenous noise or patient movement can cause the baseline signal to shift even though the patient is perfectly normal and does not require therapeutic pacing treatment. Software filters 1712 and algorithmic processes can be configured to account for such baseline shifts, distinguish between treatable and non-treatable rhythms, and establish new temporary baselines in these circumstances.

The active baseline algorithm 1720 initiates temporary and remedial actions to maintain or reestablish a proper sensing baseline upon a unique baseline-shifting event. The active baseline algorithm 1720 is then deactivated upon correction of the baseline. For example, a defibrillation shock can cause the sensing inputs of the cardiac pacing system to become saturated and could inappropriately trigger heartbeat detections. This in turn could cause an inappropriate inhibition of pacing therapy delivery. The active baseline algorithm 1720 can recognize the temporary signal saturation as a defibrillation shock. To remediate the event, the active baseline algorithm 1720 can temporarily apply more aggressive filtering and algorithmic mechanisms to reestablish an appropriate baseline allowing the cardiac pacing system to make appropriate decisions based on the correct baseline signal.

In certain situations, the cardiac pacing system and the device producing the defibrillation (ICD) are in active communication with another. When notified by the ICD of a pending shock with or without post-shock pacing by the ICD, the active baseline algorithm 1720 can prophylactically condition the cardiac pacing system's sensing filters and algorithms accordingly. The resultant sensing signals following the shock will therefore maintain a proper sensing baseline and are acceptable for downstream system evaluation.

In addition to reestablishing a proper baseline following a defibrillation shock, the active baseline algorithm 1720 can temporarily alter the pacing mode of the cardiac pacing system. The heart rate can be monitored by various sensors on various leads in communication with the cardiac pacing system. Hardware and software filters can be configured to update the dynamic baseline algorithm 1720, or their level of filtering, based on the detected heart rate. Such dynamic modifications enable the cardiac pacing system to utilize an increased pacing rate or higher pacing output in a post-shock manner. For example, the active baseline algorithm 1720 can temporarily cause the cardiac pacing system to switch from a VDD mode with 50 ppm, 3.0V @ 1.0 ms to a VVI mode with 75 ppm, max output for 30 seconds.

Baseline reestablishment by the active baseline algorithm 1720 can be a repetitive process. For example, shortly after a defibrillation shock and more aggressive filter application, the sensors may continue to fail to provide meaningful readings. The active baseline algorithm 1720 can repeatedly cause the cardiac pacing system to refine filters or generate new filter schemes to cause the sensors to function properly and provide the desired information.

The active baseline algorithm 1720 can be updated based on whether the cardiac pacing system is in a sensing mode or a pacing mode. When the cardiac system is in a pacing mode it is, itself, generating electrical signals. This condition can alter or saturate one or more of the sensors. For example, the cardiac pacing system can be configured to alter the sense/pace filters of one or more specific sensing signals based on whether the cardiac pacing system is sensing or pacing. This can occur based on a time duration of a single case of pacing, or based on some percentage of time in which the cardiac pacing system is pacing.

Figure 18:
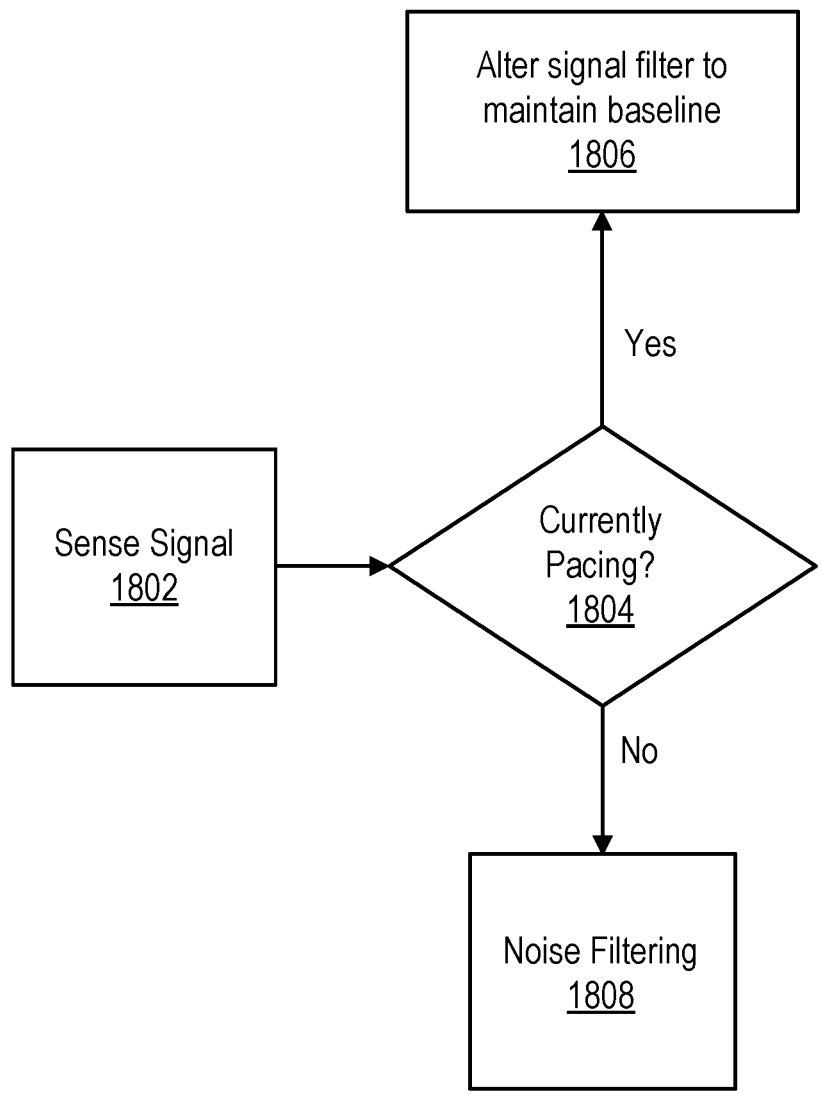
FIG. 18 is an illustration of an exemplary process flow for altering software filters and the active baseline algorithm, having features consistent with the present disclosure.

FIG. 18 is an illustration 1800 of an exemplary process flow for altering software filters and the active baseline algorithm in response to providing pacing therapy. At 1802, a signal can be sensed by the cardiac pacing system. At 1804, a determination can be made as to whether the cardiac pacing system is currently pacing the patient. At 1806, in response to a determination that the cardiac pacing system is currently providing pacing therapy, the software filters can be altered to maintain an appropriate baseline from the resultant processed signal. At 1808, in response to a determination that the cardiac pacing system is not currently providing pacing therapy, the noise can be filtered from the signal.

A cardiac pacing system can include gain amplifiers 1714. Gain amplifiers 1714 can be executed by one or more processors of the cardiac pacing system, such as may be embodied in controller 302 of pulse generator 102 illustrated in FIG. 3. Gain amplifiers 1714 can be executed by one or more processors of a programmer, such as programmer 320 illustrated in FIG. 3.

Gain amplifiers 1714 can adjust the gain of the sensed signal to generate a stable signal that is acceptable for use by downstream algorithms. For example, typical signal processing includes a phase where the analog signal is converted into the digital domain (ADC). At times, a gain multiplier/divider is applied to the analog and/or digital signal in order to improve the signal's representation to the downstream detection system.

Fixed and automatic gain control schemes can be used by the cardiac pacing system. Fixed gain control schemes use a specific gain for a specified period of time. Automatic gain control schemes continually adjust the gain based upon the size of the sensed signal. A combination of a fixed and automatic gain scheme can also be utilized. The cardiac pacing system selects or automatically adjusts gain schemes based upon a preferred sensing signal. For example, one gain scheme may be selected for ECG signals, while a differing gain scheme is selected for blood oximetry signals.

Following filtering and other signal preparation, the cardiac pacing system then evaluates whether the resultant signals are of sufficient quality to be processed for downstream sensing algorithms. The cardiac pacing system continually analyzes all of the available sensed signals against their corresponding set of acceptability requirements. Acceptability factors include signal amplitudes, signal-to-noise ratios, signal widths, frequency spectrum and time ratios. The acceptability factor for any particular signal can be further modified based upon other factors such as heart rate, posture, time of day or upon information provided by other sensors from the cardiac pacing system. For any particular sensed signal, there is a minimum acceptability score the signal must pass. A signal is discarded from further evaluation if the signal is below the minimum acceptability score. If the signal quality is passing, the signal continues to be processed, evaluated and analyzed.

While the cardiac pacing system analyzes numerous physiological characteristics such as the patient's electrocardiogram, respiration, blood oximetry, temperature, and the like, the signal selection algorithm gives preference to those signals that result in the highest sensitivity and specificity for triggering detections in response to a heartbeat or other events of interest such as skeletal muscle contraction. As such, the signal selection algorithm can dynamically preference certain sensed signals over others. Therefore, while several physiological signals are deemed equally usable because they receive passing acceptability scores, the signal selection algorithm can apply greater weight to certain signals (e.g., electrocardiogram) to other passing signals (e.g., respiratory rate) because they are more deterministic for triggering heartbeat detections. The signal selection algorithm can use a predetermined signal preference order, or alternatively, the signal preference order can be weighted differently based upon certain factors such as signal amplitude, signal-to-noise ratio, signal width, timing ratios and the like.

In certain circumstances, the cardiac pacing system assesses multiple signals for the same physiological characteristic. For example, respiratory rate signals from two different sensing pairs receive passing acceptability scores. The signal selection algorithm can analyze and select the sensing signal resulting in the best signal for electrocardiogram analysis. Alternatively, the signal selection algorithm can combine two or more signals in a manner that yields an improved composite signal for sensing evaluation. Different mathematical processes can be applied to each or combined signal(s) to yield the desired composite sensing signal. These processes may include summing/subtracting signals, multiplying or dividing one signal from others, combining the differentiated or integrated signal from other signals or other mathematical combinational methods A cardiac pacing system can include a smart switch algorithm. The smart switch algorithm can automatically initiate additional sensing and prepare to switch to an alternative sensing signal in response to certain defined detected events. The smart switch algorithm can be configured to monitor certain detected events. Examples of detected events the smart switch algorithm can monitor include signal amplitude, heart rate, posture, pace/sense modes, and/or other characteristics of the heart, patient, and/or cardiac pacing system. Upon sensing such a detected event, the smart switch algorithm can automatically switch the primary sensing signal to an alternative sensing signal upon confirmation of such detected event. For example, the manner in which signals travel through the body can change if the patient's posture changes from supine to standing. Consequently, a particular sensing signal may be the most appropriate signal in one posture, but ineffective in a second posture. As a result of programming, or learning from previous events, the smart switch algorithm can anticipate the inappropriateness of the signal selection based on the detected event and prophylactically switches to alternative sensing signal(s).

As an example, a first sensor can be disposed in the patient's body and configured to detect a first physiological characteristic of the patient. A pulse generator, receiving signals from the first sensor can be configured to have the first physiological characteristic being the primary physiological characteristic for monitoring by the cardiac pacing system. An event can occur that saturates the sensing capabilities of the first sensor, making the sensor ineffective at detecting whether or not the heart is functioning properly. The smart switch algorithm can be configured to select a second physiological characteristic as being the primary physiological characteristic for monitoring by the cardiac pacing system in response to the first sensor becoming saturated. For example, if the amplitude of the ECG increases due to changes in posture, resulting in ECG amplifier saturation, the smart switch algorithm can switch to monitoring pressure waves generated by the heart.

The cardiac pacing system can use the resultant processed sensing signal(s) to analyze whether pacing a patient's heart is appropriate. Accurately sensing atrial and ventricular activity enables the cardiac pacing system to assess the need for therapy delivery, and the appropriate pacing mode for the patient.

The cardiac pacing system of the present disclosure can be configured to monitor the activity and origin of a sensed cardiac signal. The cardiac pacing system can be configured to detect the functioning of the cardiac muscles and to provide therapy accordingly. In some variations, the cardiac pacing system can detect the functioning of the cardiac muscles using one or more accelerometers.

Sensitive accelerometers can be configured to detect motion of cardiac tissue. Accelerometer(s) can be disposed adjacent the heart of the patient. For example, accelerometer(s) can be placed in the mediastinum, intercostally, and/or in other locations suitable for sensing. The accelerometer can be configured to measure the degree of motion imparted onto the accelerometer by the beating heart.

A beating heart causes a pressure wave to be emitted from it. The accelerometer can be configured to detect the localized tissue movement due to the pressure wave and provide indications on the functionality of the heart by analyzing the resultant signal. However, the accelerometer can also be affected by exogenous motion attributable to other factors, such as movement of the patient, breathing, sound waves, and the like. In certain instances, this exogenous motion can dwarf the motion attributable to the pressure waves from the heart.

Exogenous motion can be filtered from the received signals using a combination of hardware and software filters as previously described. Exogenous motion can be also be filtered from the received signals when at least two sources are used to facilitate the detection of the motion of the heart. Subcutaneous accelerometer(s) (SA) can be placed, for example, on the pectoral region of the patient. A second heart accelerometer (HA) can be placed adjacent the heart, for example, on a lead inserted through the intercostal space in the region of the anterior mediastinum. Movement of the heart causes pressure waves travelling through tissues of the patient to be detected by both accelerometers, but each accelerometer receives a different signal based on the path taken and the interference or exogenous motion added during propagation of the signal. In some cases, the intensity of the interference or exogenous motion can far exceed the intensity of any pressure wave attributable to the functioning of the heart. Consequently, the interference or exogenous motion detected by the accelerometers can dwarf the pressure wave signal attributable to the heart.

The SA can be configured to transmit subcutaneous vibration measurement(s) to the pulse generator. The HA can be configured to transmit a cardiac vibration measurement to the pulse generator. The pulse generator can be configured to factor the subcutaneous vibration measurement(s) from the SA into the cardiac vibration measurement from the HA to assess a physiological characteristic of the heart. In some variations, the factored vibration measurement can be processed using one or more filters. In some variations, the cardiac vibration measurement and/or the subcutaneous vibration measurement can be processed using one or more filters prior to being factored. The resultant vibration measurement can provide a desired signal that the cardiac pacing system can analyze to assess heart functionality.

In some variations, the SA can be disposed within the housing of the pulse generator, at the end of a lead disposed within the patient, and the like. In some variations, multiple HA and SA accelerometers can be used. The multiple HAs and SAs can be disposed at different locations throughout the body. For example, multiple HAs can be disposed about the heart. The HAs being at different locations can facilitate determination of the movement, or beating, of different portions of the heart. In this manner, a virtual model of the complete functionality of the heart can be generated which can form the basis of adjustments to the pacing by the cardiac pacing system.

Triggering of certain heartbeat detections can be performed by the cardiac pacing system using one or more acoustic sensors. Acoustic sensors function similarly to a stethoscope. As such, acoustic sensors can be configured to detect sound waves generated by the heart. The cardiac pacing system can sense and analyze sound wave signals to determine whether or not pacing therapy is required. Analysis of the sensed sound wave signals can include identification of known sounds, such as the sounds made when the mitral and tricuspid valves close (S1 sounds). Analyzing sound waves can be an effective way to separate T-wave signals, a period of relatively little acoustic pressure, from QRS complex and S1 sounds, when T-wave signals become a prominent component of the ECG signal. The cardiac pacing system can be configured to use filters, such as the filters described herein, to separate exogenous sounds from the cardiac sounds prior to the analysis by algorithms of the cardiac pacing system.

Figure 19A:
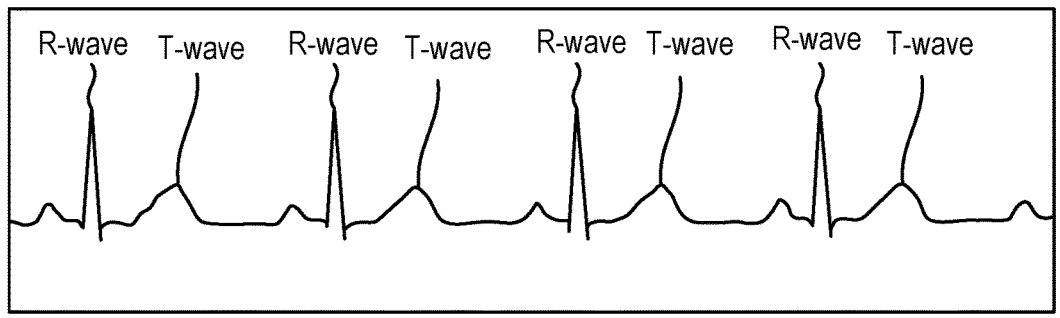
FIG. 19A is a graph of an example of an ECG of a heart.
Figure 19B:
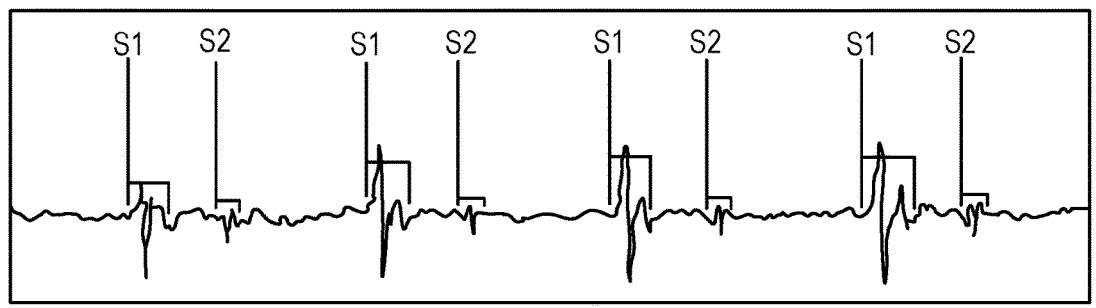
FIG. 19B is a graph of a simultaneous acoustic signal as the ECG signal shown in FIG. 19A.

FIG. 19A is an example of an ECG 1901 of a patient having prominent T-wave signals. FIG. 19B is an example of a simultaneous acoustic signal 1902. These figures demonstrate that acoustic signals can be used to distinguish desirable signal attributes such as ventricular depolarization (the R-wave on the ECG and the S1 from the heart sound signal) from undesirable signal attributes such as ventricular repolarization (the T-wave on the ECG and the S2 from the heart sound signal). In this example, the corresponding T-wave event on the acoustic signal is less prominent than the same T-wave event shown on the ECG.

Figure 20:
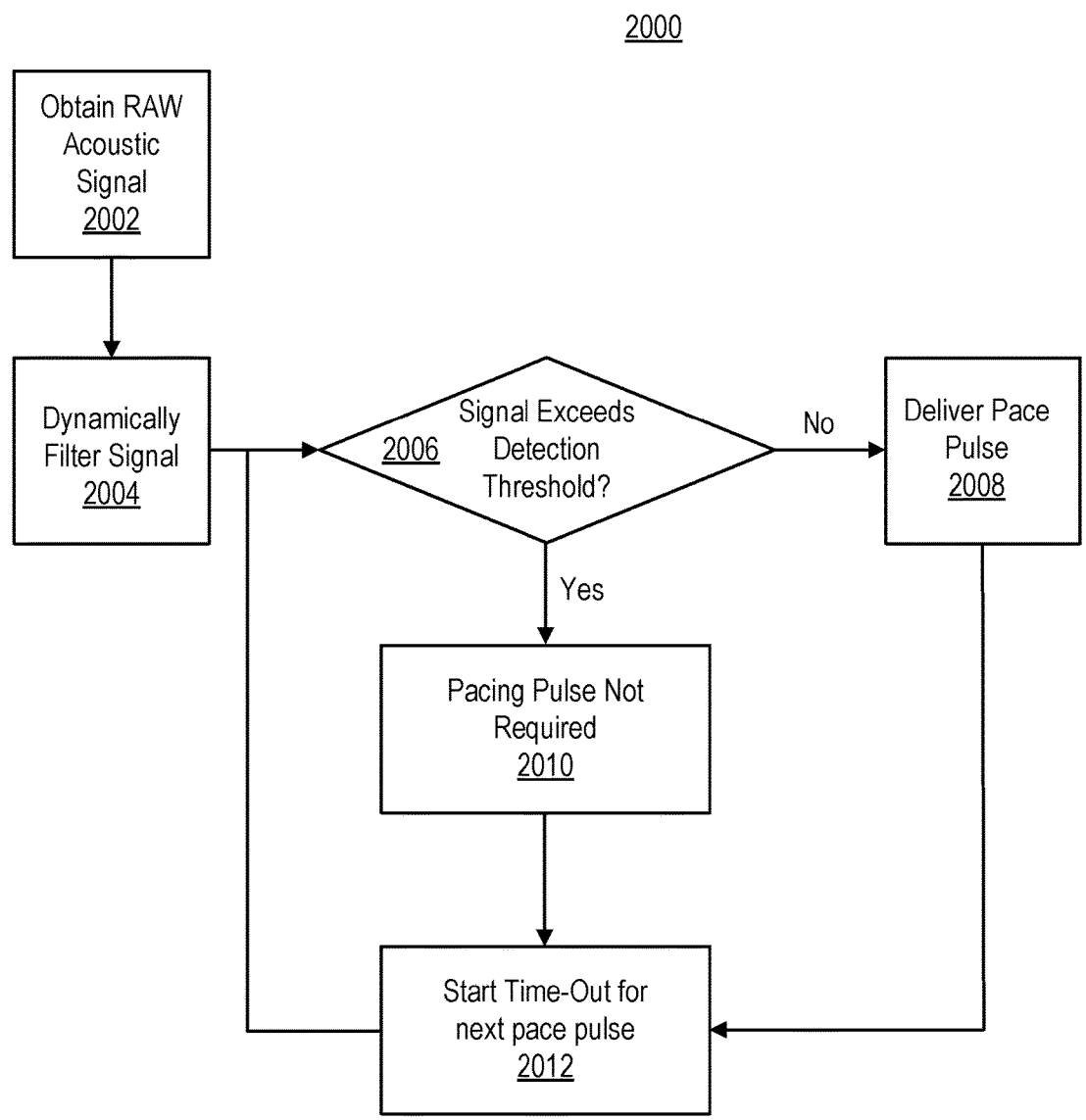
FIG. 20 is an illustration of an exemplary process flow for processing acoustic signals obtained by the cardiac pacing system, having features consistent with the present disclosure.

FIG. 20 is an illustration 2000 of an exemplary process flow for processing acoustic signals obtained by the cardiac pacing system, having features consistent with the present disclosure. At 2002, an acoustic signal can be obtained by the cardiac pacing system. At 2004, the signal can be dynamically filtered using the dynamic filtering algorithm and techniques described in the present disclosure. At 2006, a determination can be made as to whether the signal exceeds a detection threshold. At 2008, in response to a determination that the signal does not exceed a detection threshold, the cardiac pacing system can be configured to deliver a pacing pulse. At 2010, in response to a determination that the signal does exceed a detection threshold, it can be determined that a pacing pulse is not required. At 2012, in response to no pacing pulse being required at 2010, or in response to the delivery of a pulse at 2008, the cardiac pacing system can be configured to restart the analysis to determine the need for the next pace pulse.

In some variations, the acoustic signal, generated by the sound waves caused by the beating heart, can be captured via an accelerometer located on an implanted lead. In some variations, an accelerometer can be used where an acoustic sensor cannot.

The cardiac pacing system can be configured to monitor the functionality of particular chambers of the heart such as the atria. The functioning of the particular chambers of the heart can be monitored in similar manners as the general cardiac sensing techniques described herein. Additionally, the filtering techniques described in the present disclosure apply equally to atrial sensing as they to do to ventricular sensing, and sensing of the heart generally.

The cardiac pacing system can include multiple sensors at multiple sensing vectors around the heart. The sensing vectors can be at predefined locations, or along predefined planes, relative to the patient's heart. The sensors creating the multiple sensing vectors can be configured to triangulate, and therefore pinpoint, the location of a source of a signal and determine how and where the signal is propagating.

ECG signals can propagate from the heart through other anatomical structures within the body. The propagation of the ECG signal can be obtained by the multiple sensors. The cardiac pacing system can be configured to process the propagated signals to determine if the source of the ECG signal originates from higher within the thorax, near the atrium of the heart, or lower within the thorax, near the ventricle of the heart.

For example, a sensor on the pulse generator (SPG) placed over the sternum will have a unique angle and shorter distance to the atria than an alternative sensor (SA) placed in the intracostal space inferior to the pulse generator. Signal analyses of a particular feature can be performed to determine differences in amplitudes and relative timing. Due to proximity, the feature as measured from SPG will have larger amplitude and occur before the feature as it is measured from SA. These timing relationships can be used to determine whether the origin of the signal is atrial or ventricular in nature and the direction of signal propagation.

In some cases, alignment of various elements of the cardiac cycle may be used for timing comparison between sense vectors. These features can include the onset (starting point), completion (ending point), mid-point, inflection point, zero-slope point, positive peak (signal maximum), negative peak (signal minimum), steepest slope, or area under the curve of a particular portion of the ECG (P-wave, QRS, T-wave, etc.). These alignment points can be compared across multiple sense vectors to identify timing relationships. Additionally, multiple alignment points can be combined during the comparative analysis with an alternate sense vector. Signal elements from other non-ECG sensors (accelerometer, blood oximetry, pulse pressure, etc.) can also be used for alignment purposes.

The cardiac pacing system can be designed with a dedicated signal triangulation circuit or real-time algorithm that continually outputs the calculated source location of the signal source. The output of the signal triangulation can consist of a matrix ID or a grid coordinate method to represent the location of the signal source. This output can be calibrated for the patient automatically by the cardiac pacing system or with physician input via a programmer, such as programmer 320 in FIG. 3. For example, following implantation of the cardiac pacing system, a calibration routine can be used to analyze the real-time signals from multiple ECG vectors available from the cardiac pacing system. This calibration can include input from the physician to specify or confirm the P-wave or R-wave elements of the ECG. Once confirmed, the cardiac pacing system can identify the range of coordinates that each real-time signal represents, and the direction of the signal's propagation.

Signal triangulation can guide therapy delivery for the cardiac pacing system. For example, signal triangulation can be used to identify instances when an atrial signal does not conduct to the ventricle. In these instances, the cardiac pacing system can deliver a ventricular pacing pulse to assist with proper cardiac conduction. Alternatively, signal triangulation can be used to confirm intrinsic ventricular depolarization and inhibit pacing therapy.

Figure 21A:
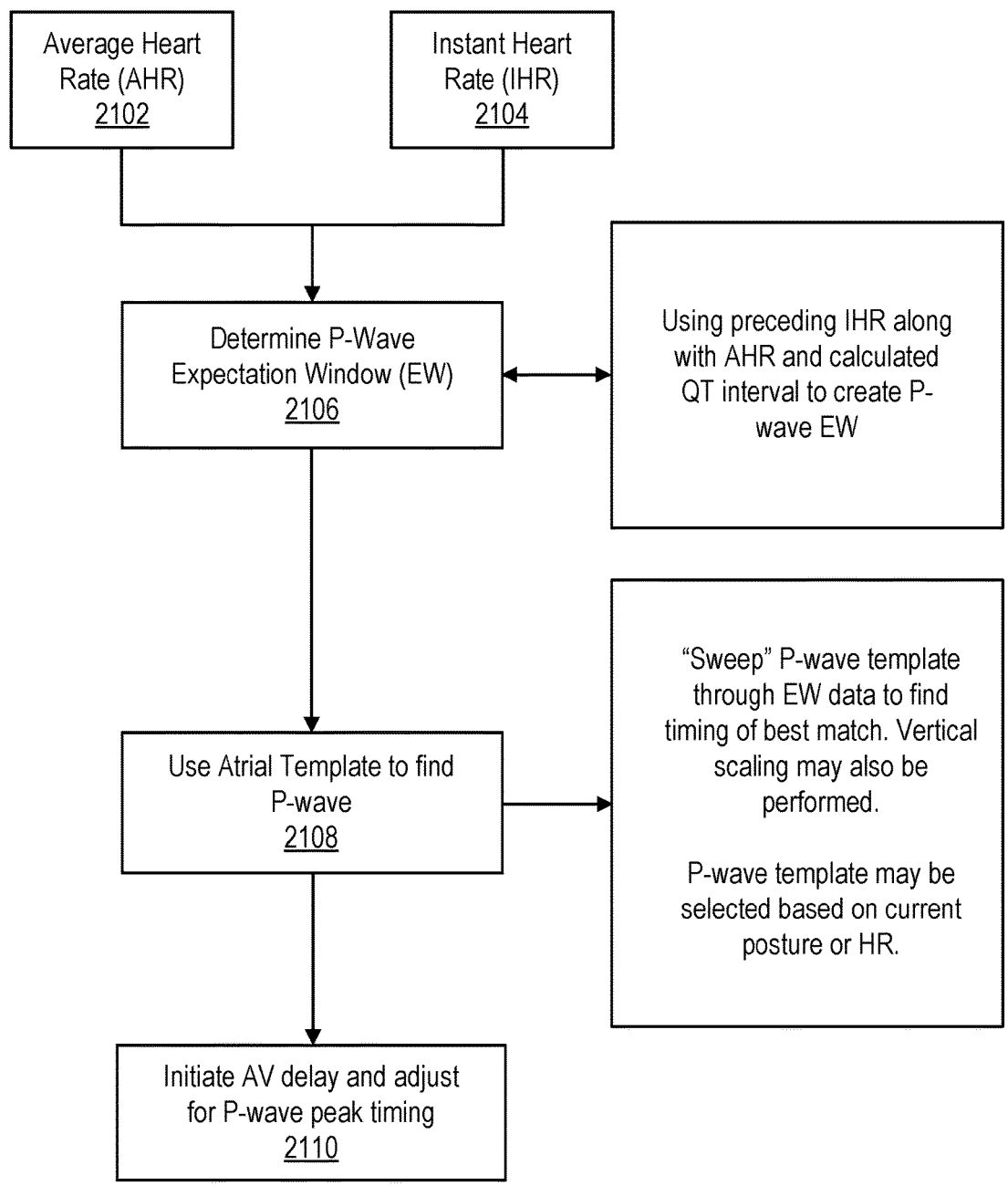
FIG. 21A is an illustration of an exemplary process flow for an atrial template reference having features consistent with the present description.

FIG. 21A is an illustration 2100 of an exemplary process flow for an atrial template reference having features consistent with the current subject matter. An atrial template reference can use a known template for a particular signal for comparison against a signal detected by one or more sensors of the cardiac pacing system. This comparison can be performed to find P-waves on a live streaming signal. The atrial template signal can be collected by a programmer, such as programmer 320 of FIG. 3, and fed into a controller, such as controller 302 of FIG. 3. In some variations, the template can be stored within electronic storage of the pulse generator, such as electronic storage 308 of FIG. 3. In some variations, multiple templates can be obtained that reflect the signal template when the patient is in different postures, has different heart rates, for different sense vectors, and other like parameters.

Figure 21B:
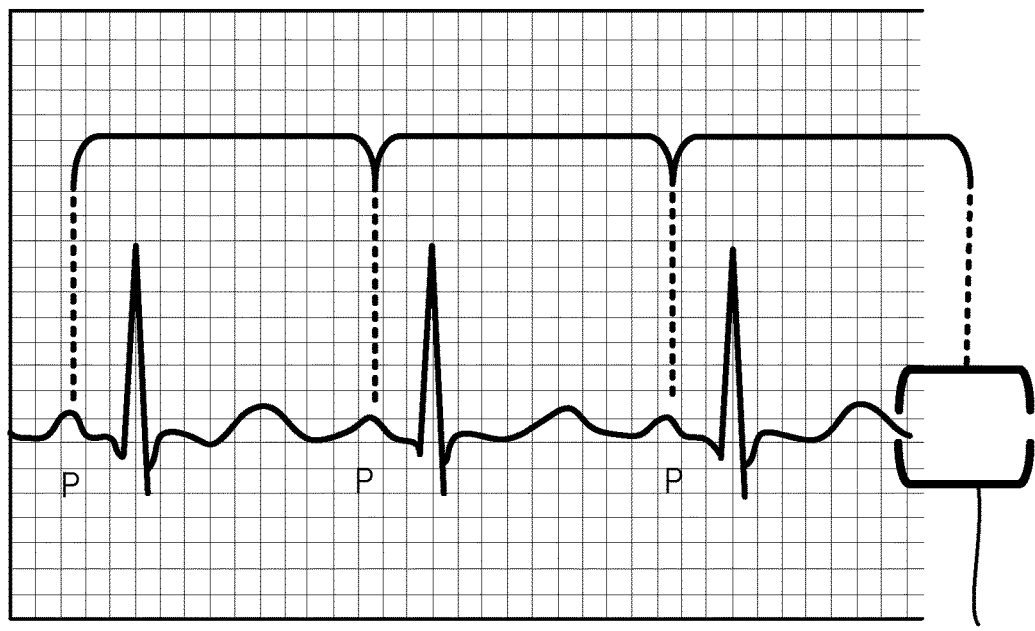
FIG. 21B is an illustration of a P-wave signal indicating the "expectation window"

During sinus rhythms, the interval between consecutive P waves does not change significantly on a beat-to-beat basis. Consequently, the cardiac pacing system can be configured to use an "expectation window" to determine when in time a subsequent P-wave would be expected to occur. FIG. 21B is an illustration of a P-wave signal illustrating an "expectation window." Within this window, the signal can be analyzed and compared to the known template in order to confirm the presence of a P-wave. By limiting this analysis to the expectation window, false positive matches to other signal features such as the T-wave can be avoided or minimized.

Expectation windows can also be used to identify irregular P-wave intervals indicative of atrial arrhythmias. In response to identifying these irregular intervals, the pacing mode or other settings can be automatically altered to ensure appropriate pacing therapy continues. Settings can then automatically revert back to the previous settings when regular intervals are identified and the arrhythmia terminates.

AV delays can be similarly triggered once a P-wave is confirmed. The AV delay can also be adjusted based on the timing location of the peak, onset, termination, and the like, of the P-wave. In some variations, the "expectation window" can be based on a combination of average heart rate for the patient and the preceding P-P interval or R-R interval. The duration of the expectation window can also be automatically shortened or lengthened based upon the heart rate, or adjusted via the programmer.

At 2102, the average heart rate (HR) of the patient can be obtained. At 2104 the instant HR of the patient can be obtained. At 2106, the average HR and the instant HR can be used to determine the P-wave expectation window. At 2108, the atrial template reference can be used to find the P-wave. At 2110, the AV delay can be initiated and adjusted for the detected P-wave peak timing.

While expectation windows have been disclosed with reference to atrial signals, the description is additionally applicable for ventricular signals. For example, expectation windows can be used to determine when in time a subsequent R-wave would be expected to occur.

Figure 22:
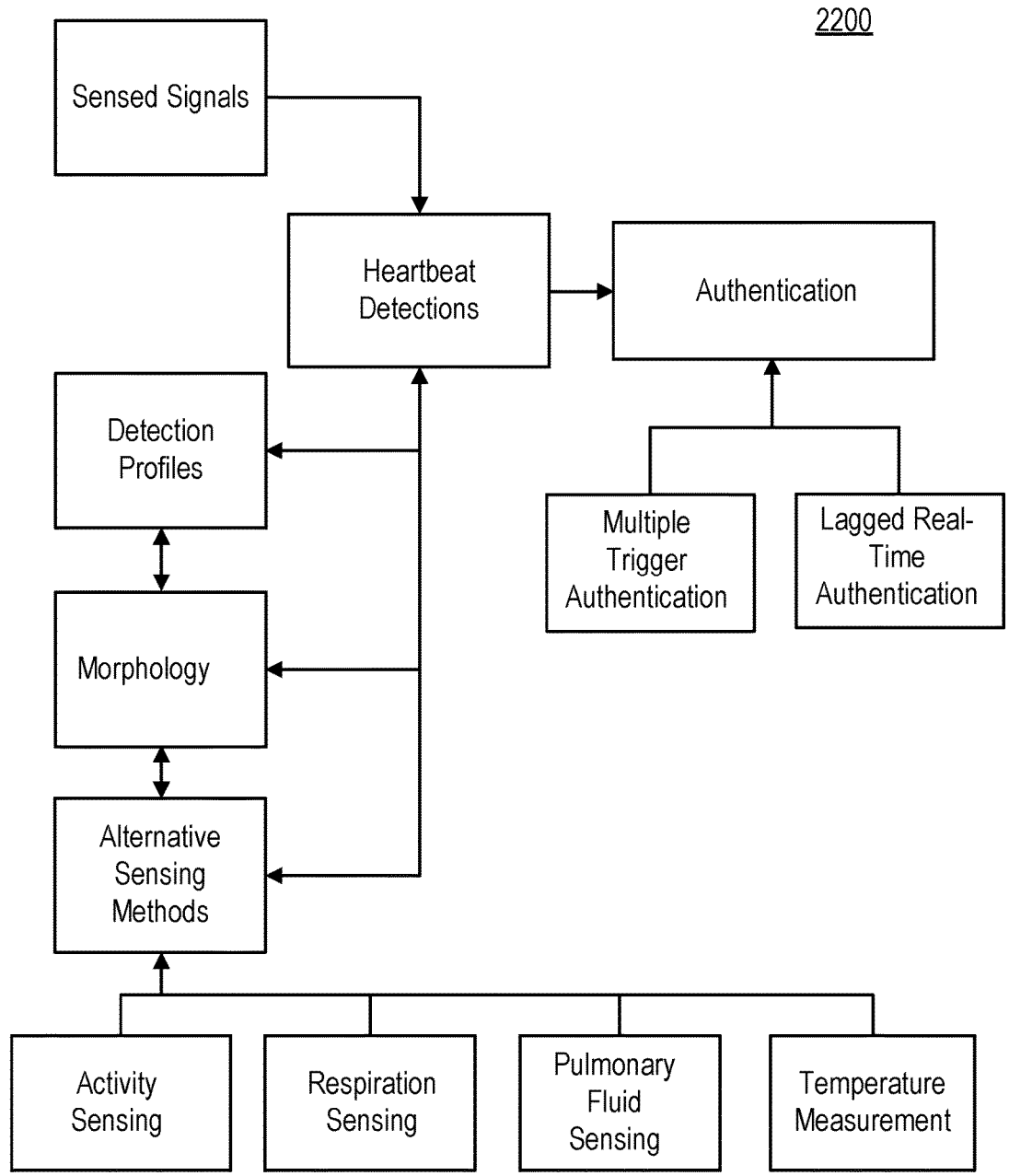
FIG. 22 is an illustration of an exemplary process flow for analyzing sensed signals for the triggering and authentication of heartbeat detections, having features consistent with the present disclosure.

Following the filtering stage and selection of the preferred sensing signals for analysis, the cardiac pacing system can then analyze these signals for heartbeat detections and assess the need for therapy delivery. FIG. 22 is an illustration of an exemplary process flow 2200 for analyzing sensed signals for the triggering and authentication of heartbeat detections, having features consistent with the present disclosure.

Detection profiles are used to trigger heartbeat detections from a selected sensing signal. A detection profile is a threshold value used for comparison with the preferred sensing signal. If the sensing signal exceeds the detection profile threshold, a heartbeat detection is triggered. If the sensing signal remains below the detection profile threshold, sensing continues until a heartbeat detections is triggered.

Detection profiles can take many forms and are based upon the type of sensing signal being analyzed. A horizontal, equipotential level (horizontal line) is an example of a detection profile. In this example, a fixed horizontal detection profile of 5 mV will trigger a heartbeat detection when the sensing signal exceeds the 5 mV detection profile threshold. The detection profiles can include horizontal (equipotential) elements, decaying elements of various shapes such as fixed slope, exponential decays, and the like, increasing slope elements of various shapes such as fixed slope, exponential growths, and the like, or a combination of elements.

Detection profiles are selected based upon the type of sensing signal being analyzed. Similarly, multiple detection profiles can be used for a particular sensing signal. For example, the cardiac pacing system will select a detection profile designed for ECG sensing over a detection profile for a respiration signal when analyzing an ECG signal. Similarly, the cardiac pacing system will select a detection profile designed for atrial ECG sensing over a detection profile for ventricular ECG sensing when analyzing an ECG signal for P-waves by the sensing algorithms described herein.

Detection profiles can include periods where heartbeat detections are temporarily inhibited. Such periods can be used immediately following the triggering of an initial heartbeat detection in order to prevent a subsequent erroneous heartbeat detection for some period of time. Furthermore, heartbeat detections from one sensing signal may initiate non-detection periods on alternate sensing signals.

Elements of the detection profile and non-detection windows can be automatically adjusted based upon attributes of the sensing signal such as mode of pacing, ectopic cardiac events, signal amplitude, heart rate, time of day or other sensor input such as accelerometer or posture, and the like.

Morphology comparison methods can be used as a means to trigger heartbeat detections and identify the occurrence of specific cardiac events. This comparison method may be performed in real-time using morphology detection algorithms or hardware circuitry. For example, if the morphological shape of a ventricular depolarization is known from an ECG signal, a template of that known shape can be created and used for subsequent comparison. The template can then be continually scanned in real-time throughout the sensing signal to identify when the known shape reoccurs. When a pattern match is noted, a heartbeat detection can be declared. As a result, this method can identify the occurrence of a subsequent ventricular depolarization.

The template can be collected by a programmer, such as programmer 320 of FIG. 3, and fed into a controller, such as controller 302 of FIG. 3. In some variations, the template can be automatically generated and stored within electronic storage of the pulse generator, such as electronic storage 308 of FIG. 3. Historical templates can be used to generate or update a primary template, or a primary template can be a based upon the compilation of some number of previous heartbeat detections.

In some variations, multiple templates can be obtained that reflect the template when the patient is in different postures, has different heart rates, for different sense vectors, and for other like parameters. Furthermore, the selection of the appropriate template for comparison can be automatically updated based upon factors including pacing mode, heart rate, posture, time of day or other measures of the input signals. Alternatively, several measured or artificially created templates can be stored by the cardiac pacing system and used for the morphology detection algorithms.

Different elements of sensed signals can be used for comparison purposes. For example, ventricular depolarizations may be used to store the ventricular signal template, while a separate signal template is stored for atrial depolarization detections. Furthermore, non-heartbeat signals and templates can be used for morphology comparisons. For example, a unique shape of the respiration signal can be used to count the number of breaths per period of time, indicative of the respiratory rate.

Morphology comparison methods can be performed with software and/or hardware processing. Automatic adjustment of the signal or stored template can be performed prior to or during the morphology comparison process. Such adjustments include scaling methods of the amplitude or width, time shifting of either the signal or stored shape, or the like.

Morphology detection methods can be used independently, or in conjunction with certain detection profiles. For example, a detection profile can be used first to trigger a heartbeat detection. This initial heartbeat detection can then initiate a morphology comparison algorithm to confirm or call into question the initial heartbeat detection. Alternatively, both algorithms may be operating in parallel to independently evaluate heartbeat detections.

Alternative sensing methods can be analyzed to confirm or question certain sensing signals collected by the cardiac pacing system. Sensors collecting information regarding a patient's activity and respiration rate provide the cardiac pacing system additional analysis tools to confirm heartbeat detections and assess the need for therapy delivery.

Activity sensors can be used to determine the current activity levels of the patient. Activity sensors such as accelerometers can be used to indicate patient movement and activity and can be, for example, incorporated into an implanted pulse generator housing. The accelerometer signal can be analyzed to determine the degree of movement by the patient. As patient movement increases, heart rate demands generally rise as well.

An algorithmic comparison of the actual versus ideal heart rate for any given degree of movement can be used to automatically adjust a cardiac pacing system's rate-responsive pacing rate. If the activity sensor indicates a high degree of patient movement, yet the measured heart rate falls below the ideal heart rate by a pre-determined range, the pacing rate may be temporarily increased. The degree of heart rate increase is related to the degree of activity, up to a pre-determined maximum pacing rate. Conversely, when the activity sensor indicates less motion, the pacing rate can be reduced over-time to some pre-determined lower pacing rate.

Filtering of the accelerometer signal can separate outside motion from the actual movement of the patient. For example, filtering can be used to separate the motion from a patient sitting calmly in their car as compared to a patient running up a set of stairs.

Respiration sensing can be used to determine the current activity levels of the patient. As a patient's activity increases, oxygen demand generally increases and the respiration rate and volume increase accordingly. By detecting these changes in respiration, heart rate requirements can be assessed. If respiration rate and/or volume increase without a correlative heart rate increase, the pacing rate can be automatically increased to improve hemodynamic response for the patient.

Respiration sensing can be used in conjunction with activity sensing to improve the cardiac pacing system's response. If an activity increase is noted and a correlative respiration increase is not observed, exogenous noise activity can be suspected. The cardiac pacing system can analyze additional sensed signals to assess whether the discrepancy is noise related. If so, the cardiac pacing system can alter its primary sensing profile to an alternative sensing profile in efforts to avoid the discrepancy and assess an actual heart rate. Additionally, the information about the discrepancy can be retained by the cardiac pacing system as a detected event for future smart switch algorithm usage.

Leads and electrodes placed in locations consistent with the current subject matter will be in relatively close proximity to the lungs. This proximity to the lung can facilitate several methods to assess changes in lung status such as pulmonary edema. Methods to detect changes in lung fluid status include the delivery of sub-stimulation levels of energy with a pacing vector that includes a portion of the lung tissue. Changing fluid levels in the lung will result in changes in measured impedance.

Changes in pulmonary status are generally caused by heart failure or other cardiac conditions requiring medical treatment. As such, sensed changes in lung status can be communicated to the physician at in-person visits or remotely to facilitate appropriate medical treatment. Additionally, the pacing mode, pacing rate and pacing energy can be automatically adjusted in response to changes in lung status.

Leads and electrodes placed in locations consistent with the current subject matter can include temperature probes. Temperature measurements within the mediastinum can be recorded by the cardiac pacing system and provided to a physician during in-person visits or remotely. Recording temperature data over time creates a normal temperature pattern. Aberrations in the normal temperature pattern can be detected and communicated to a physician so a definitive diagnosis and appropriate medical treatment can be performed and prescribed. Additionally, the pacing mode, pacing rate and pacing energy can be automatically adjusted in response to temperature changes.

Authentication is a confirmation process used to ensure the accuracy of the sensing signal(s) and that the subsequent heartbeat detections or inhibition decisions made by the cardiac pacing system are appropriate. The authentication process utilizes algorithms to analyze heartbeat detection decisions from multiple signal inputs and multiple signal processing steps for a consistent decision. If discrepancies are found from one input or process to another, the cardiac pacing system can change the sensing signal or detection process that consistently makes the most appropriate heartbeat detection decisions.

The authentication process continually monitors all of the acceptable signals to ensure they all yield similar heartbeat detections. To preserve energy for the cardiac pacing system, the authentication process can be initiated randomly to test the system's performance. Should repeated errors in performance be noted, the frequency and intervals of the authentication process can be adjusted until reliable heartbeat detections are observed. Alternatively, every time a heartbeat detection is triggered on the primary sensing channel, the sensing signals or detection processes of the alternate channels can be monitored to ensure that they would have also triggered a heartbeat detection; however, these additional signals can be post-processed in batches of 5-sec segments, or within another time window and frequency that is considerate of power consumption by the system.

In instances when sensing algorithms trigger a heartbeat detection and subsequently inhibit a pace pulse, algorithms used in the authentication process will confirm that the heartbeat detection was accurate and not an over-detection of some non-cardiac event. Conversely, if a pacing pulse is required, algorithms used in the authentication process will confirm that an intrinsic beat was not missed. If some quantity of non-agreements are noted, algorithms such as the signal selector algorithm can be initiated to ensure that the current primary sensing vector is still the most robust of those options available for the system.

The cardiac pacing system can be configured to verify whether delivery of therapeutic pulses is required. This verification can be performed using one or more sensors. For example, the cardiac pacing system can use a multiple trigger authentication. Multiple trigger authentication uses multiple input signals to confirm whether a pacing pulse is required. As an example, the cardiac pacing system can have its primary sensing signal set to the ECG input from the sensors configured to monitor the ECG of the patient's heart. The ECG will not trigger a heartbeat detection if the ventricle does not beat; however, a QRS signal amplitude decrease can lead to a "missed" heartbeat detection. A second input signal can be used to confirm what the QRS signal indicates. For example, simultaneous monitoring of the heart sound, such as with acoustic sensors or accelerometers, can be used to confirm whether or not the ventricle beat. Heart sounds lag the ECG electrical response signal, making the use of heart sounds as the secondary confirmation signal especially useful.

Figure 23:
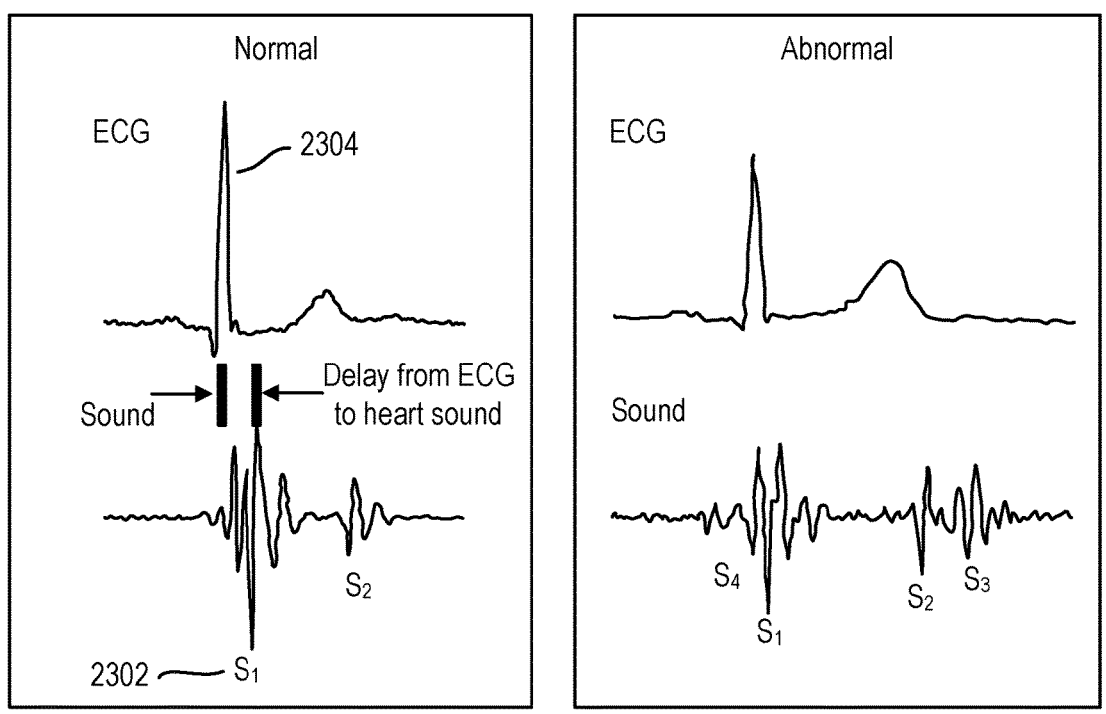
FIG. 23 is an illustration of an ECG reading over time together with a time synchronized heart sound signal reading over time having features consistent with the present disclosure.

FIG. 23 is an illustration 2300 of an ECG reading over time together with a time synchronized heart sound signal reading over time. As shown in FIG. 23, the $S_1$ heart sound, representing the ventricular pressure wave, 2302 lags the QRS complex from the ECG reading 2304 associated with the ventricular depolarization. Other heart sounds $S_2$, $S_3$ and $S_4$ may also be used to identify specific normal or abnormal cardiac activity for the purposes of adjusting, inhibiting or delivering therapy or providing diagnostic feedback regarding the patient to the physician.

Figure 24:
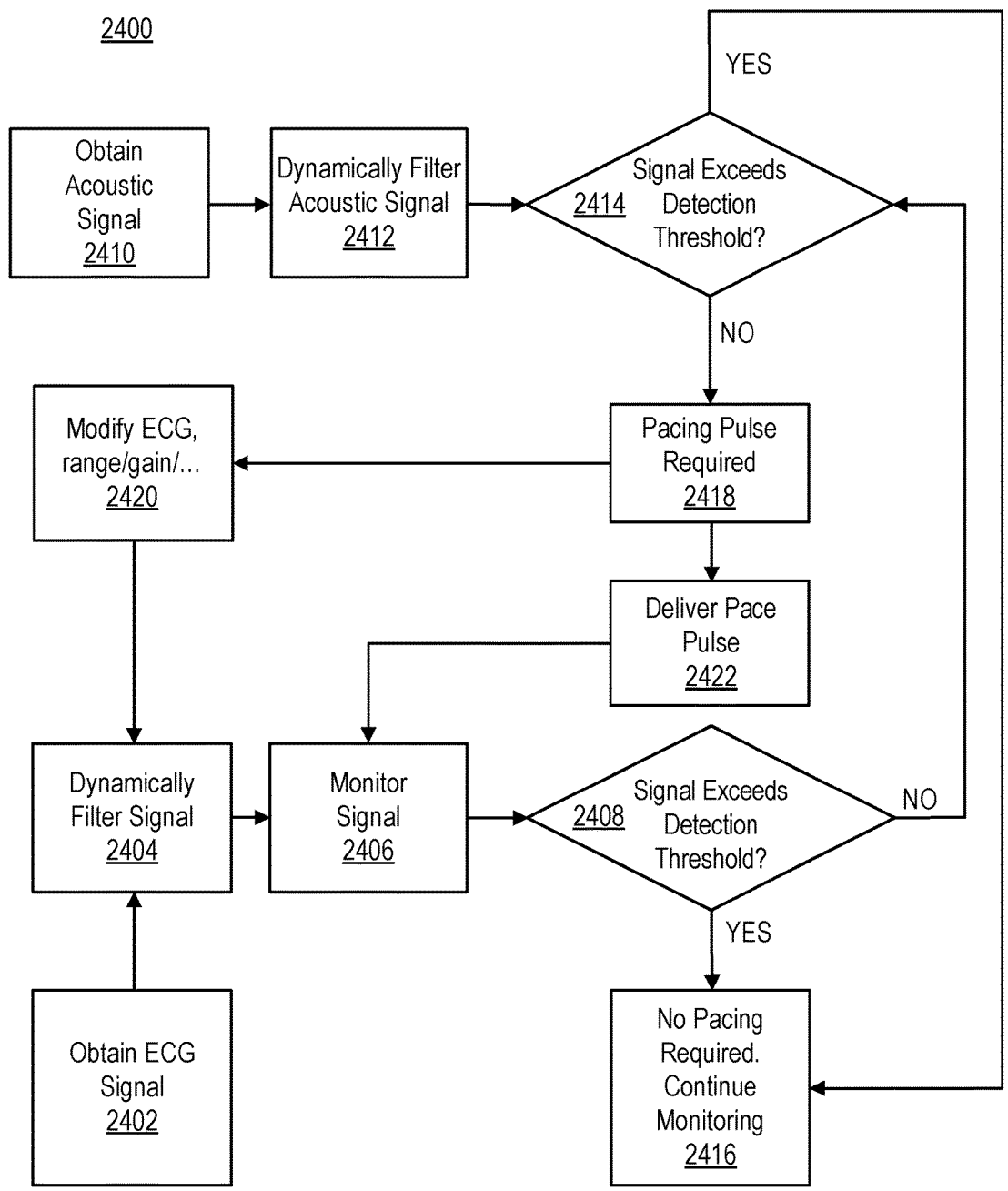
FIG. 24 is an exemplary process flow for verifying a lack of heart beat having features consistent with the current subject matter; and, FIG. 25 is an illustration of an exemplary process flow for analyzing sensed signals to determine whether delivered energy levels and/or pacing vectors can be adjusted, having features consistent with the present disclosure.

FIG. 24 is an illustration of an exemplary process flow 2400 for verifying a lack of heart beat having features consistent with the current subject matter. Process flow 2400 is provided as an example of a process that could be performed by the cardiac pacing system to verify whether or not the ventricle, for example, has stopped beating. At 2402, the ECG signal can be obtained by the cardiac pacing system. At 2404, the ECG signal can be filtered. The filtering can include filtering techniques consistent with the present disclosure. At 2406, the ECG signal can be monitored for a duration of time consistent with a desired pacing rate. In response, at 2408, a determination can be made as to whether the signal exceeds a detection threshold using heartbeat detection techniques consistent with the present disclosure. If the signal does not exceed a detection threshold, then reference to the acoustic signal detection can be made.

At 2410, an acoustic signal can be obtained by the cardiac pacing system. At 2412, the acoustic signal can be dynamically filtered by the cardiac pacing system. At 2414, a determination can be made as to whether the acoustic signal exceeds the detection threshold. If the acoustic signal does exceed the detection threshold, then, at 2416, no pacing is required and monitoring of the heart can proceed. If, at 2414, the acoustic signal does not exceed the detection threshold, then, at 2418, a determination of whether a therapeutic pulse is required for delivery to the heart can be made. At 2420, in response to determining a pulse is required, the ECG sensors can be modified in order to improve the accuracy for triggering heartbeat detections. For example, the range, gain, and/or other parameters of the ECG can be modified. At 2422, a therapeutic pulse can be delivered to the heart. Subsequently, the signals can be monitored.

Sensing for heartbeat detections must operate in real-time as pacing is triggered on a beat-to-beat basis. Lagged real-time analysis is an authentication process that runs in a delayed fashion allowing for the processing of additional data that was not otherwise available at the very moment the real-time decision was made. Following an initial heartbeat detection, the lagged real-time analysis will continue to gather data and, following the post-processing of that data, can ultimately over-rule the primary detection decision, resulting in a decision to deliver a therapeutic pace pulse. For example, if the primary triggering mechanism for heartbeat detections uses the ECG signal with an exponentially decaying detection profile, and a sensed event is triggered, it will subsequently specify that the pacing pulse should be inhibited. The lagged real-time analysis can continue to gather data and, using a previously stored morphology template, can compare data that occurred after the primary detection to the morphology template. This analysis can confirm that the primary detection was in fact triggered by the desired event and not an over-sensing of some other ECG segment or non-cardiac signal. The additional data collection can be of a varying period of time such as 10% of the previous R-R interval, or other periods of fixed or relative time.

Alternatively, if the primary triggering mechanism for heartbeat detections indicates that no-sensed event occurred, pacing will be initiated. The lagged real-time analysis may optionally include a first-pace delay feature that intentionally delays or overrules a pacing pulse delivery decision if a pacing pulse has not been delivered for some preset period of time. For example, no pacing pulses have been delivered for 10 minutes; however, the real-time primary detection suddenly indicates that a pace pulse is required. Rather than immediately delivering the pace pulse, the lagged real-time analysis invokes a 100 ms first-pace delay in order to analyze additional data to confirm that intrinsic activity was not missed. If pacing is required, the first-pace delay is reduced or eliminated for the next paced beat. If pacing inhibition is confirmed, additional pace delays or pacing rate adjustments can be made to promote continued intrinsic heartbeats.

Lagged real-time analysis can include maximum interval thresholds to ensure pacing is not inhibited for a clinically undesirable duration.

Pacing vector selection is designed to evaluate all pacing vector choices available in order to select the optimal pacing vector. Multiple pacing choices may be acceptable, allowing the device to have options for changing the vector automatically if other sensor input suggests that a change is required.

Pacing vector selection compares pacing requirements for some or all of the pacing vector electrodes available to the cardiac pacing system. In addition to electrode pairs, more than two electrodes may also be used for pacing delivery, with one or more electrodes acting as the cathode and one or more electrodes acting as the anode during pacing delivery.

An optimal pacing vector is one that minimizes pacing energy while maintaining adequate pacing energy safety margin. Analysis may include the assessment of skeletal muscle stimulation during pacing and/or the assessment of pacing requirement changes with various patient postures, respiration sizes (deep breath), heart rates, and the like. The resulting optimal pacing vector can be determined by combining some or all of these variables using a weighted or non-weighted scoring method. As such, the pacing vector with the lowest energy requirement may not necessarily become the optimal pacing vector. Other vectors with low energy requirements that minimize other factors such as skeletal muscle stimulation may be preferred.

The pacing vector selection algorithm can generate a list of all acceptable or unacceptable pacing vectors. These lists can then be used by other algorithms to optimize particular sensor/electrode pairs for sensing and therapy delivery. For example, it is desirable to sense from electrodes that are not involved in delivery of therapeutic pacing pulses due to latent polarization effects. Polarization effects can degrade sensing performance of the cardiac pacing system. Allowing the system to utilize distinct electrodes to perform sensing and pacing functions enables the system to optimally select sensing pairs sufficiently far away from the interface between pacing electrodes and surrounding tissue, which is most susceptible to polarization effects each time a pacing pulse is delivered. As such, the pacing vector selection algorithm can work in concert with sensing algorithms to automatically switch sensing and therapy delivery electrode pairs to optimize system performance.

The programmer can be used during the pacing vector selection assessment in order to provide confirmatory responses for certain pacing vectors. During in person follow-up visits, a range of amplitude and pulse widths for each available pacing vector configuration can be evaluated. For each setting, the degree of skeletal muscle stimulation and any resulting perception of discomfort can be assessed, along with cardiac pacing thresholds. The degree of skeletal muscle stimulation can be measured automatically by the cardiac pacing system and/or programmer by analyzing signals from an accelerometer, or like sensor, designed to detect skeletal muscle stimulation. The perception of any discomfort can be provided by the patient to the physician conducting the procedure for each pacing vector. The patient can accept or reject one or more pacing vectors during the assessment. Cardiac pacing thresholds can be measured by the physician performing the follow-up visit or automatically by the cardiac pacing system. Factors used in the prioritization of pacing vectors include (1) cardiac capture thresholds, (2) degree of skeletal muscle stimulation at tested outputs, (3) patient perception of discomfort at tested outputs and (4) degree of separation between cardiac capture thresholds and onset of skeletal muscle stimulation or perceived discomfort for each pacing vector. These factors may be analyzed in one or multiple postures and across varying degrees of activity and heartrates. Information from the assessment can then be saved in the cardiac pacing system allowing the pacing vector selection algorithm to create a prioritized list of pacing vectors for future reference. In the event that cardiac capture does not occur consistently with the most preferential vector, the cardiac pacing system will switch to those pacing vectors chosen as desirable by the patient.

Figure 25:
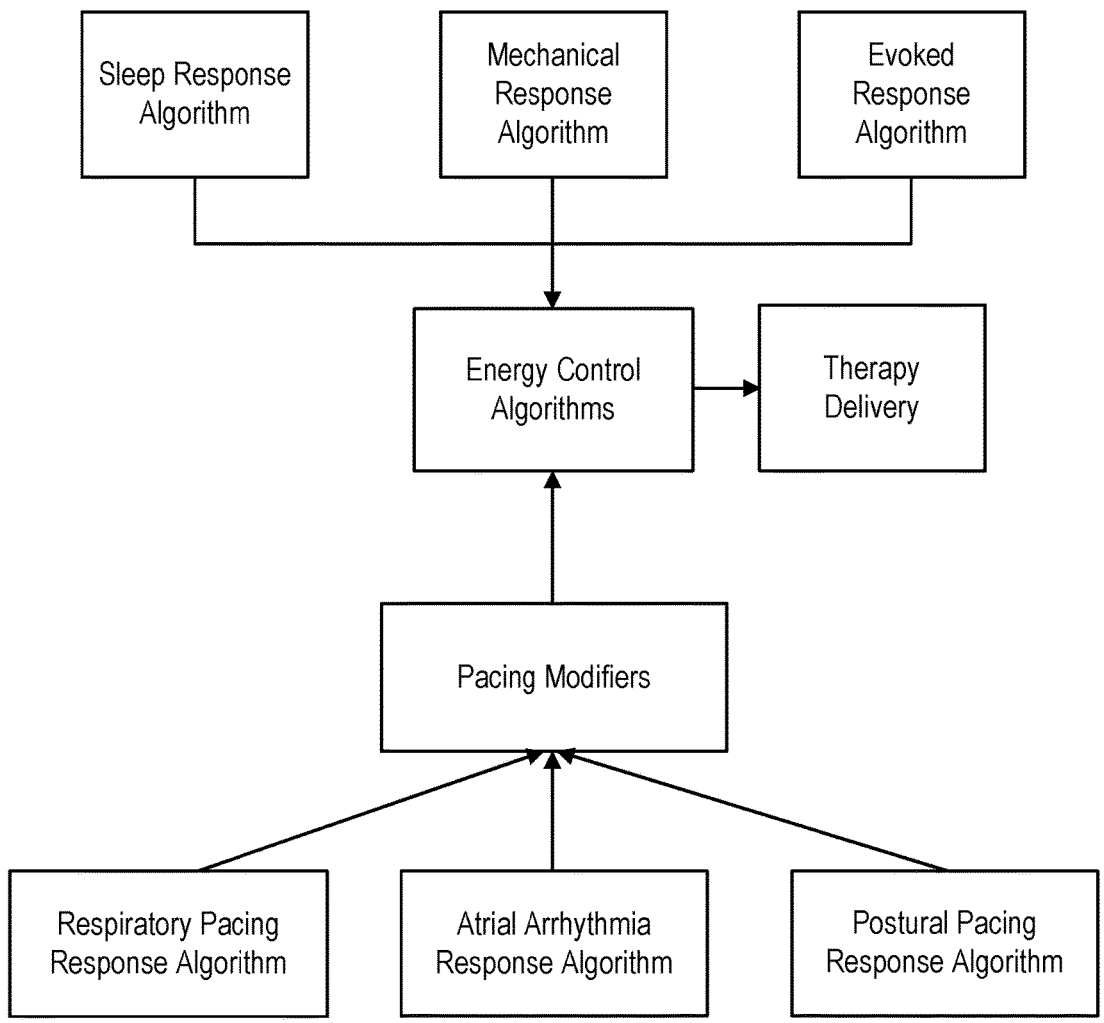

The cardiac pacing system can incorporate energy control algorithms to assist in reducing pacing energy output, resulting in a longevity increase for the cardiac pacing system. Energy control algorithms can be used to ensure that sufficient pacing energy is delivered to safely capture the heart, while minimizing energy loss due to excessive safety margins. FIG. 25 is an illustration of an exemplary process flow 2500 for analyzing sensed signals to determine whether delivered energy levels and/or pacing vectors can be adjusted, having features consistent with the present disclosure.

Pacing therapy demands are known to lessen while a patient is sleeping. Additionally, certain patient postures, such as the prone position, can reduce the pacing energy requirement for successful cardiac capture. As a result, patients that typically, or periodically, sleep on their chest, can require less pacing energy while sleeping as compared to the rest of the day when they are upright. The sleep response algorithm can use time of day, patient position information from an accelerometer or posture sensor, heart rate, ECG data, respiratory information or other sensed information to determine when a patient is sleeping and in what posture. By analyzing these sensory inputs, the sleep response algorithm can automatically reduce pacing energies or pacing rates during a sleep cycle when it is safe to do so. The sleep response algorithm may also adjust pace pulse delivery to be timed with the point of maximal exhalation in order to minimize the potential tissue space between the electrode and the heart, resulting in lower pacing energy requirements.

The pacing energy reduction can be a fixed reduction or a proportional reduction to the specific measured position. The duration of the pacing energy reduction can be automatically adjusted or can be for a fixed period. In addition to adjusting the pacing energy, the sleep response algorithm can also adjust other pacing parameters, such as pacing rate, pacing mode, rate-response settings, or the like during the sleep cycle.

A delivered pacing pulse that successfully captures the heart will cause the heart to beat resulting in mechanical movement of the heart that is measurable. The mechanical response algorithm utilizes sensors connected to the cardiac pacing system to assess mechanical movement of the heart, and adjust proper cardiac capture energy levels accordingly.

The mechanical response algorithm identifies mechanical heart deflections following the delivery of a pacing pulse using one or more accelerometer signals, other posture sensors, acoustic signals, or the like. The cardiac pacing system then gradually reduces the energy levels until a mechanical heart deflection is no longer noted by the sensors, and loss of cardiac capture is suspected. Specific timing windows may be used to ensure that the mechanical sensory information is only analyzed for a limited period of time immediately following pacing pulse delivery. Upon loss of cardiac capture, the cardiac pacing system will increase the energy level of the pacing pulse until cardiac capture is regained. The cardiac pacing system will then set that new energy level, with a specific safety margin of additional energy, as the new default pacing pulse energy level.

The mechanical response algorithm can operate continuously or operate in a periodic fashion, such as once per hour, day, week, or the like. The mechanical response algorithm can also be initiated by some other trigger mechanism such as a change in posture, time of day, heart rate, or some other physiologic event noted on the ECG, accelerometer or other signal. Throughout the energy reduction process, a backup pacing pulse at higher energy can be delivered in a delayed fashion to ensure that appropriate cardiac function is maintained despite the loss of capture due to a reduced energy pacing pulse.

A delivered pacing pulse that successfully captures the heart generally evokes a larger and wider ECG deflection than the ECG deflection caused by an intrinsic heartbeat. The evoked response algorithm uses ECG analysis for larger and wider deflections to determine if the delivered pacing pulse captured the cardiac tissue. The algorithm can also assess evoked responses by evaluating simultaneous signals other than the pacing vector and measuring changes in specific intervals relative to the time in which a pace pulse is delivered.

Immediately following pace pulse delivery, the cardiac pacing system will analyze the ECG to identify the evoked ECG response. If noted, successful capture is confirmed. The evoked response algorithm continues to pace with lower and lower energies until loss of cardiac capture is noted. The evoked response algorithm can utilize the preferred sense vector, any other ECG sense vector or physiologic signal, or any combination of multiple signals to determine if cardiac capture was successful. Upon loss of cardiac capture, the cardiac pacing system will increase the energy level of the pacing pulse until cardiac capture is regained. The cardiac pacing system will then set that new energy level, with a specific safety margin of additional energy, as the new default pacing pulse energy level.

The evoked response algorithm can operate continuously or operate in a periodic fashion, such as once per hour, day, week, or the like. The evoked response algorithm can also be initiated by some other trigger mechanism such as a change in posture, time of day, heart rate, or some other physiologic event noted on the ECG, accelerometer or other signal.

Pacing modifiers incorporate data from sensor inputs to ensure successful cardiac capture and minimize skeletal muscle stimulation. Pacing modifier algorithms can modify pacing therapy as a result of the sensor inputs. For example, the effect of noise to a cardiac pacing system can include inappropriate inhibition of life-sustaining pacing. As a result, the cardiac pacing system can include pacing modifiers that temporarily pace in an asynchronous mode if noise cannot be effectively removed. Switching to an asynchronous pacing mode in the presence of persistent noise can provide a safety mechanism to help ensure pacing is not dangerously inhibited due to noise.

Atrial arrhythmia algorithms can ensure that pacing therapy remains appropriate in response to the initiation or termination of atrial arrhythmias. Certain atrial arrhythmias can result in highly variable conduction to the ventricles. This variability causes irregular heart rate intervals which can result in symptoms for patients. An atrial arrhythmia response algorithm can include an interval threshold method to limit the degree of interval variability. In the event that the interval threshold is reached without detection of an intrinsic R-wave, a pacing pulse can be delivered. The interval threshold can be calculated based upon a percentage of some number of previous R-wave intervals and may be updated periodically or on a beat-to-beat basis. Additionally, the interval threshold method can be selectively activated such that it operates only once an atrial arrhythmia has been identified. In this example, upon termination of the atrial arrhythmia, the interval threshold method is deactivated.

The onset of an atrial arrhythmias can result in undesirable high rate or irregular ventricular pacing when the cardiac pacing system is operating in a synchronous pacing mode such as DDD(R) or VDD(R). To prevent undesirable pacing in the ventricles in response to an atrial arrhythmias, a maximum ventricular tracking rate threshold can be used. The cardiac pacing system will continue to pace the ventricles in response to atrial sensed events; however, the ventricular pacing rate cannot exceed the maximum ventricular tracking rate threshold.

Additionally, if a prolonged, highly variable or high rate atrial arrhythmia is detected, the cardiac pacing system can switch pacing modes from a tracking mode to a non-tracking mode, such as VVI(R). Switching to a non-tracking mode will ensure that the ventricles do not pace at an undesirably rapid or irregular rate in response to the atrial arrhythmia. When the cardiac pacing system detects that the atrial arrhythmia has terminated, the cardiac pacing system can revert back to a tracking mode to continue delivering atrial synchronous ventricular pacing.

The atrial arrhythmia response algorithms can work in conjunction with other physiologic sensors. For example, upon the initiation of an atrial arrhythmia, the respiratory signal can be examined to monitor for shortness of breath and certain pacemaker settings, such as pacing rate, mode, output or the like, and automatically make pacemaker setting adjustments accordingly.

The respiratory pacing response algorithm ensures that adequate energy for pacing is delivered to the patient during times of high respiration volume. When oxygen demand increases (e.g., during exercise), respiratory rates and volumes increase. An electrode placed in the anterior mediastinum can be subjected to small movements as the chest moves in response to deep inhalation/exhalation breaths. The deep breaths can additionally cause small changes in the tissue separation between the electrode and the heart.

The resulting respiration signal can be used by the cardiac pacing system to analyze the patient's breathing patterns and identify moments of increased respiratory volume. In response to these deep breaths, the pacing energy can be increased to ensure cardiac capture is maintained. Alternatively, the respiratory pacing response algorithm can delay the pacing pulse delivery until the point of maximum exhalation, thereby avoiding the need for increased energy at maximum inhalation. A pacing pulse can be selectively synchronized to breathing patterns in order to ensure cardiac capture in an energy efficient manner. The degree of energy increase can be a fixed energy increase or can be proportional to the size of respiration volume change.

The degree or method of the energy increase can be modified by the physician using a programmer. The programmer can assist in analyzing the patient's breathing patterns, including during deep inhalation. Pacing capture thresholds can be determined at varying states of inhalation and this data may be supplied to the cardiac pacing system, and used by the respiratory pacing response algorithm.

The postural pacing response algorithm ensures that adequate energy for pacing is delivered to the patient, despite changes in patient posture. Certain changes in patient posture can result in small movements of the organs or tissue within the chest. These changes can alter the separation between the heart and pacing electrodes used by the cardiac pacing system. For example, when a patient moves from a prone to supine posture, the distance between the patient's heart and the distal tip of a lead placed within the anterior mediastinum can be observed. Subsequently, an increase in the pacing energy requirement for successful cardiac capture can result. Other posture changes can similarly reduce the separation between the heart and pacing electrodes used by the cardiac pacing system, resulting in a reduction in pacing energy requirements.

A multi-axis accelerometer, or other posture sensor, can be used by the cardiac pacing system to analyze the patient's position and identify those positions that can affect pacing energy requirements. In response to a positional change, the pacing vector or energy can be modified accordingly to ensure the proper pacing energy is used and cardiac capture is maintained. The degree of energy increase/reduction can be a fixed or can be proportional to the relative position displacement.

The programmer 320 can be used to analyze the pacing requirements during various patient postures. Pacing capture thresholds can then be determined at varying positions for the postural pacing response algorithm.

The skeletal muscle response algorithm assesses whether therapeutic pacing pulses delivered by the cardiac pacing system produced undesirable skeletal muscle stimulation. Exciting skeletal muscle can result in muscle contractions. These muscle contractions can then be measured by sensitive accelerometers controlled by the cardiac pacing system. The muscle response algorithm can use signals from one or more accelerometers to compare changes in skeletal muscle deflection during pacing to skeletal muscle deflection during intrinsic heartbeat activity. Through the comparison, the cardiac pacing system can determine if the skeletal muscle response is more significant during pacing delivery. For example, the skeletal muscle response algorithm can compare signals from one accelerometer placed on a lead disposed in the anterior mediastinum to a second accelerometer within the implanted pulse generator. If skeletal muscle stimulation is noted during pacing, the skeletal muscle response algorithm can automatically adjust the pacing output until skeletal muscle stimulation is no longer observed. The skeletal muscle response algorithm can alter voltage, pulse width or a combination of both, or can automatically switch to a different pacing vector that reduces or eliminates skeletal muscle stimulation. The skeletal muscle response algorithm can additionally utilize other energy control algorithms described herein to ensure successful cardiac capture is maintained throughout the algorithmic assessment.

The programmer 320 can be used to analyze the degree of skeletal muscle stimulation observed using various pacing vectors. This information can then be calibrated with the patient's perception of the skeletal muscle stimulation to generate a prioritized list of pacing vectors the cardiac pacing system should utilize for a patient, and for what circumstances certain such pacing vectors should be adjusted if the original pacing vector possesses a high likelihood of resulting in undesirable skeletal muscle stimulation.

The cardiac pacing system can be configured to monitor, or be monitored by, a concomitant device. A concomitant device can be a device that provides different functionality than, for example, the cardiac pacing system consistent with the current disclosure. The concomitant device can be, for example, an implantable cardioverter-defibrillator (ICD). The cardiac pacing system may be configured to facilitate pacing of the heart and rely on the ICD to provide defibrillation for the heart. In response to an activation of, or by, the concomitant device, the cardiac pacing system can be configured to dynamically change the filters used by the sensor(s) disposed within the body to account for the energy or signal noise generated by the concomitant device, or may be configured to modify other parameters including pacing rate, pacing energy, sensing modes, or other features.

A concomitant device can also be another cardiac pacing system such as a transvenous, transcatheter or leadless pacing system. The cardiac pacing system may be configured to facilitate sensing of certain activities, such as the activity of one or more chambers of the heart, and rely on the concomitant device to compliment sensing through monitoring other physiological activities, such as those previously described herein. The concomitant device may also be configured to confirm the sensing activities of the cardiac pacing system. In addition to sensing, the concomitant pacing system may also be configured to add additional pacing vectors. For example, the cardiac pacing system may be the primary source of pacing for one or more chambers of the heart while acting as a backup source of pacing for other chambers, relying on the concomitant device to be the primary source of pacing for those other chambers. The cardiac pacing system can be further configured to communicate with the concomitant device. In some variations, a pulse generator, for example, can be mechanically or electronically attached to an ICD or other concomitant device. In some variations, the pulse generator and the concomitant device can communicate wirelessly.

To ensure optimal cardiac sensing and detection for a particular patient, a pre-screening assessment can be performed. This screening assessment may utilize a patient's EKG signals to predict if reliable cardiac signal sensing can be achieved by the cardiac pacing system. The EKG signals used for the assessment may be those collected via a routine multi-lead EKG evaluation, such as a standard 3-lead or 12-lead EKG. Alternatively, a specific, customized EKG evaluation may be used to more accurately reflect the anticipated cardiac signals expected to be obtained from a particular configuration of the pulse generator and associated sensors. The EKG used for assessment may be collected in a single patient posture, or may be collected in multiple postures. The EKG used for assessment may be obtained at a resting heart rate or at an elevated rate, such as with exercise. The EKG assessment may also be obtained while a patient performs other activities of daily living so that the effect of such activities on sensing may be understood Features of the screening assessments discussed herein may be implemented with the use of a physical assessment tool, such as a transparent gauge or ruler. The assessment tool can include features to help the user assess the signal amplitude, ratios, signal width, etc. and can be used by overlaying the tool over the EKG signal collected as described herein. The assessment tool can include features that allow the user to qualify acceptance of the EKG. For instance, a unique shape may be included on the assessment tool that, when aligned with a specific reference on the patient's EKG, such as the onset of the QRS complex, can be used to either accept or reject a particular EKG. The unique shape can be designed such that all, or a portion of, one or more EKG cardiac cycles fit within the unique shape. Alternatively, other shapes may be used in which the one or more EKG cardiac cycles fits outside of, or between multiple, unique shapes. The unique shape may also be designed as a straight line in which one or more elements of the EKG cardiac cycle must be compared and assessed.

Features of the screening assessments discussed herein may be implemented through software that automatically acquires the EKG signal data, performs the specific required analysis, and provides feedback facilitating the implementation of a properly located, optimized cardiac pacing system. EKG cardiac signal attributes such as P-wave, QRS, and T-wave can be evaluated for amplitude, timing, width, frequency, slew rate, biphasic vs monophasic relationships, morphology, etc. Some or all of the attributes of the cardiac signal may be analyzed to create index metric(s) for acceptability assessment. Minimum and maximum acceptable criteria may be applied to various cardiac signal attributes, to index metric(s), or to combination(s) of cardiac signal attributes and index metric(s). The present disclosure contemplates screening assessments that also utilize other sensor types disclosed herein, in addition to, or in place of, EKG sensors.

The results of a screening assessment can be used to guide the placement process for the pacemaker system. For example, the assessment may inform a desired placement for the pulse generator and its associated electrodes. The assessment may also provide information regarding the need for additional sensing devices (as discussed herein), and the appropriate location for such devices. As one example, a separate sensing input beyond the sensors associated with the pulse generator, such as an optional subcutaneous sensing electrode or array, may be recommended through the screening assessment and utilized to enhance the sensing and detection of the pacemaker system. The results of the sensing assessment process, and the assessment software itself, may also be used in the programming of the pacemaker system.

To ensure optimal cardiac sensing and detection for a particular patient, the present disclosure also contemplates the use of a pulse generator emulator prior to placement of the actual pulse generator. In contrast to the pulse generator itself, the pulse generator emulator may be non-sterile and may include the same or similar control circuitry as contained within the actual pulse generator. Alternatively, the pulse generator emulator may be a sterile device, taking a shape that allows it to be injected or inserted under the skin. In certain embodiments, the implanted pulse generator emulator may include features that protrude through the skin to assist with removal. Optionally, the pulse generator emulator may include such circuitry, or portions of it, in a separate external device (e.g., an "external analyzer") that is considered part of the pulse generator emulator. The pulse generator emulator may also include additional components or software to provide further functionality, as described herein.

The pulse generator emulator may include sensing electrodes with the same spacing and orientation as that found on the actual pulse generator. The pulse generator emulator may be temporarily placed on the skin of the patient to assess the sensed cardiac signals resulting from that particular bodily position and orientation. When positioned, the cardiac signals received from the electrodes on the pulse generator emulator may be processed by the pulse generator emulator, optionally in the external analyzer portion of the pulse generator emulator. In addition to cardiac signals, the pulse generator emulator may obtain other bodily signals such as respiration rate, pulse oximetry, temperature, motion and similar diagnostics that can affect the sensing and detection of cardiac rhythms. Additionally, the pulse generator emulator may permit the patient to provide feedback when they feel an arrhythmic event or to record audio to provide input relating to the data being sensed by the pulse generator emulator at that time. The resulting signals may then be assessed according to certain metrics, such as those described above, to determine whether they meet the required acceptability criteria.

To optimize cardiac sensing and detection, the pulse generator emulator may be repositioned to another location on the patient's skin. The resulting signals in this second position may then be assessed in accordance with the manner described above. This process may be repeated until a specific location and orientation of the pulse generator emulator appears optimal. Optionally, the pulse generator emulator, for example, through an external analyzer, may suggest directional and/or orientation movements of the pulse generator emulator to achieve an optimally sensed cardiac signal. Once the optimal location and orientation is determined, markings may be placed on the skin of the patient to be used as a reference for placement of the actual pulse generator.

To assist contact of the pulse generator emulator to the patient's skin during the evaluation process, and with different postures (e.g., with the patient supine, sitting, upright, etc.), the skin facing side of the pulse generator emulator may include a means for temporarily and reversibly adhering to the patient's skin. In certain embodiments, the adhering means may include properties that minimize movement artifacts and enhance conductivity for the electrodes on the pulse generator emulator. The adhering means may also permit the patient to wear the pulse generator emulator for multiple days/weeks/months and through daily activities (e.g., showering, exercising, sleeping) consistent with the patient's typical life.

In the case where the pulse generator emulator includes an external analyzer, the present disclosure contemplates that the external analyzer may be removed from the lab and left connected to the patient for extended periods of time. For example, the external analyzer may be adhered to the patient's skin in a similar manner as described above or affixed to the patient's belt, or attached by a strap, lanyard or other similar means. When removed from the lab, the external analyzer may record the resulting cardiac signals for future download and analysis by a caregiver. Alternatively, the external analyzer may continuously, or periodically, send data to the analyzing caregiver via remote connection. In certain embodiments, the pulse generator emulator may house all of the necessary electrical components (i.e., not including them in an external analyzer), thereby creating a single unit that may be adhered to the patient's skin during the evaluation process.

The pacing leads disclosed herein may be used for temporary cardiac pacing, for example, to provide pacing only during a procedure, during a hospital stay, or during a period of time within or outside of a hospital stay where a patient's need for a pacemaker is temporary. In such circumstances, lead(s) are delivered and placed in accordance with the description above, for example, lead(s) may be inserted through an intercostal space associated with the cardiac notch of the left lung so that the lead may be placed in the anterior mediastinum without lung tissue interposed between the lead and the pericardium. Such lead(s) are then connected to a pulse generator that provides pacing pulse energy to electrodes on the lead(s). In certain embodiments, disclosed above, the pulse generator, and the electrodes disposed on the pulse generator, may be placed adjacent, near, or over the sternum of a patient to assist with cardiac sensing. In one particular embodiment, the pulse generator may be adhered to the skin of the patient in a manner similar to that described above with regard to the pulse generator emulator. In such an embodiment, electrodes on the pulse generator may be used for cardiac sensing as discussed herein. In other embodiments, the pulse generator may not be directly attached to the patient; for example, it could be located on a patient's belt, worn on a lanyard around the patient's neck, or otherwise portable but electrically connected to the implanted lead(s). In such embodiments, cardiac sensing measurements would be provided by sensors on the lead(s) such as those described in detail above rather than by electrodes on the pulse generator itself. In yet other embodiments, the pulse generator described above may be of the form of an external defibrillation system, either attached to the patient or otherwise portable but electrically connected to the implanted lead(s). The implanted lead(s) can be used for the delivery of pacing or defibrillation energy.

In one embodiment, the pulse generator emulator described above may be used to receive cardiac signals and to provide those signals to the pulse generator. Once the optimal location and orientation of the pulse generator emulator is determined, the pulse generator emulator may be temporarily adhered to the patient's skin. The pulse generator emulator may then be electrically connected to the actual pulse generator, which will provide the pacing energy to the lead(s).

In alternative embodiments, the pulse generator emulator may itself act as the pulse generator for temporary pacing. In such embodiments, in addition to sensing electrodes, the pulse generator emulator would contain the electrical components common to the actual pulse generators described herein. The pulse generator emulator may then be adhered to the patient's skin in accordance with the description described above and connected to the pacing lead(s). As such, the pulse generator emulator may be configured to act as a pulse generator external to the patient.

While components have been described herein in their individual capacities, it will be readily appreciated the functionality of individually described components can be attributed to one or more other components or can be split into separate components. This disclosure is not intended to be limiting to the exact variations described herein, but is intended to encompass all implementations of the presently described subject matter.

In the descriptions above, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results.

What is claimed is:

1. A cardiac pacing method comprising:
    inserting a lead into an intercostal space in the region of a cardiac notch of a patient, the lead having a distal end configured to transmit therapeutic electrical pulses to a patient's heart; and,
    connecting the lead to a pulse generator, the pulse generator configured to generate the therapeutic electrical pulses for pacing the patient's heart.

2. The method as in claim 1 further comprising implanting the pulse generator within the patient.

3. The method as in claim 1 further comprising positioning the pulse generator outside of a patient's rib cage.

4. The method as in claim 1, wherein inserting the lead further comprises positioning the distal end within the intercostal space.

5. The method as in claim 1, wherein inserting the lead further comprises positioning the distal end on the inner surface of the innermost intercostal muscle.

6. The method as in claim 1, wherein inserting the lead further comprises positioning the distal end within the mediastinum, proximate the heart, but not physically in contact with the heart.

* * * * *